(12) United States Patent
Kuracina et al.

(10) Patent No.: US 6,860,871 B2
(45) Date of Patent: *Mar. 1, 2005

(54) NEEDLE TIP GUARD FOR PERCUTANEOUS ENTRY NEEDLES

(75) Inventors: Thomas C Kuracina, Ojai, CA (US); Randall E. Ohnemus, Ventura, CA (US); Craig W. Smith, Ventura, CA (US); Richard Cohen, Ventura, CA (US); David Rollo, Bonsall, CA (US)

(73) Assignee: Injectimed, Inc., Ventura, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/442,376

(22) Filed: May 21, 2003

(65) Prior Publication Data

US 2003/0195479 A1 Oct. 16, 2003

Related U.S. Application Data

(63) Continuation of application No. 09/846,706, filed on Apr. 30, 2001, now Pat. No. 6,629,959.

(51) Int. Cl.[7] .................................................. A61M 5/32
(52) U.S. Cl. ........................................................ 604/192
(58) Field of Search ................................ 604/192, 198, 604/263, 187, 110; 128/919

(56) References Cited

U.S. PATENT DOCUMENTS

| | | |
|---|---|---|
| 703,296 A | 6/1902 | Nuesch |
| 1,125,887 A | 1/1915 | Schimmel |
| 1,272,104 A | 7/1918 | Riethmueller |
| 1,274,081 A | 7/1918 | Riethmueller |
| 1,436,707 A | 11/1922 | Gaschke |
| 1,899,492 A | 2/1933 | Beebe |
| 2,091,438 A | 8/1937 | Epstein |
| 2,409,979 A | 10/1946 | Huber |
| 2,484,657 A | 1/1949 | Son |
| 2,559,474 A | 7/1951 | Son |
| 2,717,599 A | 9/1955 | Huber |
| 2,748,769 A | 6/1956 | Huber |
| 2,828,744 A | 4/1958 | Hirsch et al. |
| 2,922,420 A | 1/1960 | Cheng |
| 3,093,134 A | 6/1963 | Roehr |

(List continued on next page.)

FOREIGN PATENT DOCUMENTS

| | | |
|---|---|---|
| CA | 977461 | 11/1975 |
| CA | 996434 | 9/1976 |
| CA | 996435 | 9/1976 |
| DE | 312993 | 6/1919 |
| DE | 2 335 869 | 7/1973 |

(List continued on next page.)

*Primary Examiner*—Manuel Mendez
(74) *Attorney, Agent, or Firm*—Stetina Brunda Garred & Brucker

(57) ABSTRACT

A needle tip protective device for use with percutaneous entry needles. In one embodiment, the needle tip protective device includes a needle guard slidably mounted on a hypodermic needle, the latter having a needle tip located at the distal end thereof, and a change of profile formed medially there along. The needle guard is movable along the hypodermic needle and engageable with the change in profile formed thereon. The engagement with the change in profile is configured to correspond with the ability of the needle trap to entrap the needle tip once the needle trap has advanced the sufficient distance distally along the hypodermic needle. In further refinements, the needle trap may be biased toward the distal needle tip of the needle.

10 Claims, 51 Drawing Sheets

U.S. PATENT DOCUMENTS

| | | |
|---|---|---|
| 3,134,380 A | 5/1964 | Armao |
| 3,386,438 A | 6/1968 | Stevens |
| 3,483,810 A | 12/1969 | Peters |
| 3,492,992 A | 2/1970 | Kurtz |
| 3,530,492 A | 9/1970 | Ferber |
| 3,645,268 A | 2/1972 | Capote |
| 3,662,754 A | 5/1972 | Halloran |
| 3,727,613 A | 4/1973 | Sorenson et al. |
| 3,765,420 A | 10/1973 | Felczak |
| 3,776,239 A | 12/1973 | Cooley |
| 3,884,220 A | 5/1975 | Hartnett |
| 3,995,629 A | 12/1976 | Patel |
| 4,040,427 A | 8/1977 | Winnie |
| 4,091,811 A | 5/1978 | Bates et al. |
| 4,139,009 A | 2/1979 | Alvarez |
| 4,324,236 A | 4/1982 | Gordon et al. |
| 4,431,426 A | 2/1984 | Groshong et al. |
| 4,460,356 A | 7/1984 | Moseley |
| 4,683,916 A | 8/1987 | Raines |
| 4,692,142 A | 9/1987 | Dignam et al. |
| 4,693,708 A | 9/1987 | Wanderer et al. |
| 4,731,059 A | 3/1988 | Wanderer et al. |
| 4,735,612 A | 4/1988 | Chevalier |
| 4,743,232 A | 5/1988 | Kruger |
| 4,755,170 A | 7/1988 | Golden |
| 4,760,847 A | 8/1988 | Vaillancourt |
| 4,790,828 A | 12/1988 | Dumbrowski et al. |
| 4,795,432 A | 1/1989 | Karczmer |
| 4,834,718 A | 5/1989 | McDonald |
| 4,838,853 A | 6/1989 | Parisi |
| 4,850,977 A | 7/1989 | Bayless |
| 4,887,998 A | 12/1989 | Martin et al. |
| 4,917,673 A | 4/1990 | Coplin |
| 4,921,490 A | 5/1990 | Spier et al. |
| 4,944,728 A | 7/1990 | Carrell et al. |
| 4,944,731 A | 7/1990 | Cole |
| 4,964,854 A | 10/1990 | Luther |
| 4,978,344 A | 12/1990 | Dumbrowski et al. |
| 4,994,041 A | 2/1991 | Dumbrowski et al. |
| 4,998,922 A | 3/1991 | Kuracina et al. |
| 5,000,740 A | 3/1991 | Ducharme et al. |
| 5,013,304 A | 5/1991 | Russell et al. |
| 5,049,136 A | 9/1991 | Johnson |
| 5,051,109 A | 9/1991 | Simon |
| 5,053,014 A | 10/1991 | Van Heugten |
| 5,057,079 A | 10/1991 | Tiemann et al. |
| 5,059,180 A | 10/1991 | McLees |
| 5,085,648 A | 2/1992 | Purdy et al. |
| 5,090,564 A | 2/1992 | Chimienti |
| 5,092,851 A | 3/1992 | Ragner |
| 5,104,385 A | 4/1992 | Huband |
| 5,120,321 A | 6/1992 | Oksman et al. |
| 5,120,324 A | 6/1992 | Sancoff |
| 5,135,504 A | 8/1992 | McLees |
| 5,147,327 A | 9/1992 | Johnson |
| 5,176,650 A | 1/1993 | Haining |
| 5,176,655 A | 1/1993 | McCormick et al. |
| 5,188,617 A | 2/1993 | Linder |
| 5,195,982 A | 3/1993 | Hoenig |
| 5,195,992 A | 3/1993 | Dudar et al. |
| 5,201,713 A | 4/1993 | Rossetti |
| 5,215,528 A | 6/1993 | Purdy et al. |
| 5,217,437 A | 6/1993 | Talonn et al. |
| 5,221,266 A | 6/1993 | Kastan |
| 5,242,414 A | 9/1993 | Fischell et al. |
| RE34,416 E | 10/1993 | Lemieux |
| 5,254,099 A | 10/1993 | Kuracina et al. |
| 5,254,100 A | 10/1993 | Huband |
| 5,254,120 A | 10/1993 | Cinberg et al. |
| 5,256,153 A | 10/1993 | Hake |
| 5,261,894 A | 11/1993 | Smith et al. |
| 5,269,765 A | 12/1993 | Kuracina |
| 5,273,540 A | 12/1993 | Luther et al. |
| 5,279,588 A | 1/1994 | Nicoletti et al. |
| 5,279,591 A | 1/1994 | Simon |
| 5,300,045 A | 4/1994 | Plassche, Jr. |
| 5,304,151 A | 4/1994 | Kuracina |
| 5,312,345 A | 5/1994 | Cole |
| 5,312,366 A | 5/1994 | Vaillancourt |
| 5,312,422 A | 5/1994 | Trott |
| 5,314,414 A | 5/1994 | Hake et al. |
| 5,314,503 A | 5/1994 | Bobrove et al. |
| 5,322,517 A | 6/1994 | Sircom et al. |
| 5,334,149 A | 8/1994 | Nortman et al. |
| 5,334,158 A | 8/1994 | McLees |
| 5,336,185 A | 8/1994 | Lynch et al. |
| 5,336,197 A | 8/1994 | Kuracina et al. |
| 5,348,544 A | 9/1994 | Sweeney et al. |
| 5,360,211 A | 11/1994 | Smith et al. |
| 5,360,404 A | 11/1994 | Novacek et al. |
| 5,360,408 A | 11/1994 | Vailancourt |
| 5,360,416 A | 11/1994 | Ausherman et al. |
| 5,364,360 A | 11/1994 | Flumene et al. |
| 5,364,370 A | 11/1994 | Szerlip et al. |
| 5,364,373 A | 11/1994 | Waskonig et al. |
| 5,380,296 A | 1/1995 | Smedley et al. |
| 5,395,347 A | 3/1995 | Blecher et al. |
| 5,407,431 A | 4/1995 | Botich et al. |
| 5,411,486 A | 5/1995 | Zadini et al. |
| 5,423,766 A | 6/1995 | Di Cesare |
| 5,425,720 A | 6/1995 | Rogalsky et al. |
| 5,425,721 A | 6/1995 | Malenchek |
| 5,447,501 A | 9/1995 | Karlsson et al. |
| 5,449,349 A | 9/1995 | Sallee et al. |
| 5,458,658 A | 10/1995 | Sircom |
| 5,462,062 A | 10/1995 | Rubinstein et al. |
| 5,462,533 A | 10/1995 | Daugherty |
| 5,466,223 A | 11/1995 | Bressler et al. |
| 5,478,313 A | 12/1995 | White |
| 5,486,164 A | 1/1996 | Streck |
| 5,487,733 A | 1/1996 | Caizza et al. |
| 5,495,855 A | 3/1996 | Dudar et al. |
| 5,498,241 A | 3/1996 | Fabozzi |
| 5,498,243 A | 3/1996 | Vallelunga et al. |
| 5,509,907 A | 4/1996 | Bevilacqua |
| 5,514,099 A | 5/1996 | McCarthy |
| 5,514,113 A | 5/1996 | Anderson et al. |
| 5,540,667 A | 7/1996 | Tanner, II |
| 5,554,126 A | 9/1996 | Filley |
| 5,558,651 A | 9/1996 | Crawford et al. |
| 5,562,631 A | 10/1996 | Bogert |
| 5,562,633 A | 10/1996 | Wozencroft |
| 5,562,634 A | 10/1996 | Flumene et al. |
| 5,573,510 A | 11/1996 | Isaacson |
| 5,582,597 A | 12/1996 | Brimhall et al. |
| 5,584,810 A | 12/1996 | Brimhall |
| 5,584,818 A | 12/1996 | Morrison |
| 5,595,566 A | 1/1997 | Vallelunga et al. |
| 5,599,310 A | 2/1997 | Bogert |
| 5,601,536 A | 2/1997 | Crawford |
| 5,662,619 A | 9/1997 | Zarate |
| 5,669,890 A | 9/1997 | Grimm |
| 5,716,348 A | 2/1998 | Marinacci et al. |
| 5,795,336 A * | 8/1998 | Romano et al. ............ 604/192 |
| 5,810,780 A | 9/1998 | Brimhall et al. |
| 5,853,393 A | 12/1998 | Bogert |
| 5,858,006 A | 1/1999 | Van der AA et al. |
| 5,868,721 A | 2/1999 | Marinacci et al. |
| 5,938,635 A | 8/1999 | Kuhle |
| 6,004,294 A | 12/1999 | Brimhall |
| 6,004,302 A | 12/1999 | Brierley |

| | | | | | | |
|---|---|---|---|---|---|---|
| 6,024,726 | A | 2/2000 | Hill | DE | 29 22 239 | 5/1979 |
| 6,039,715 | A | 3/2000 | Mackool | DE | 37 39 840 | 11/1987 |
| 6,117,108 | A | 9/2000 | Woehr et al. | EP | 1 180 381 A1 | 2/2002 |
| 6,149,630 | A | 11/2000 | Robinson | EP | 1 250 943 A1 | 10/2002 |
| 6,224,569 | B1 | 5/2001 | Brimhall et al. | FR | 2 201 905 | 10/1972 |
| 6,258,067 | B1 | 7/2001 | Hill | FR | 2 408 354 | 11/1977 |
| 6,287,278 | B1 | 9/2001 | Woehr | GB | 1133555 | 11/1968 |
| 6,379,333 | B1 | 4/2002 | Brimhall et al. | GB | 1 425 388 | 12/1973 |
| 6,443,929 | B1 * | 9/2002 | Kuracina et al. ........... 604/192 | GB | 2 252 046 A | 7/1992 |
| 6,592,553 | B2 | 7/2003 | Zhang et al. | IT | 540528 | 6/1954 |
| 2001/0011171 | A1 | 8/2001 | Alchas | SU | 238082 | 1/1968 |
| 2001/0012925 | A1 | 8/2001 | Alchas | SU | 136008 | 6/1972 |
| 2001/0053895 | A1 | 12/2001 | Vaillancourt | SU | 955935 | 7/1982 |
| 2002/0103463 | A1 | 8/2002 | Luther | WO | WO 81/00210 | 2/1981 |
| 2003/0060774 | A1 | 3/2003 | Woehr et al. | WO | WO 90/04988 | 5/1990 |
| 2003/0144627 | A1 | 7/2003 | Woehr et al. | WO | WO 94/00172 | 1/1994 |
| | | | | WO | WO 02/060515 A1 | 8/2002 |

FOREIGN PATENT DOCUMENTS

DE 29 01 302 1/1979

\* cited by examiner

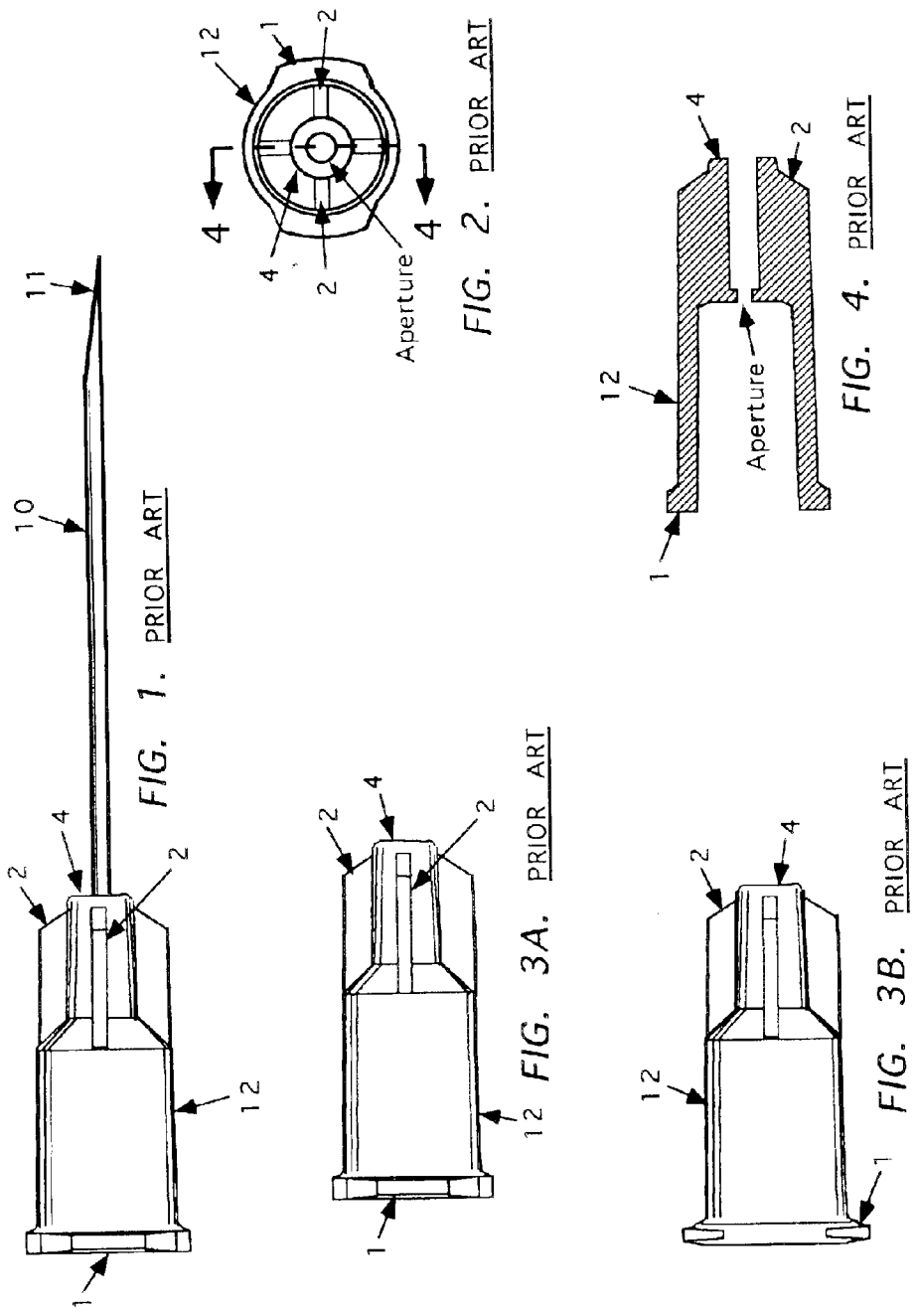

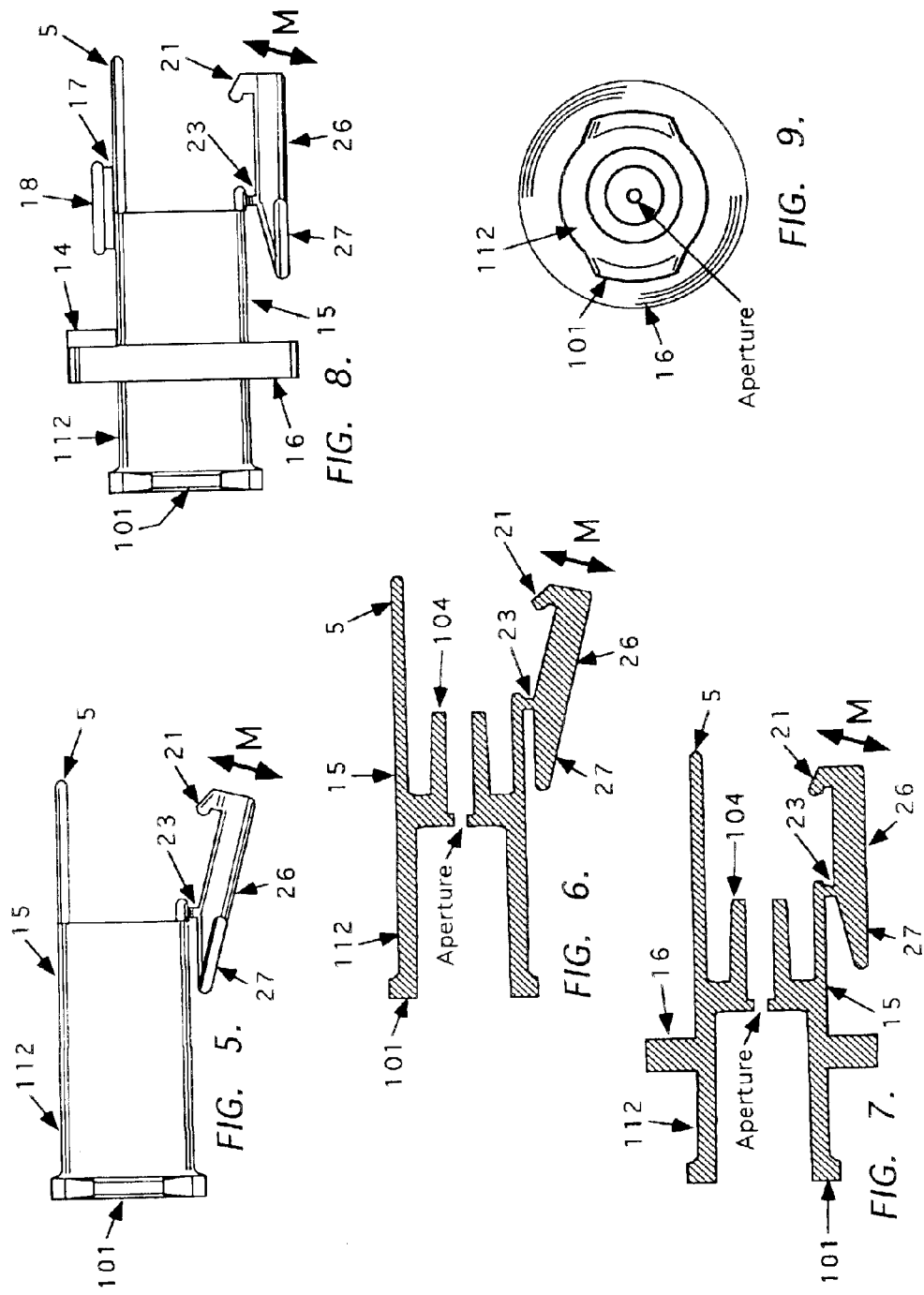

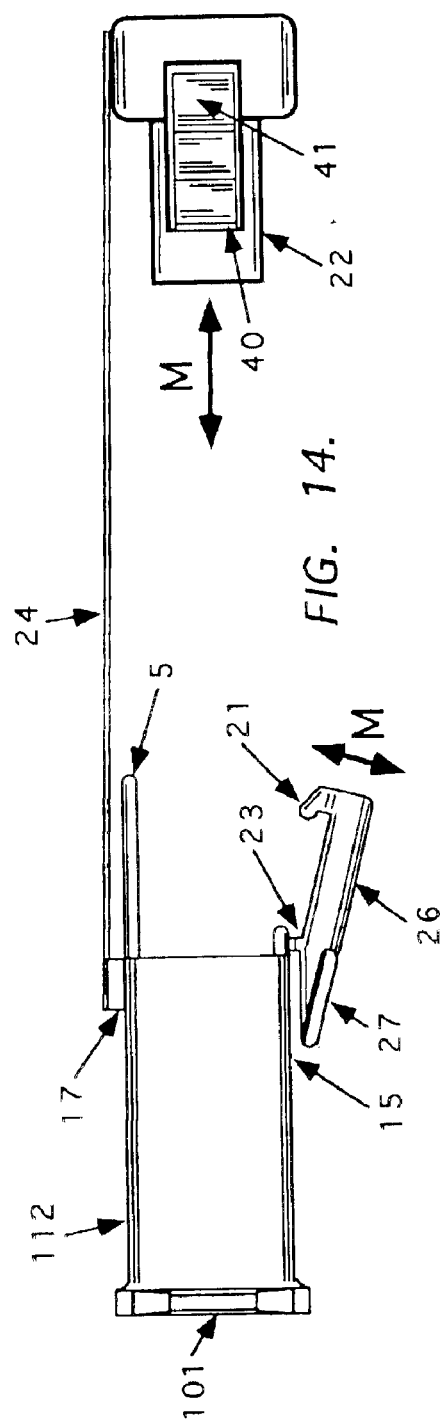
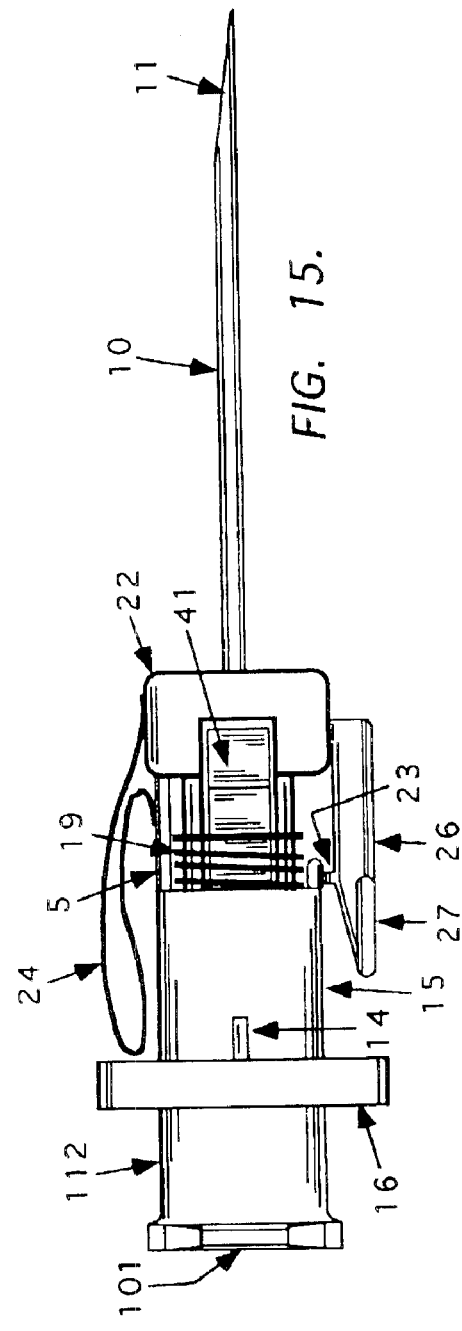

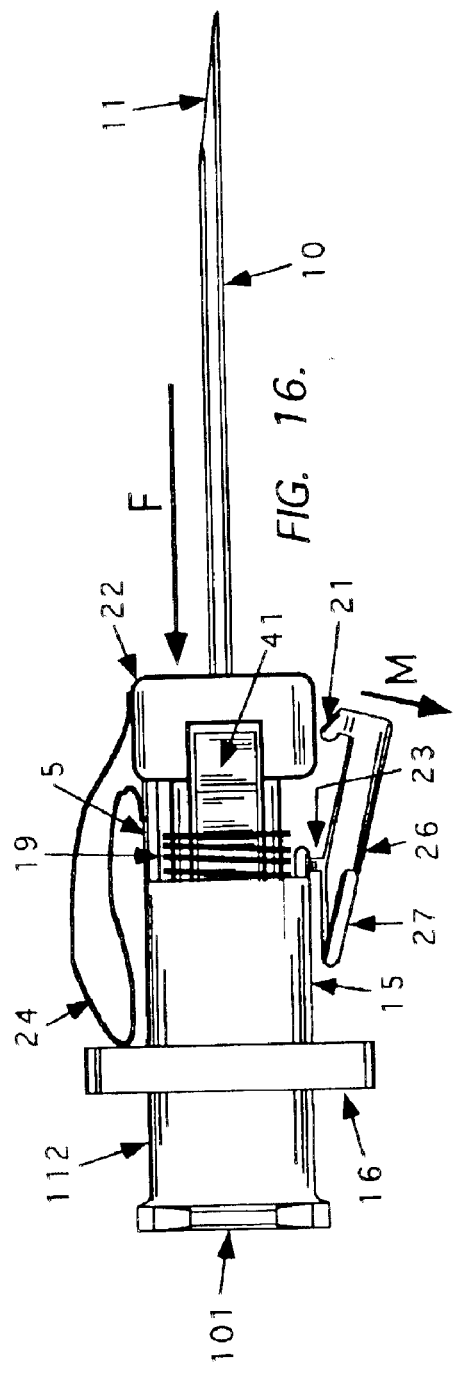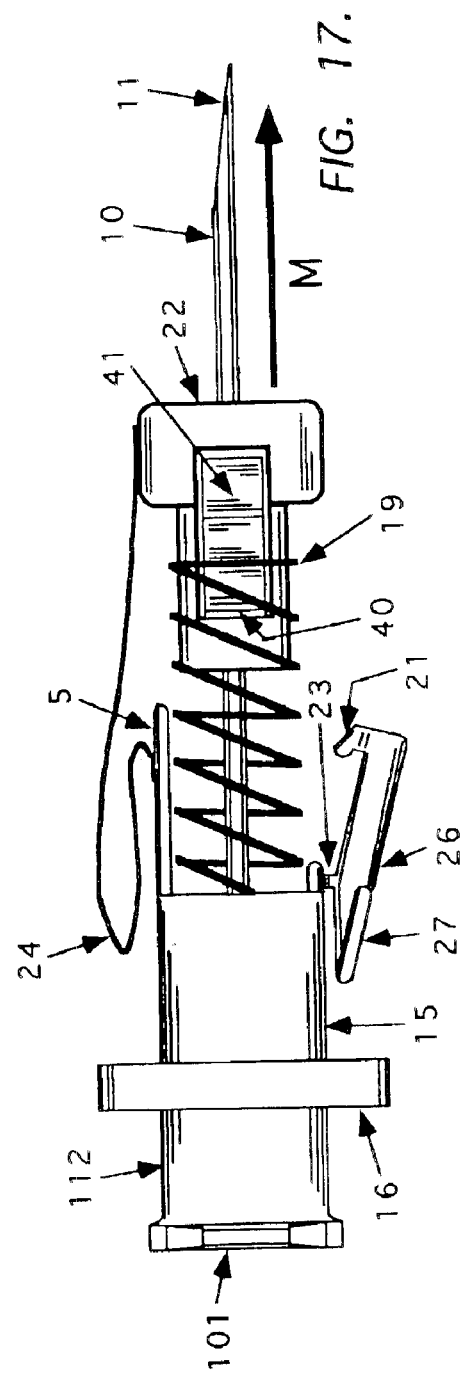

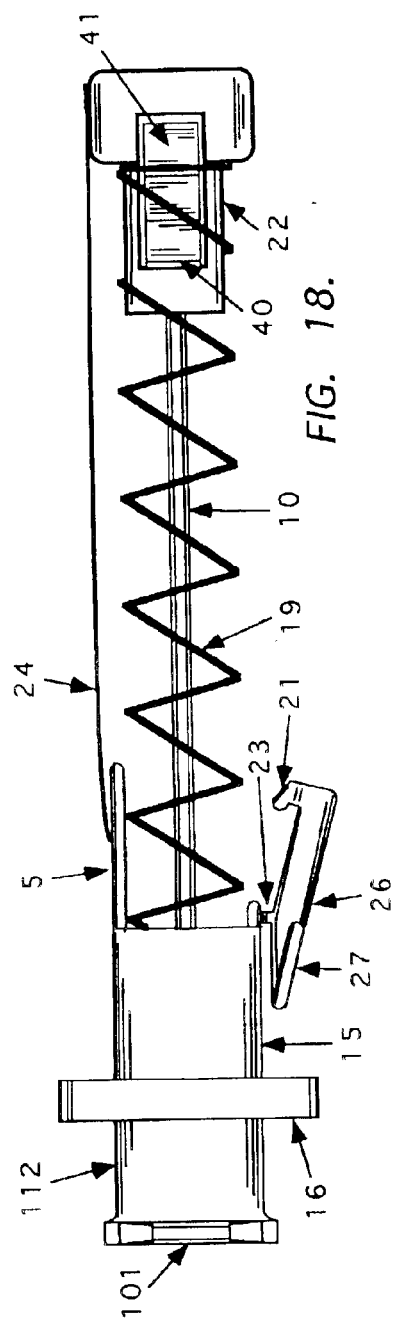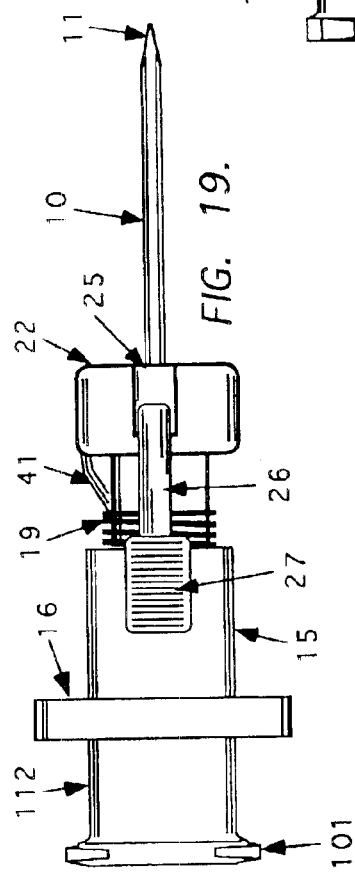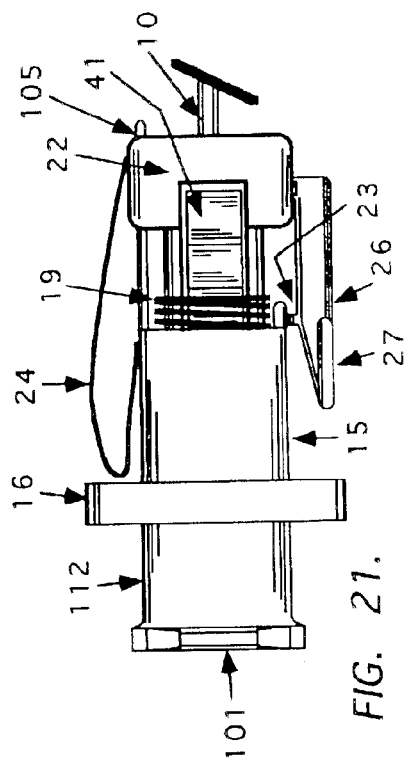

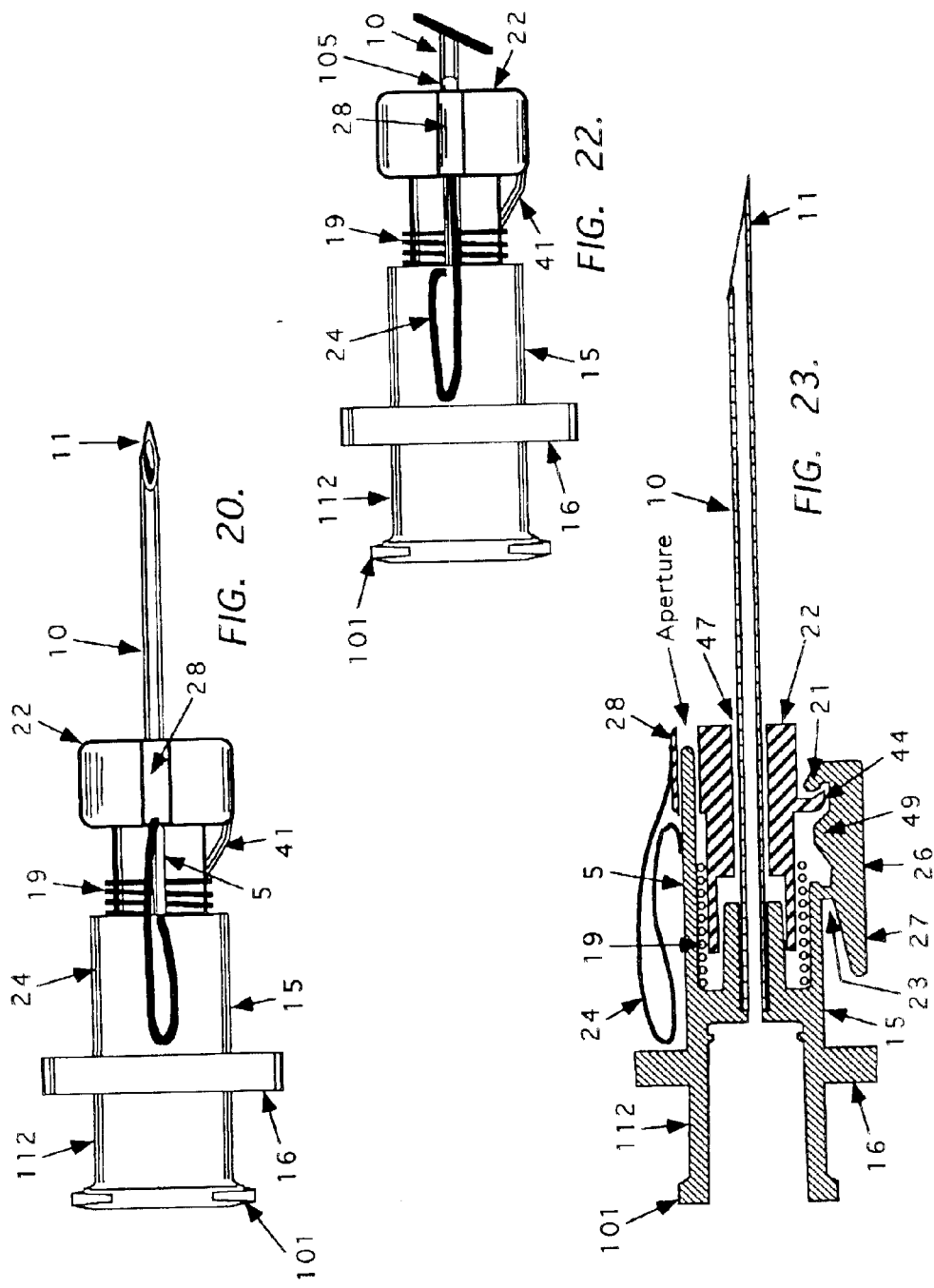

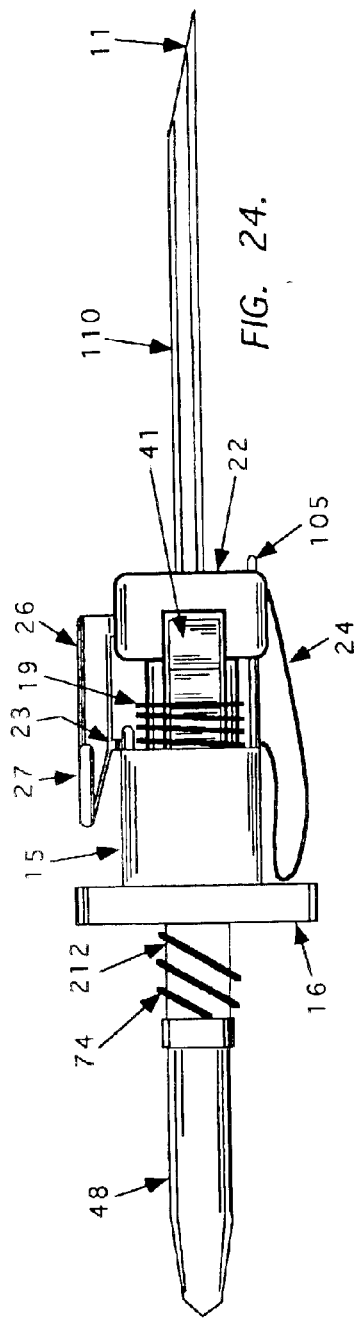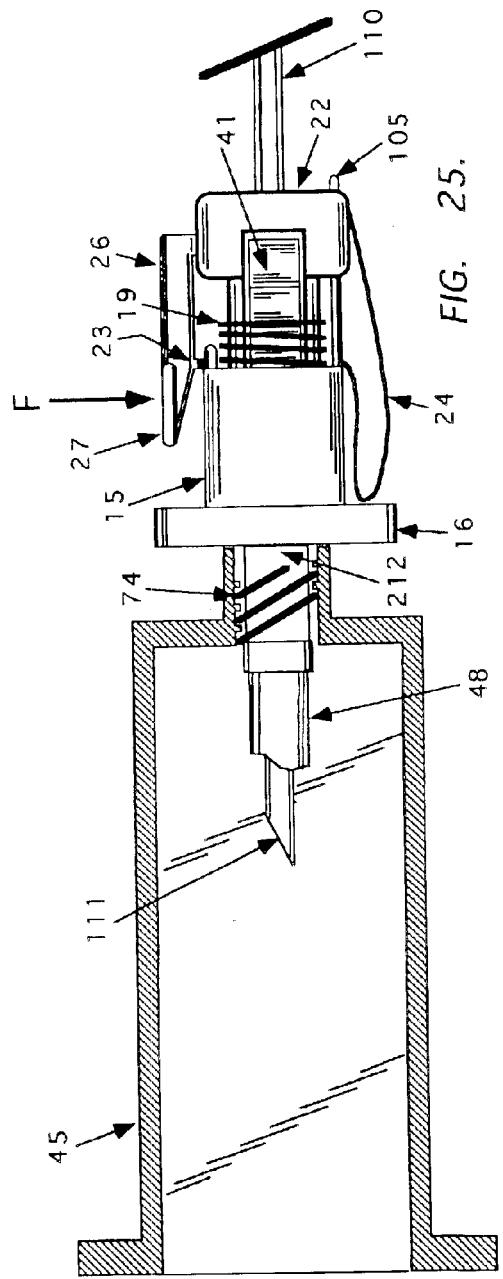

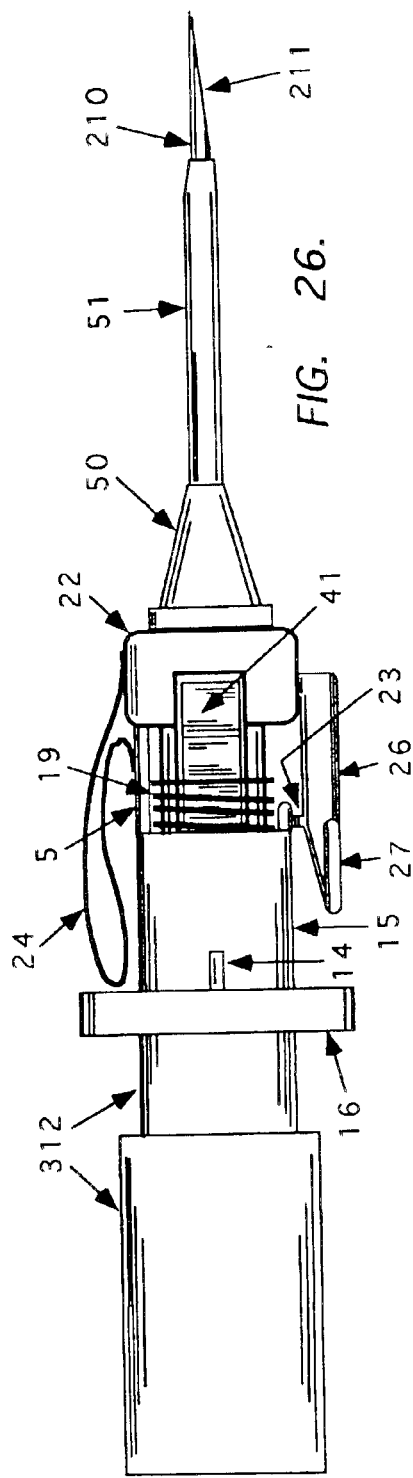
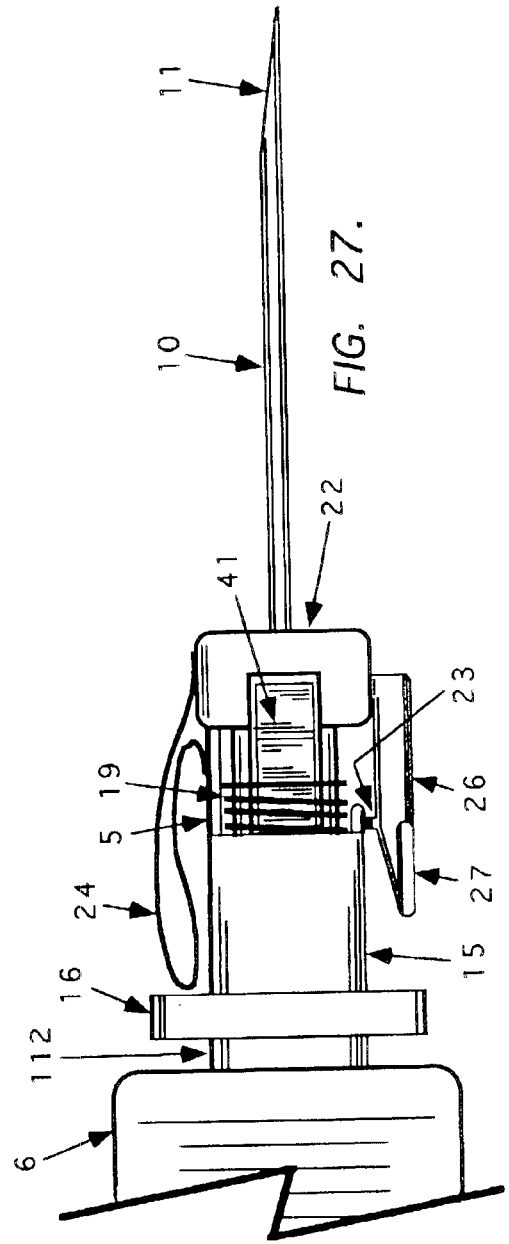
FIG. 26.
FIG. 27.

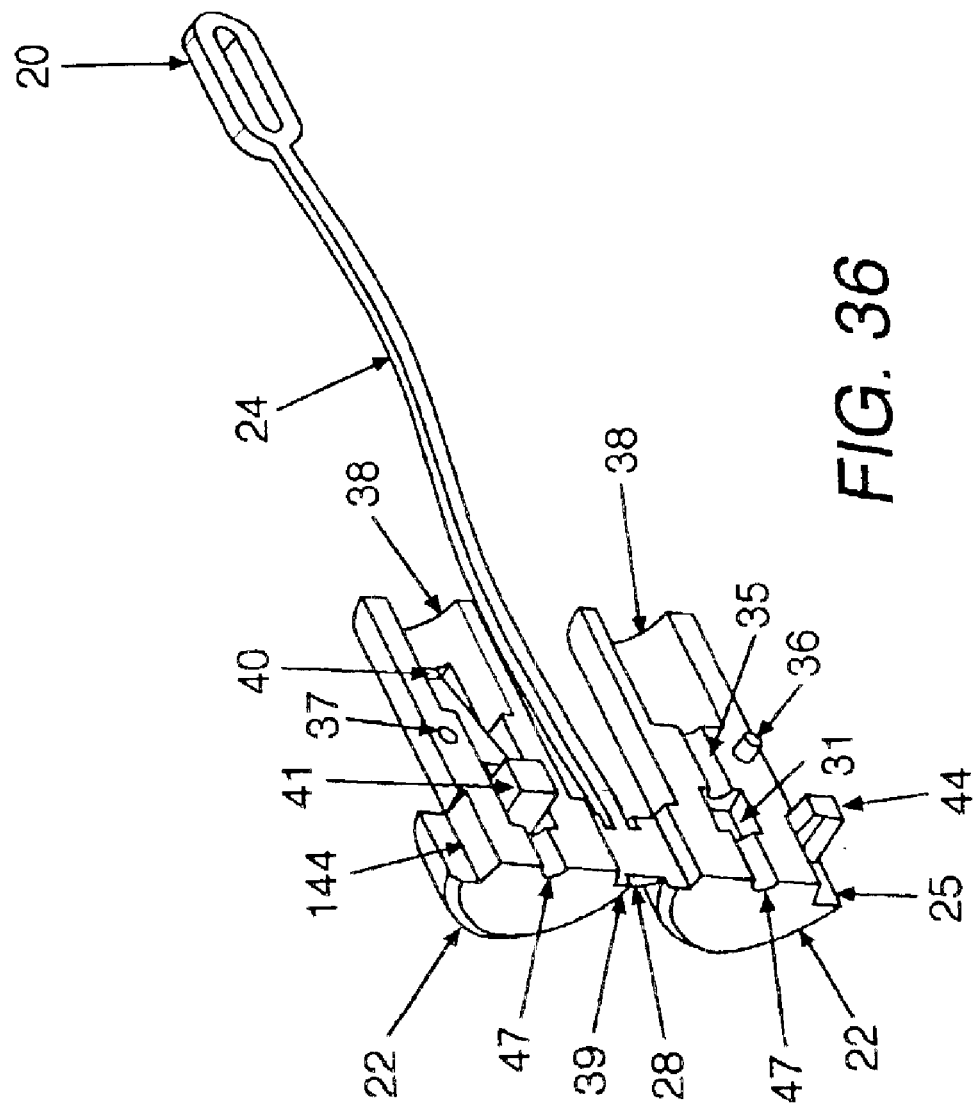

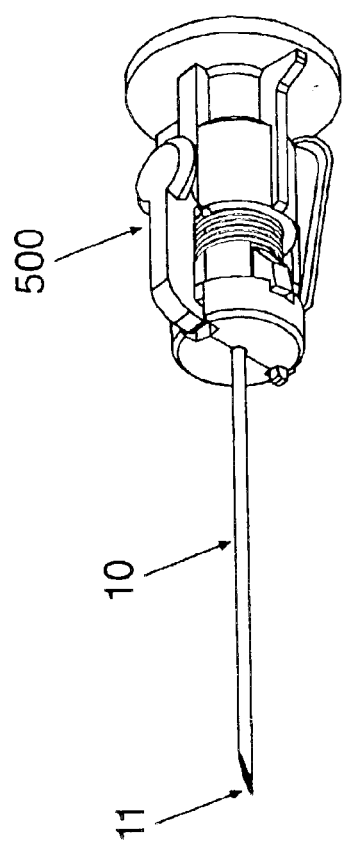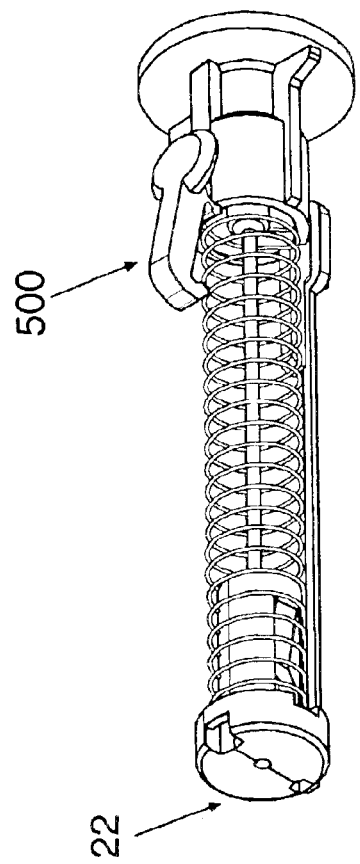

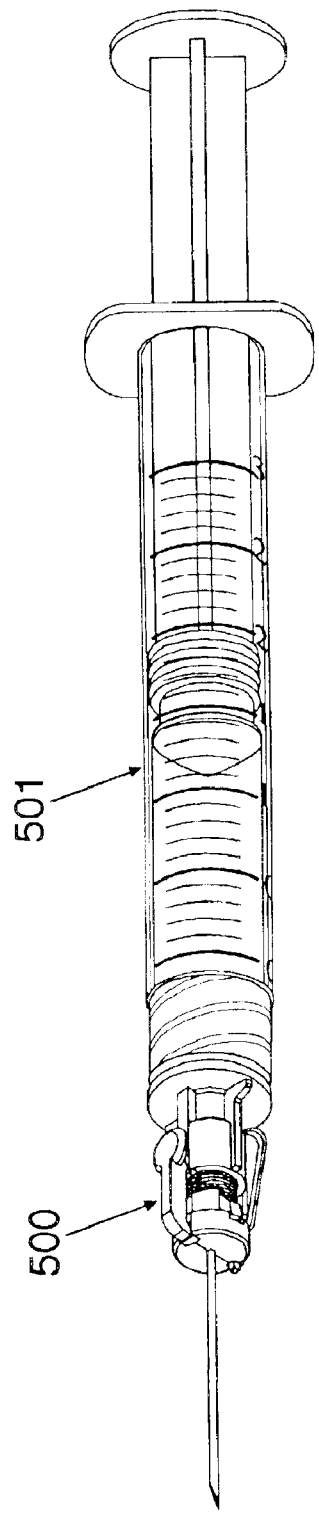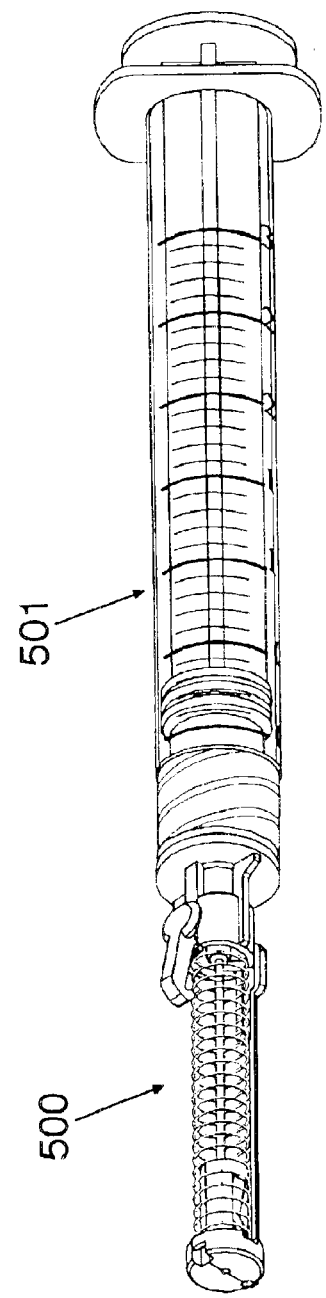

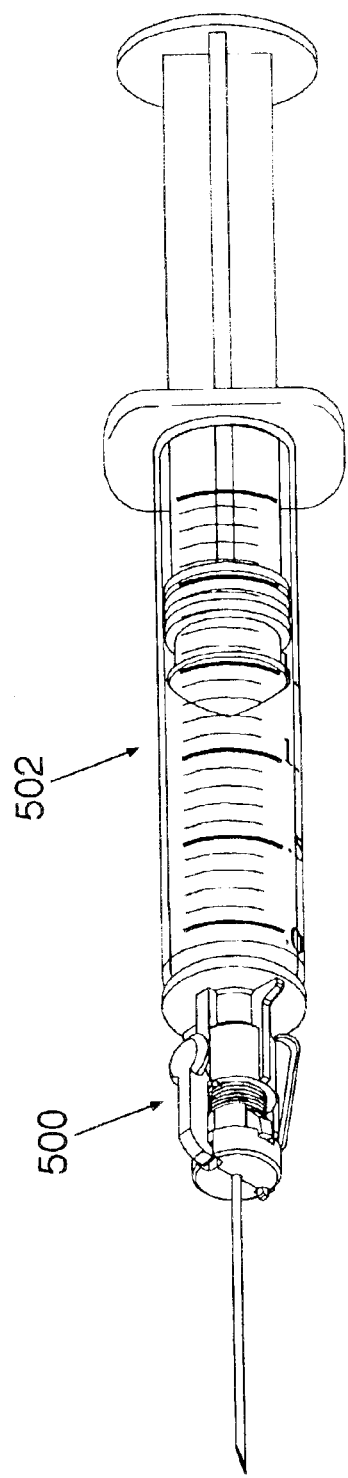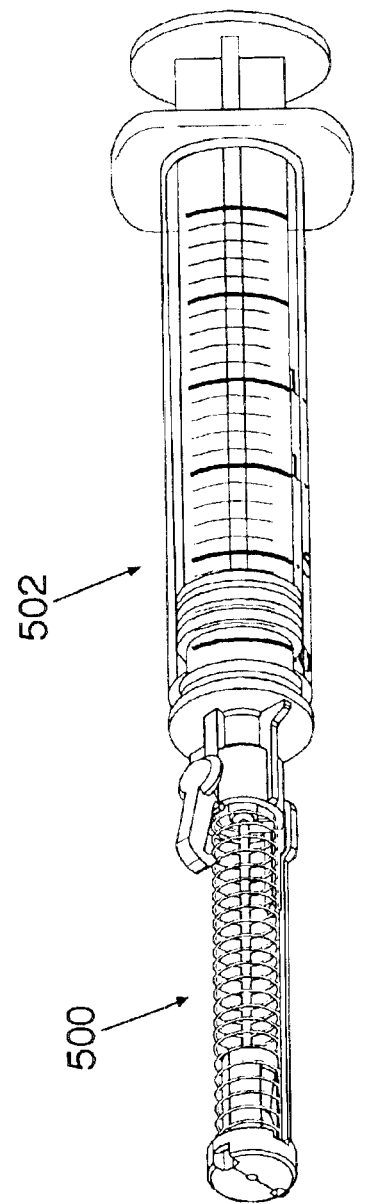

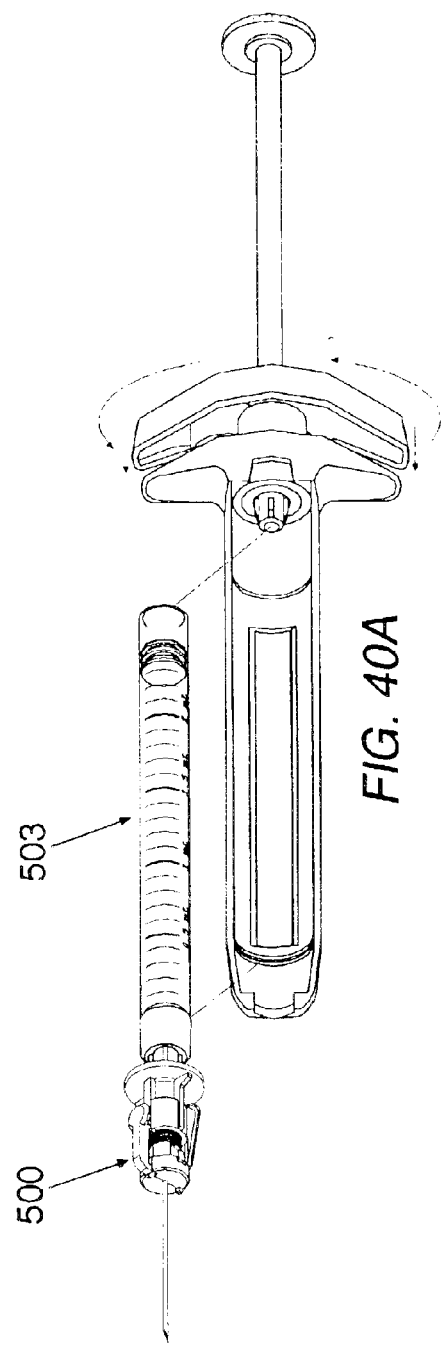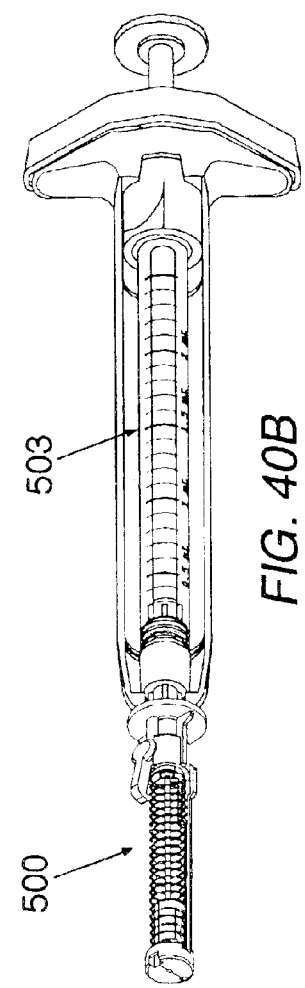
FIG. 40A
FIG. 40B

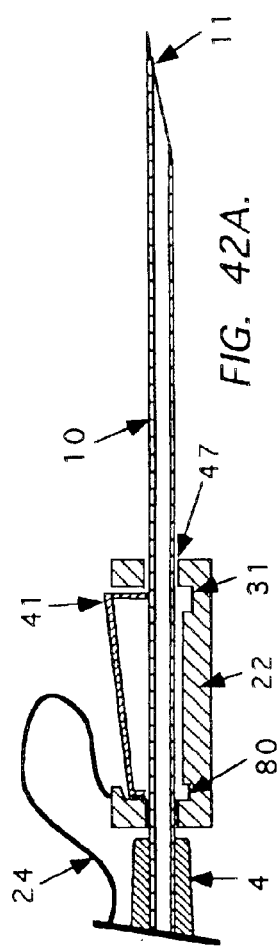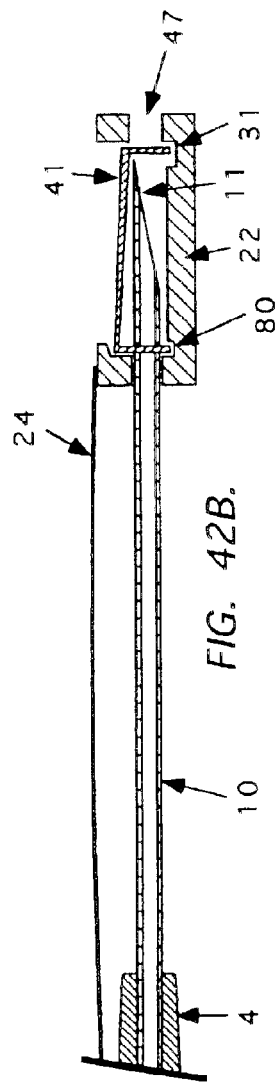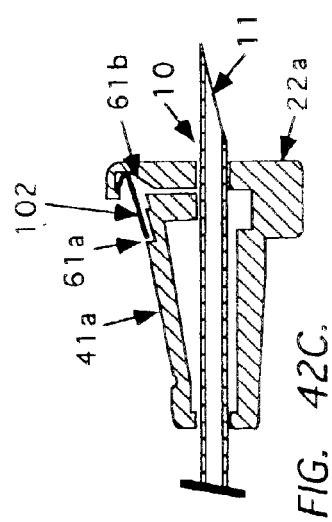

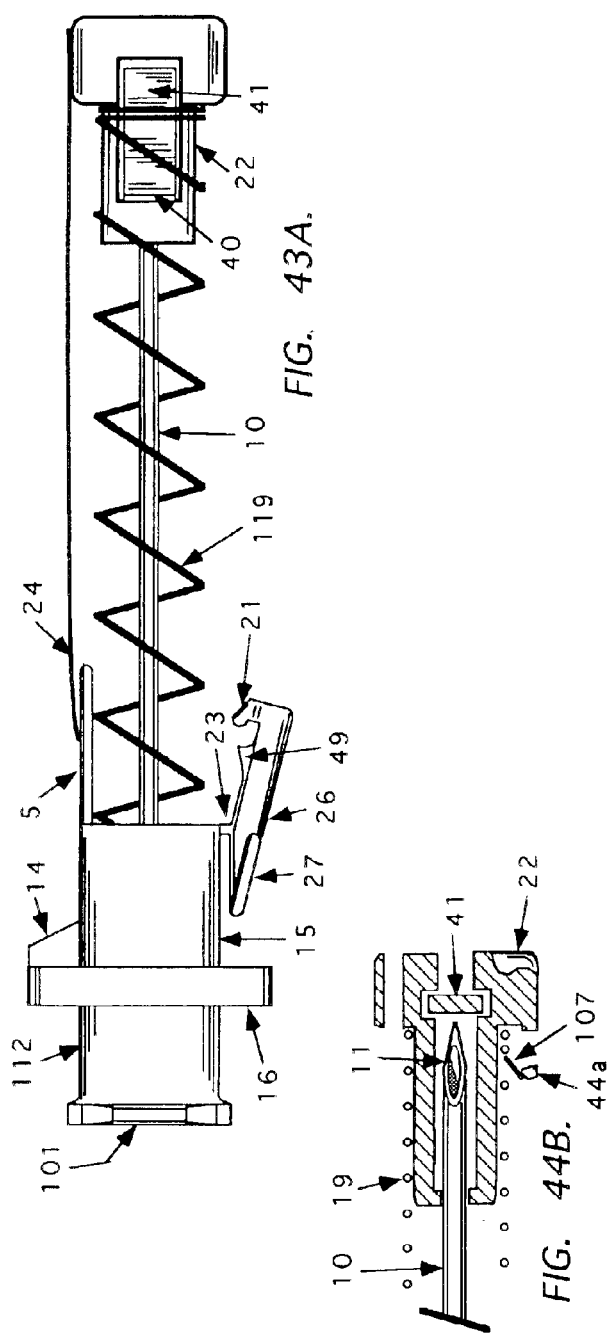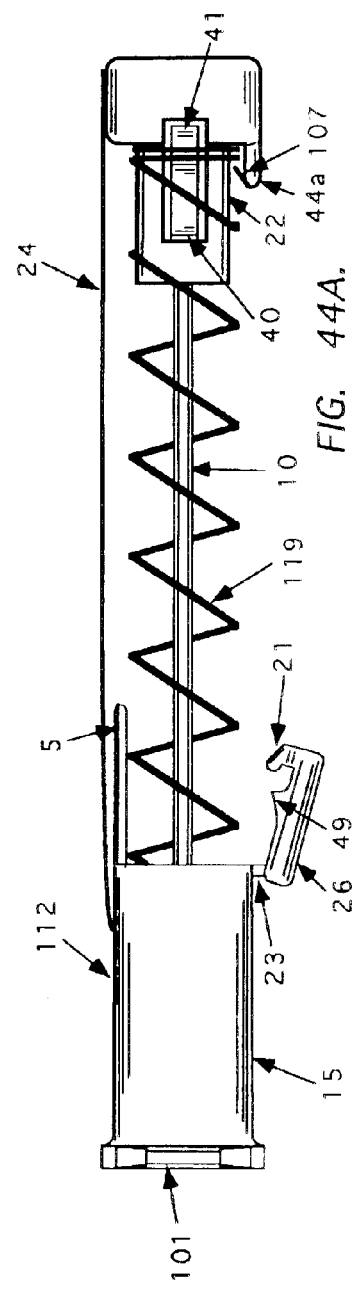

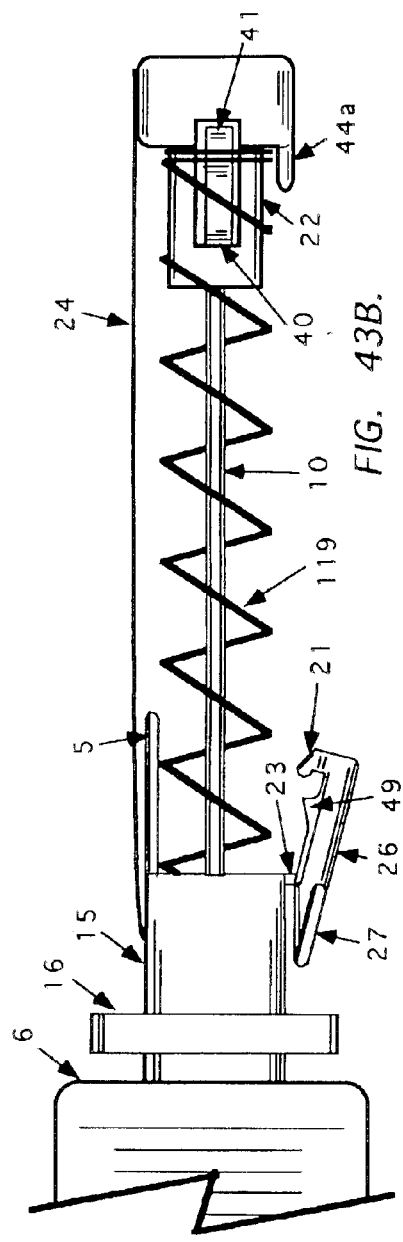
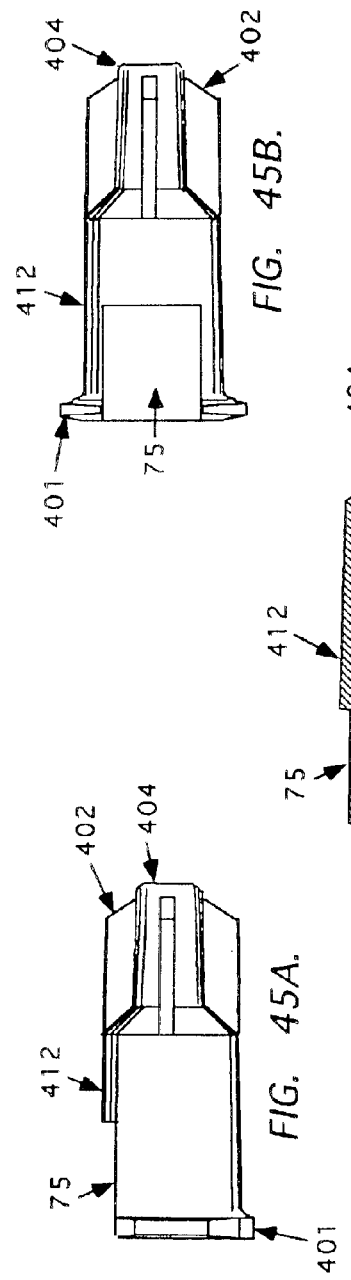
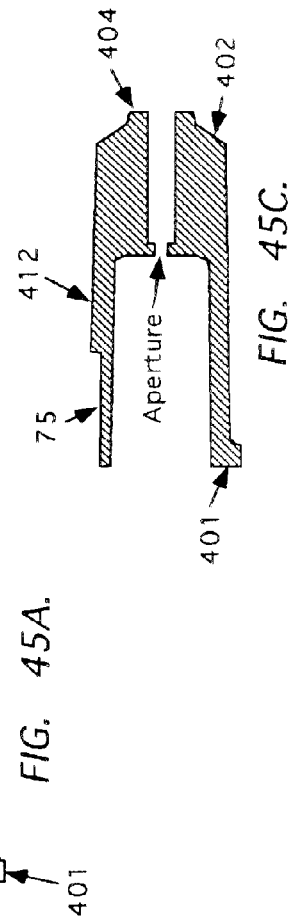
FIG. 43B.
FIG. 45A.
FIG. 45B.
FIG. 45C.

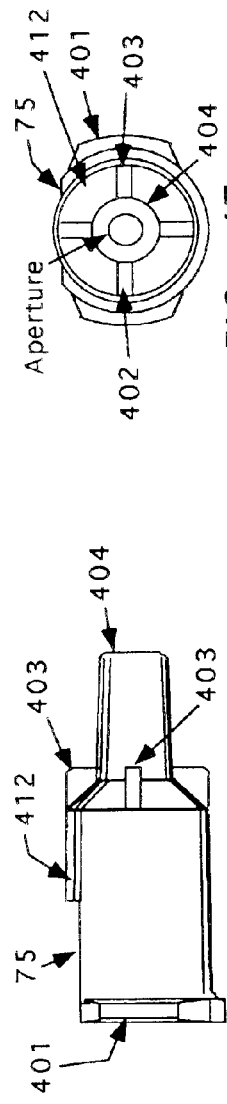
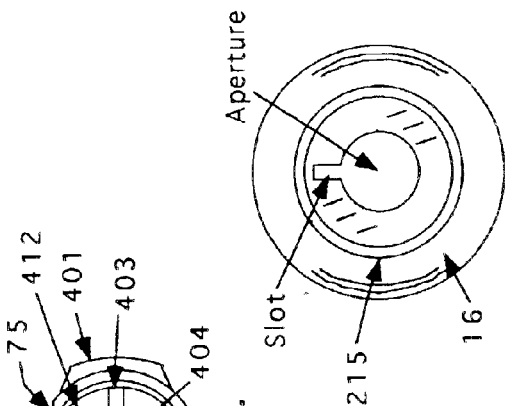
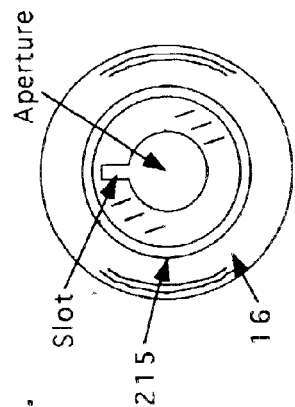
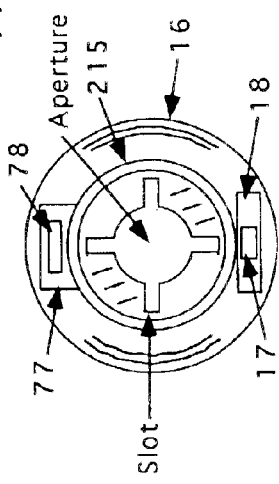
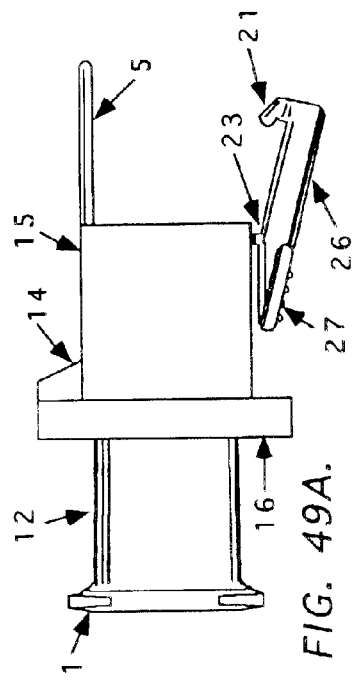
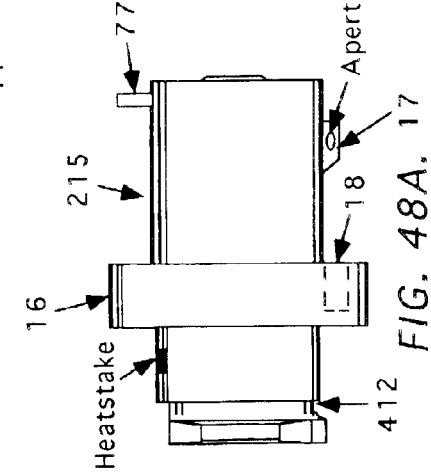

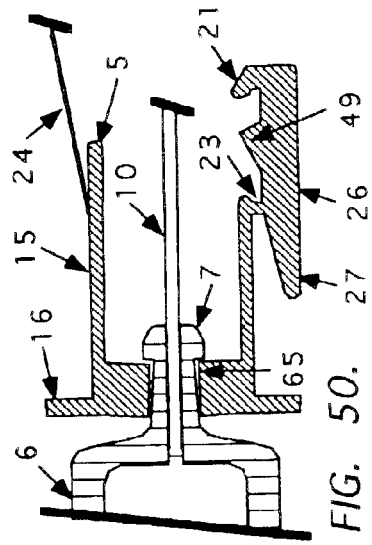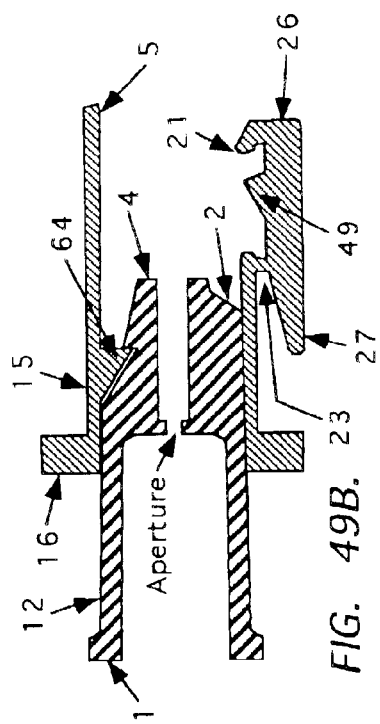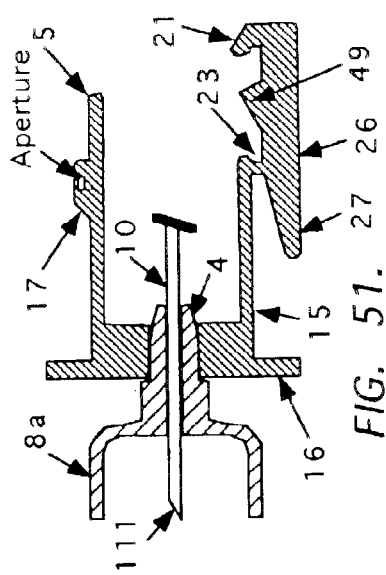

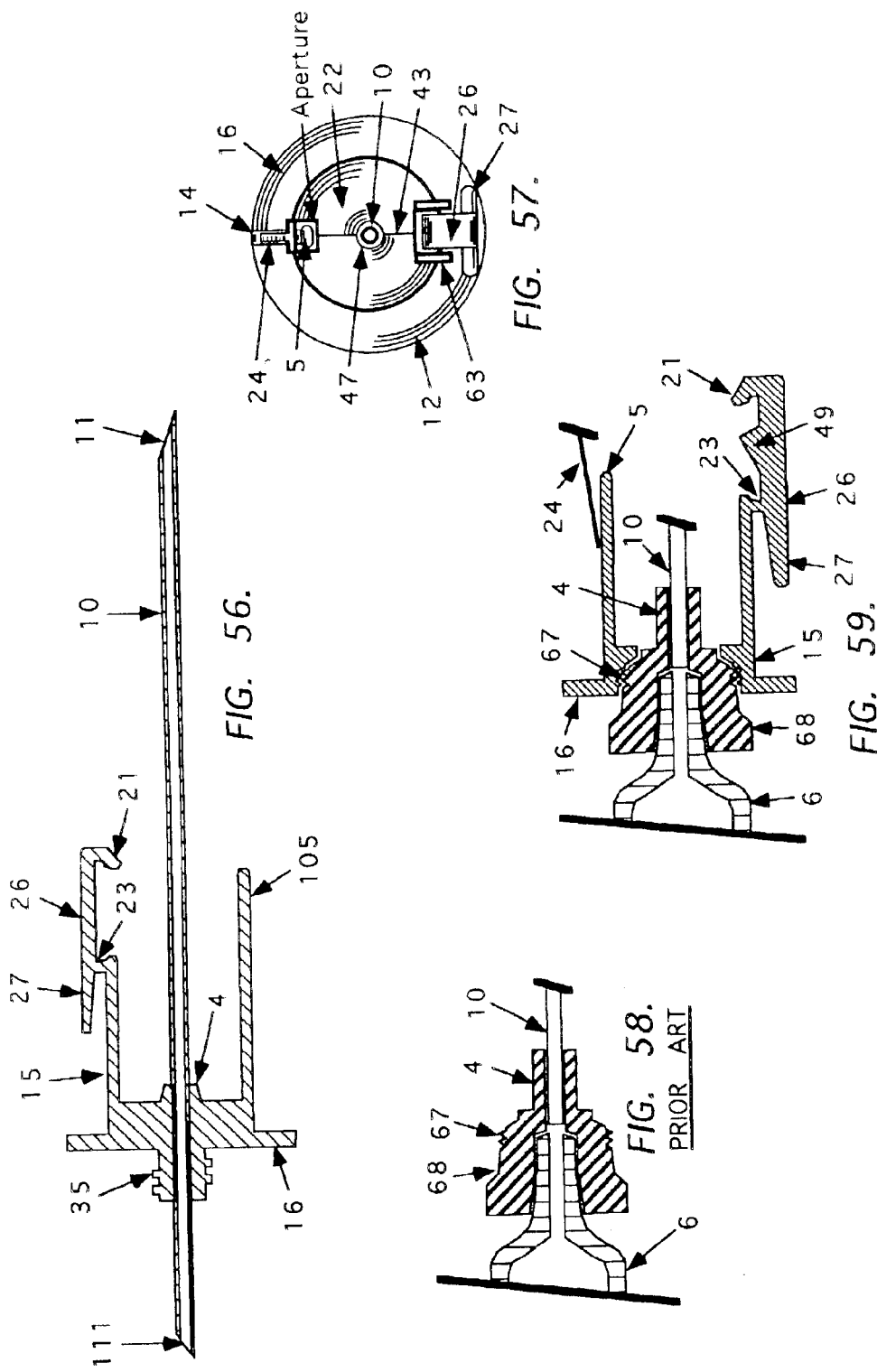

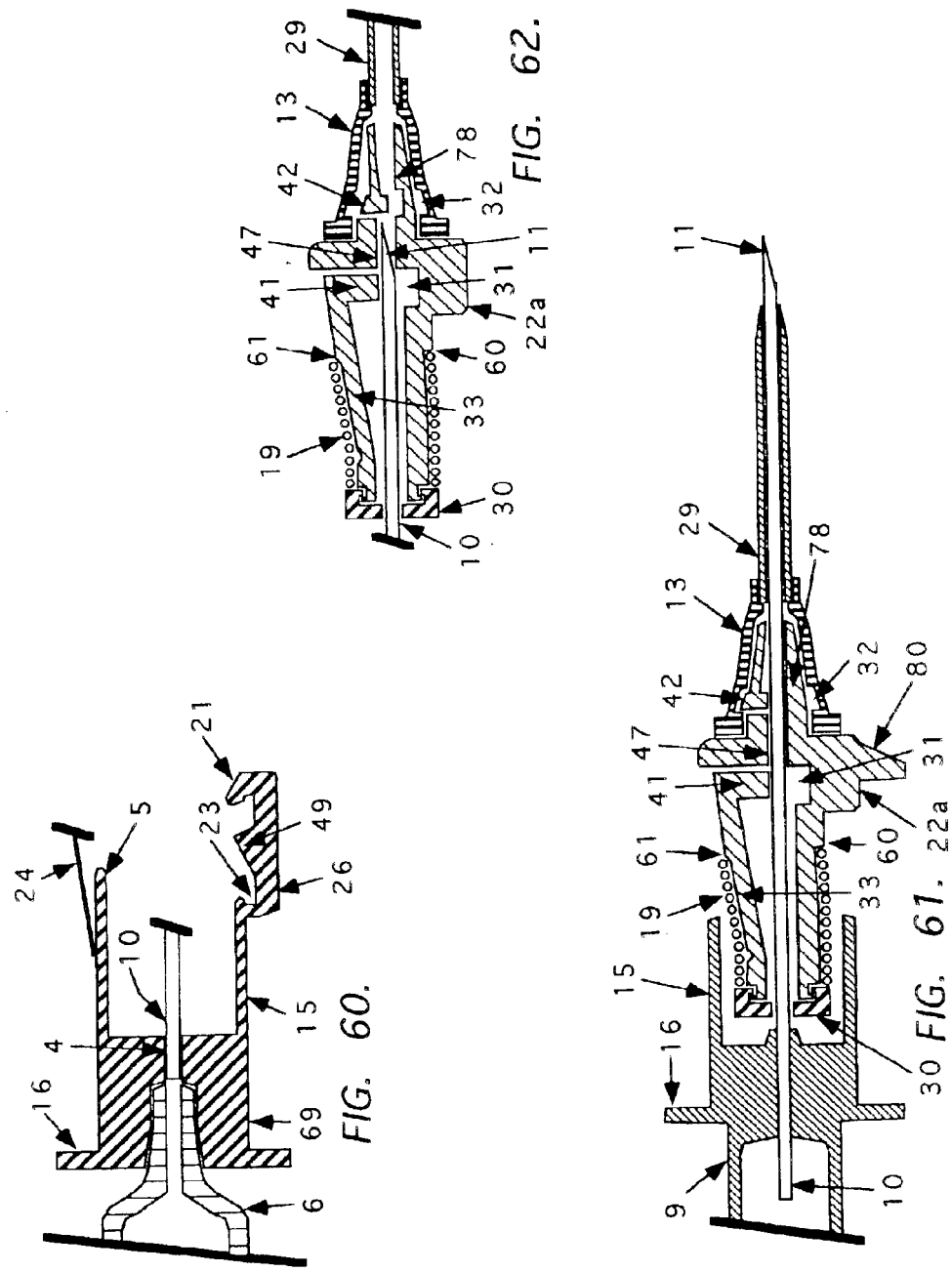

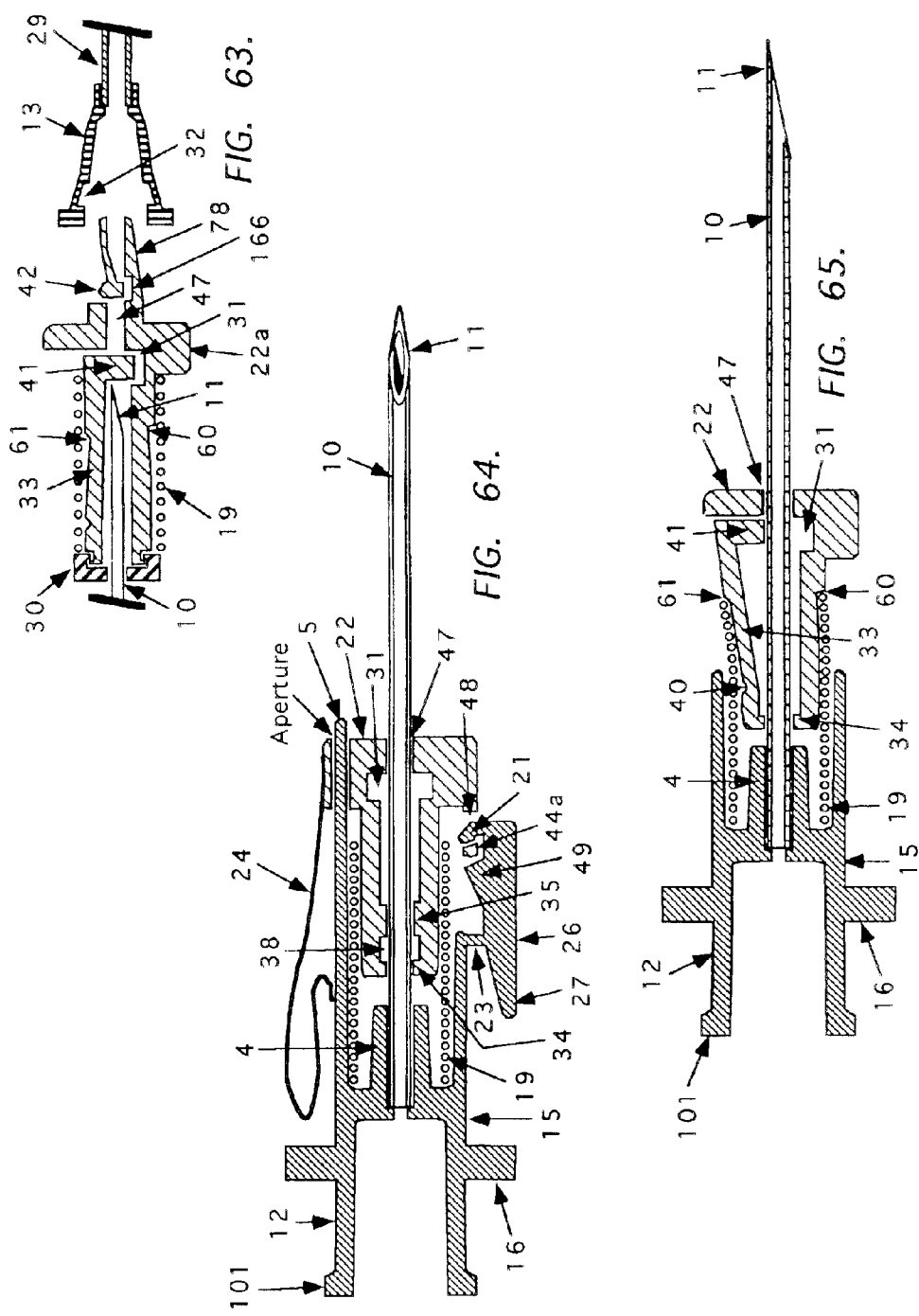

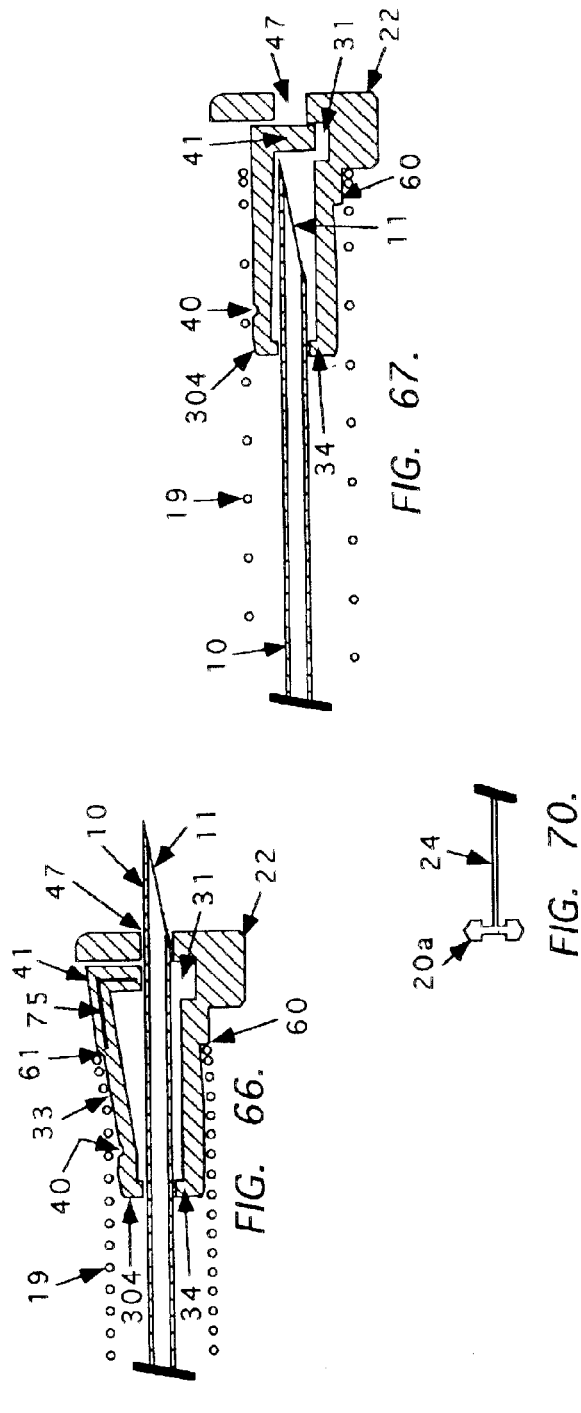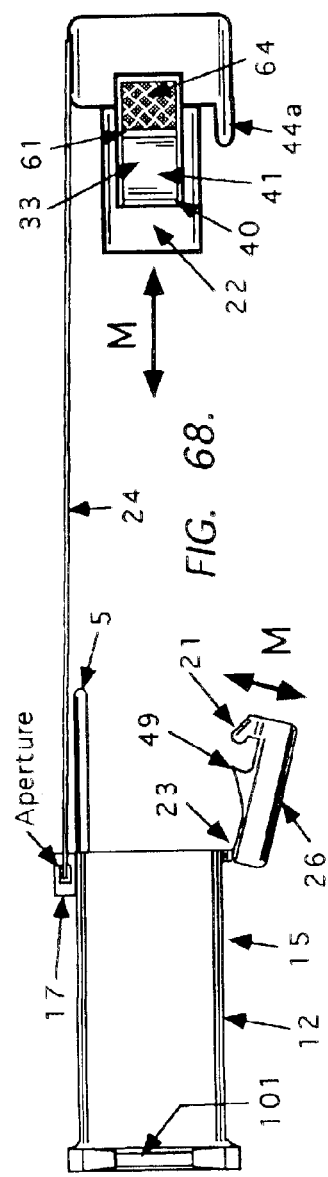

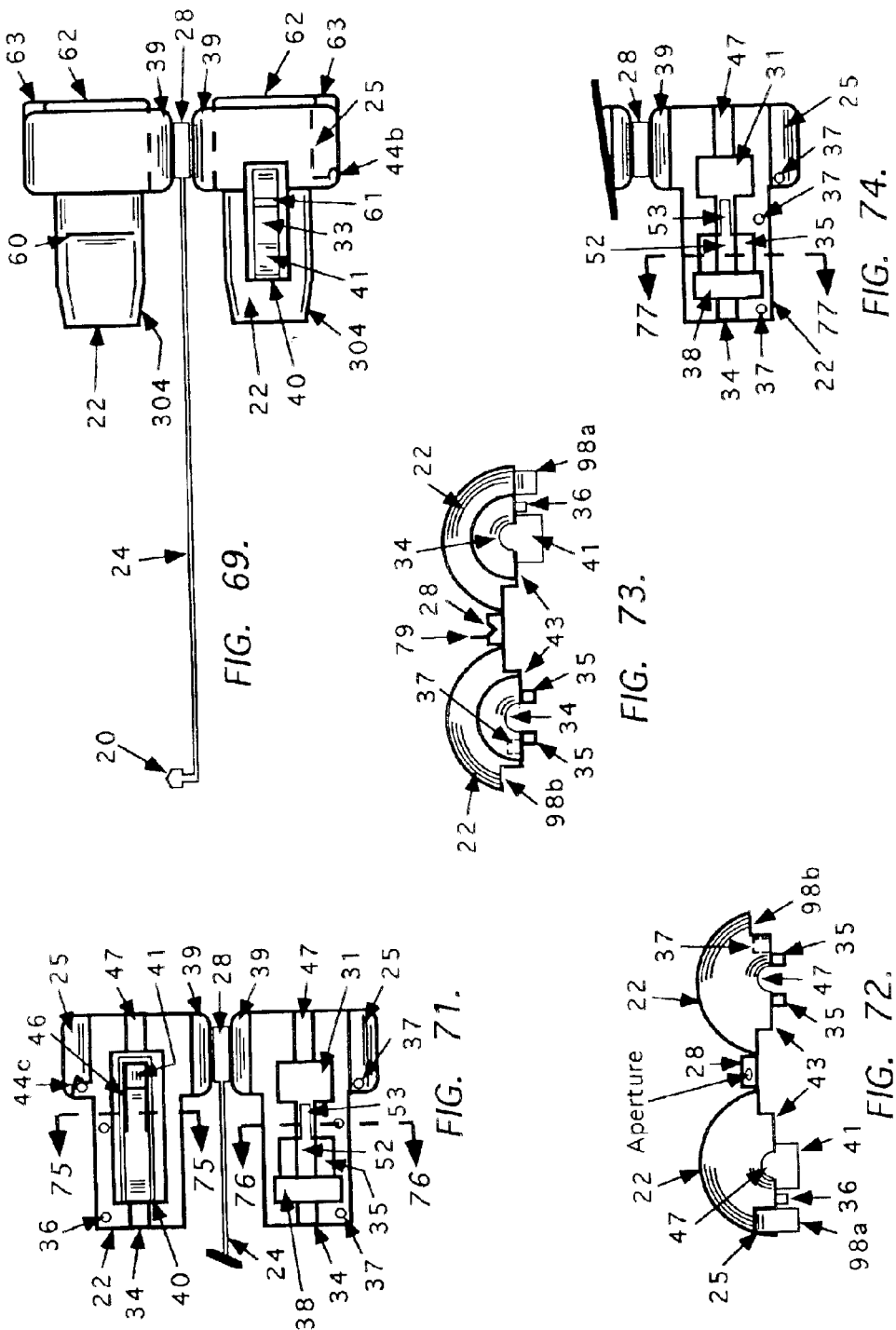

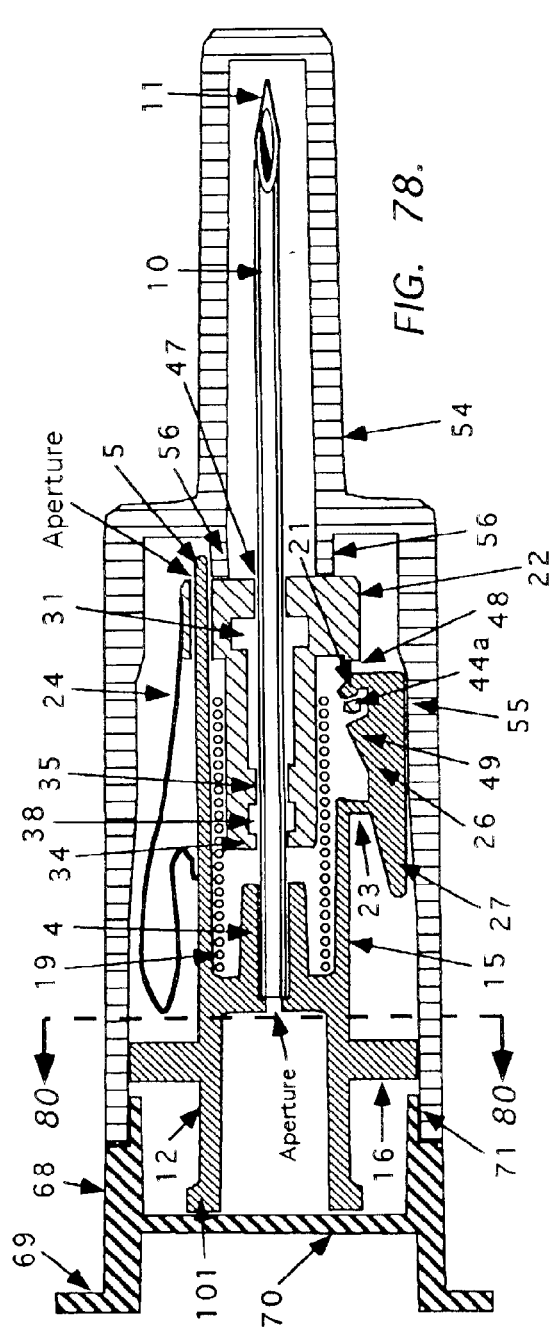
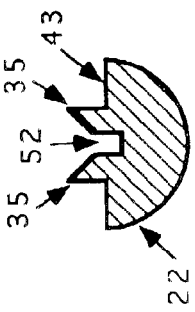
FIG. 77.
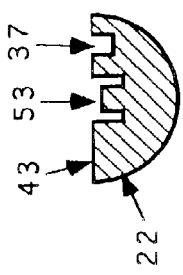
FIG. 76.
FIG. 75.
FIG. 78.

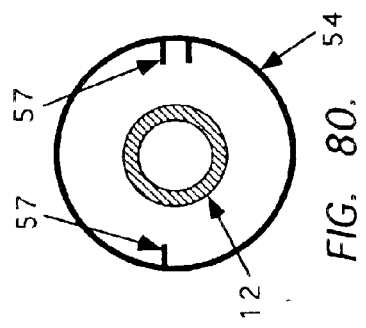
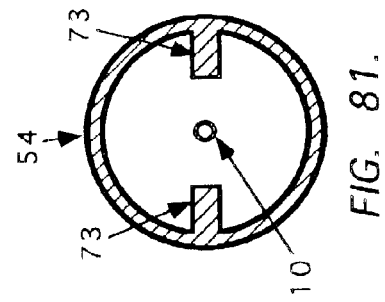
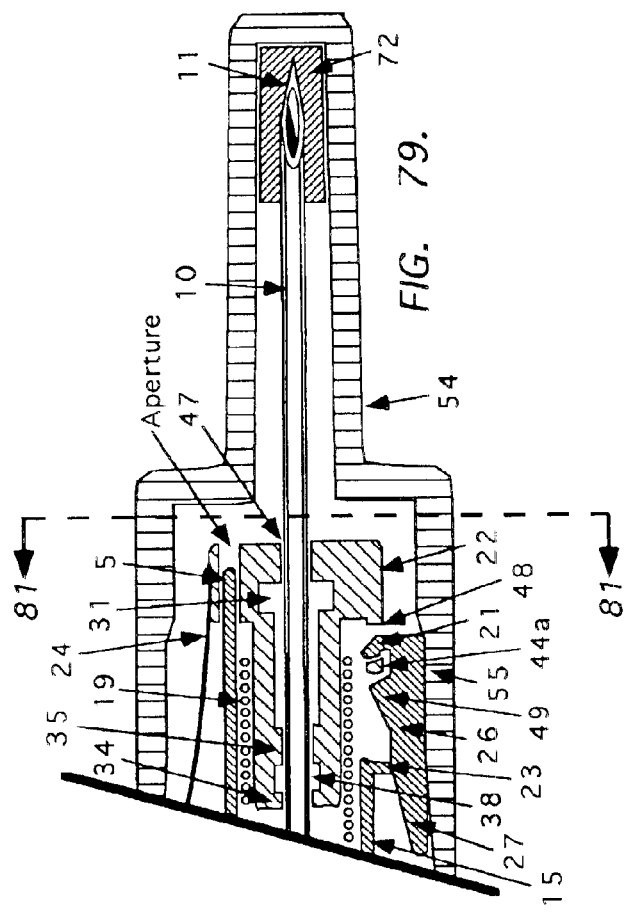
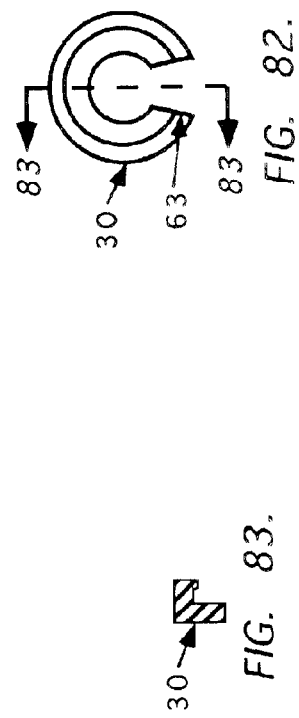
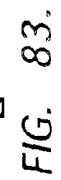

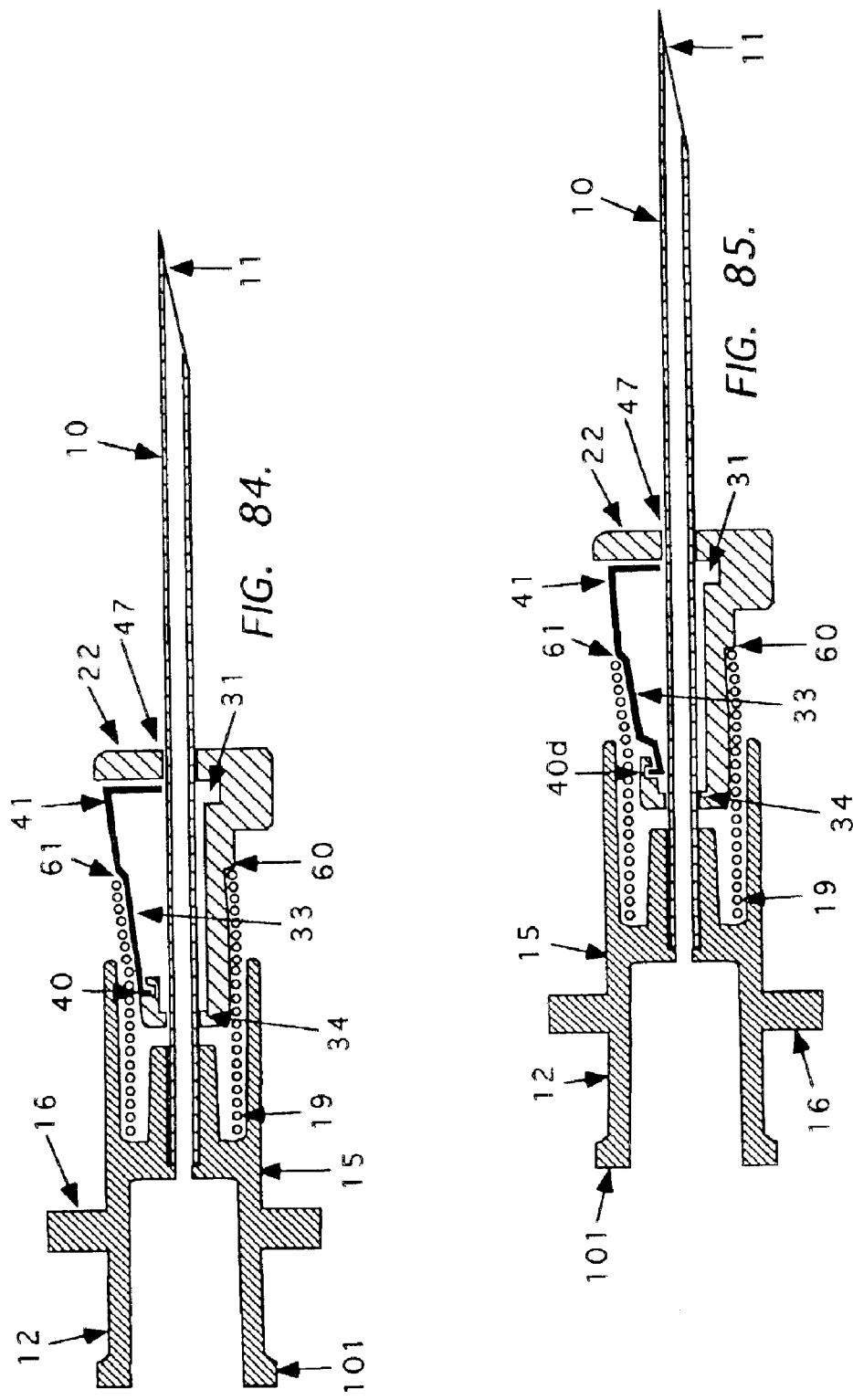

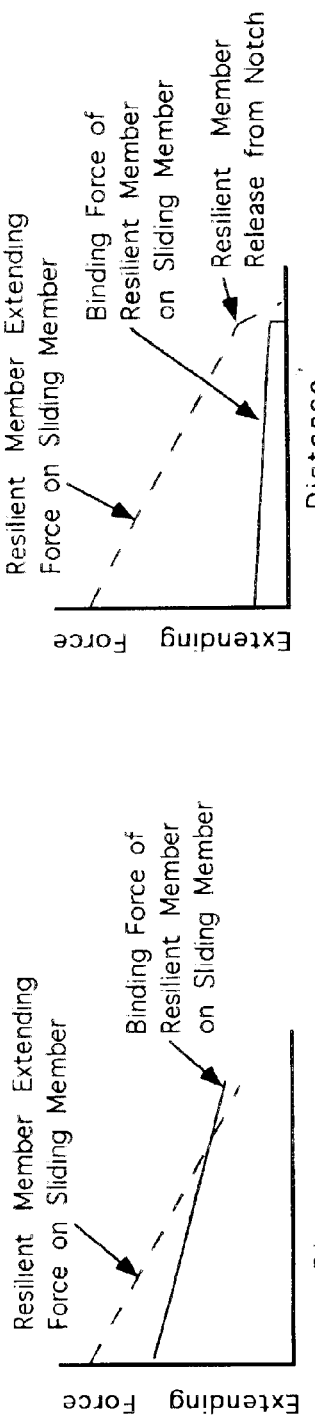
FIG. 86.
FIG. 87.
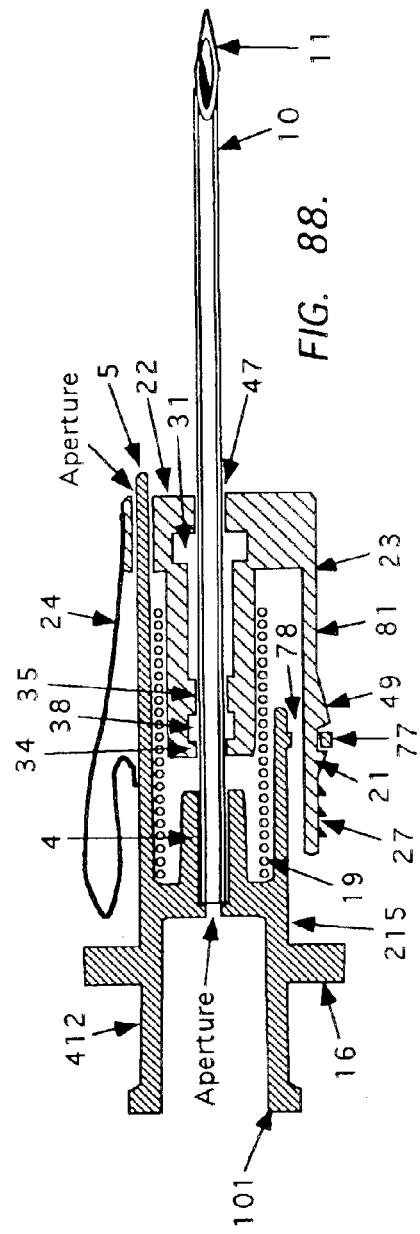
FIG. 88.

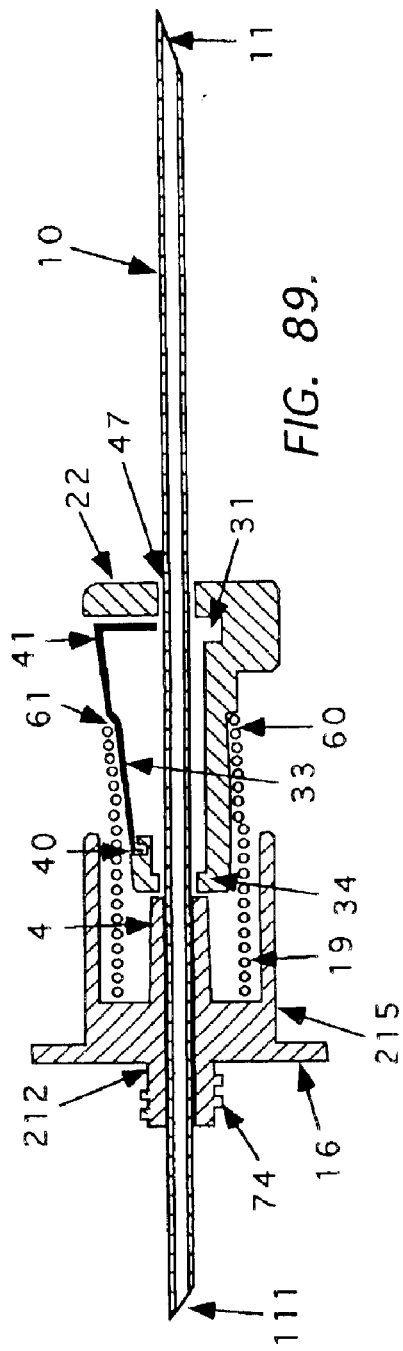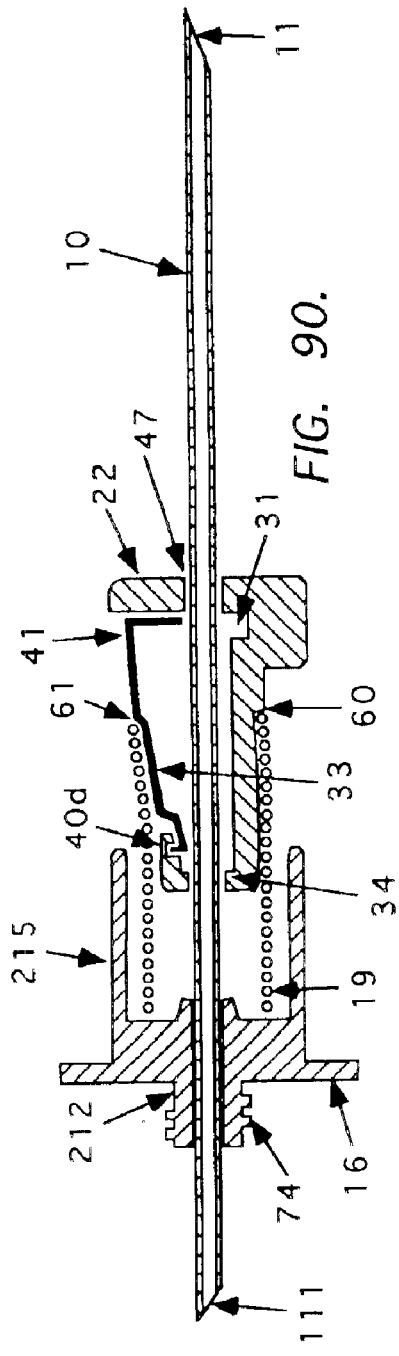

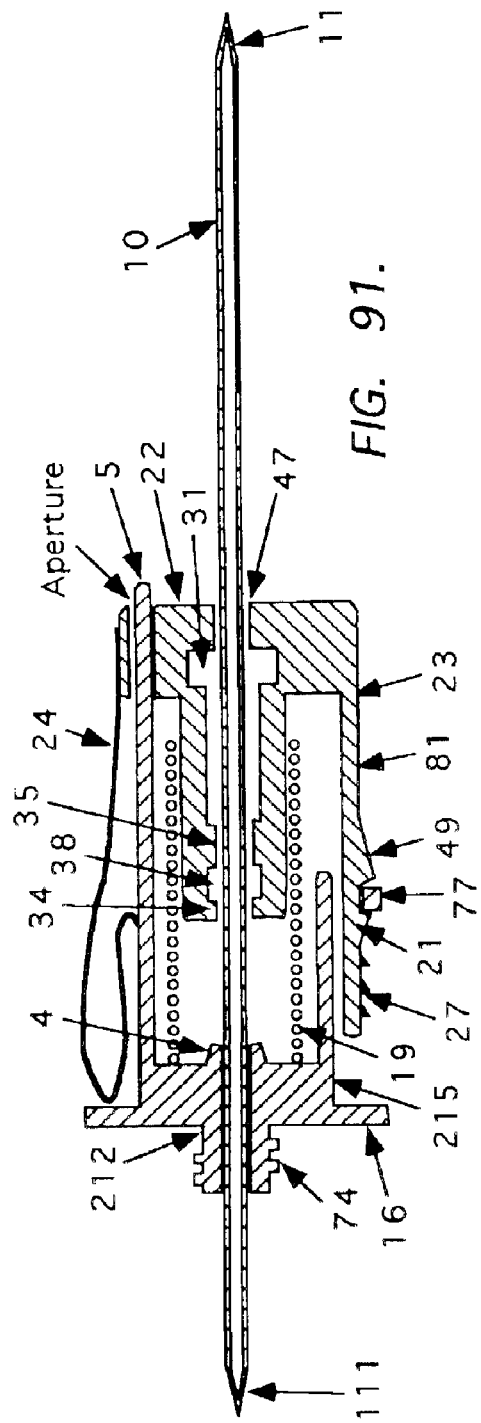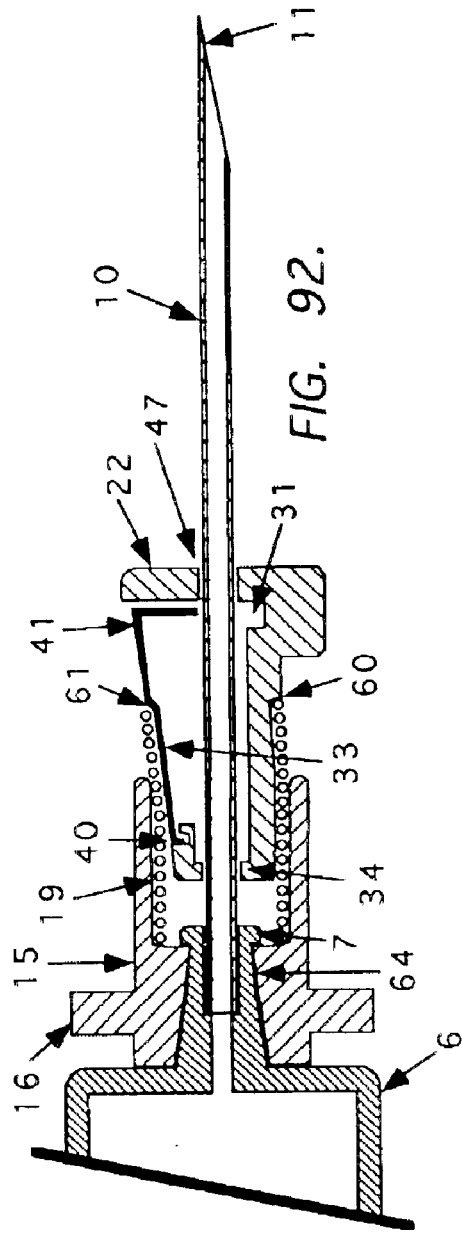

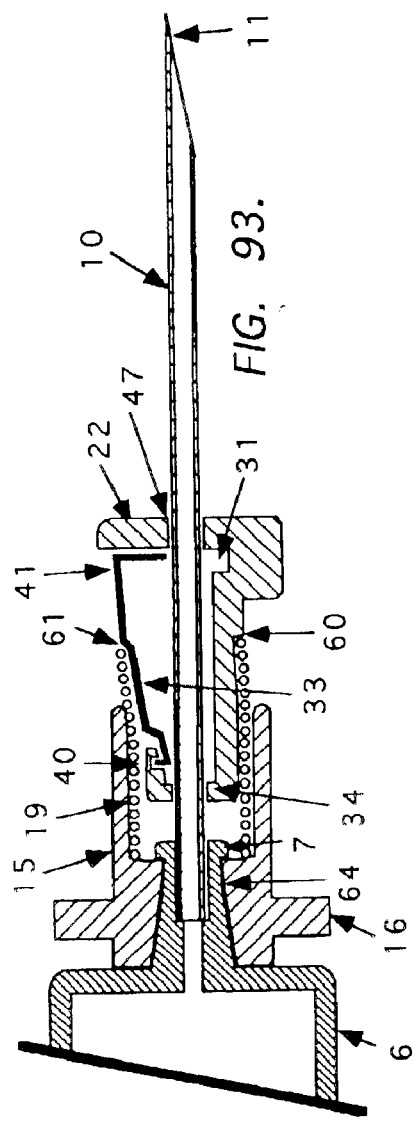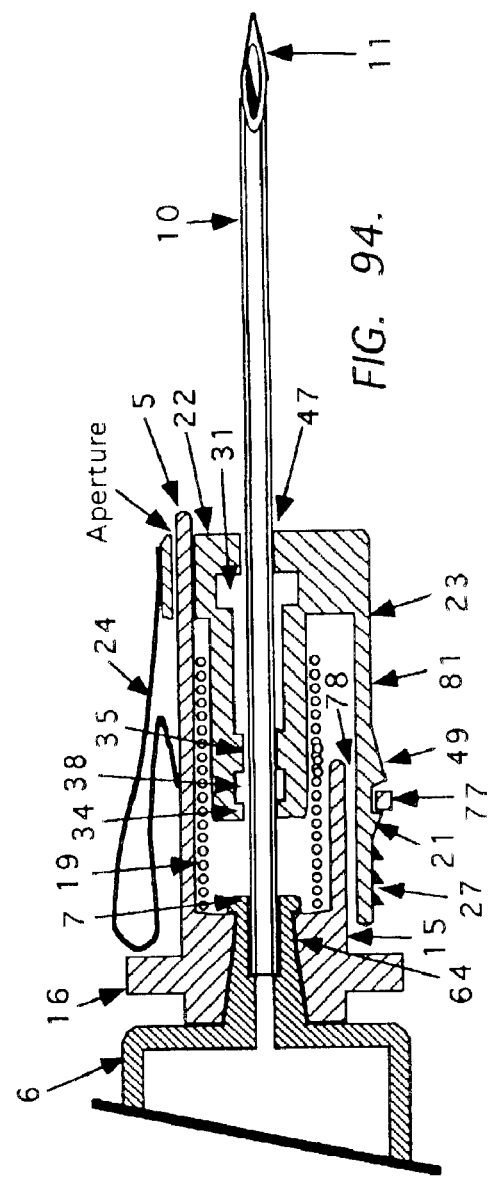

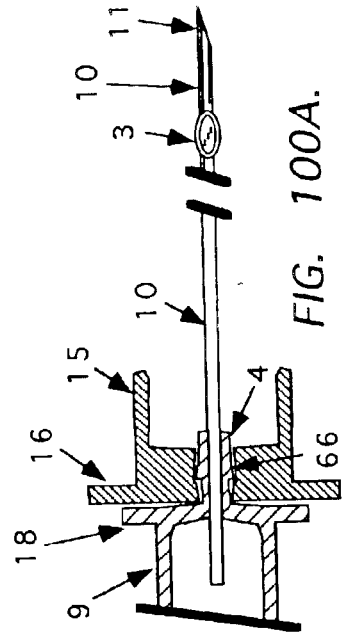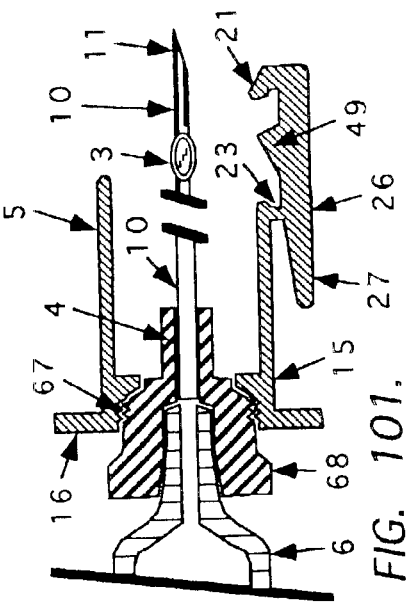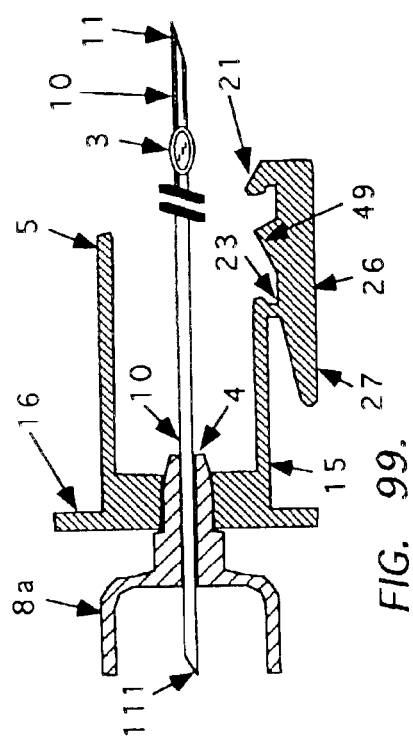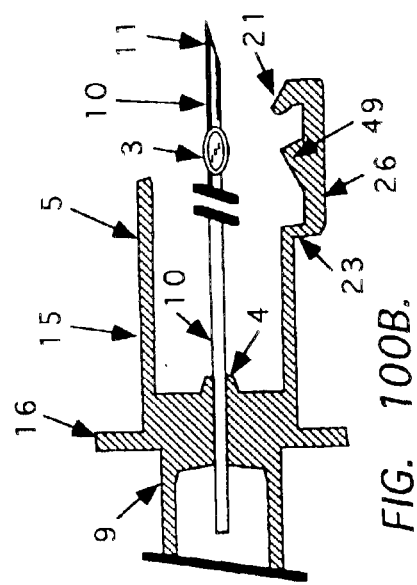

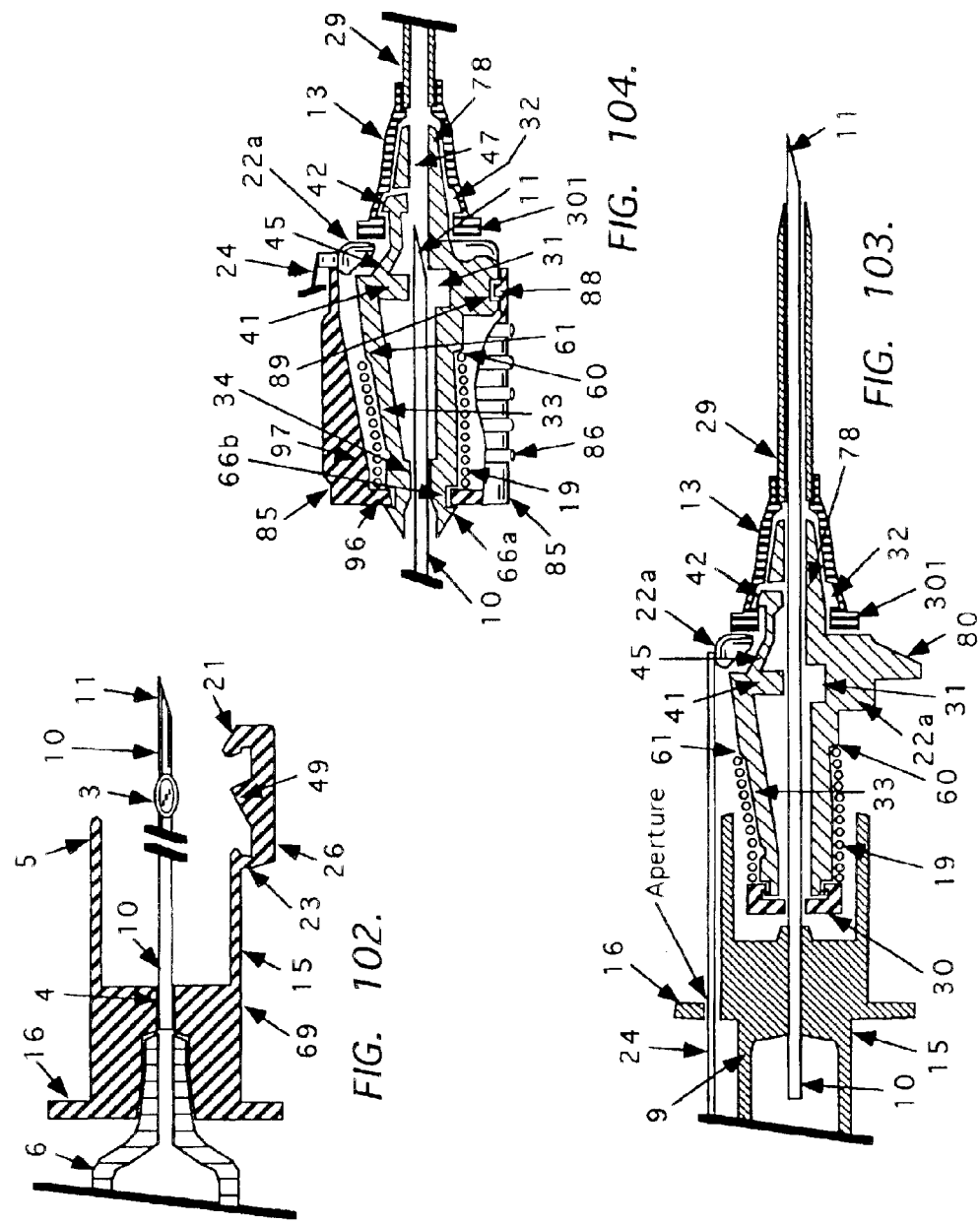

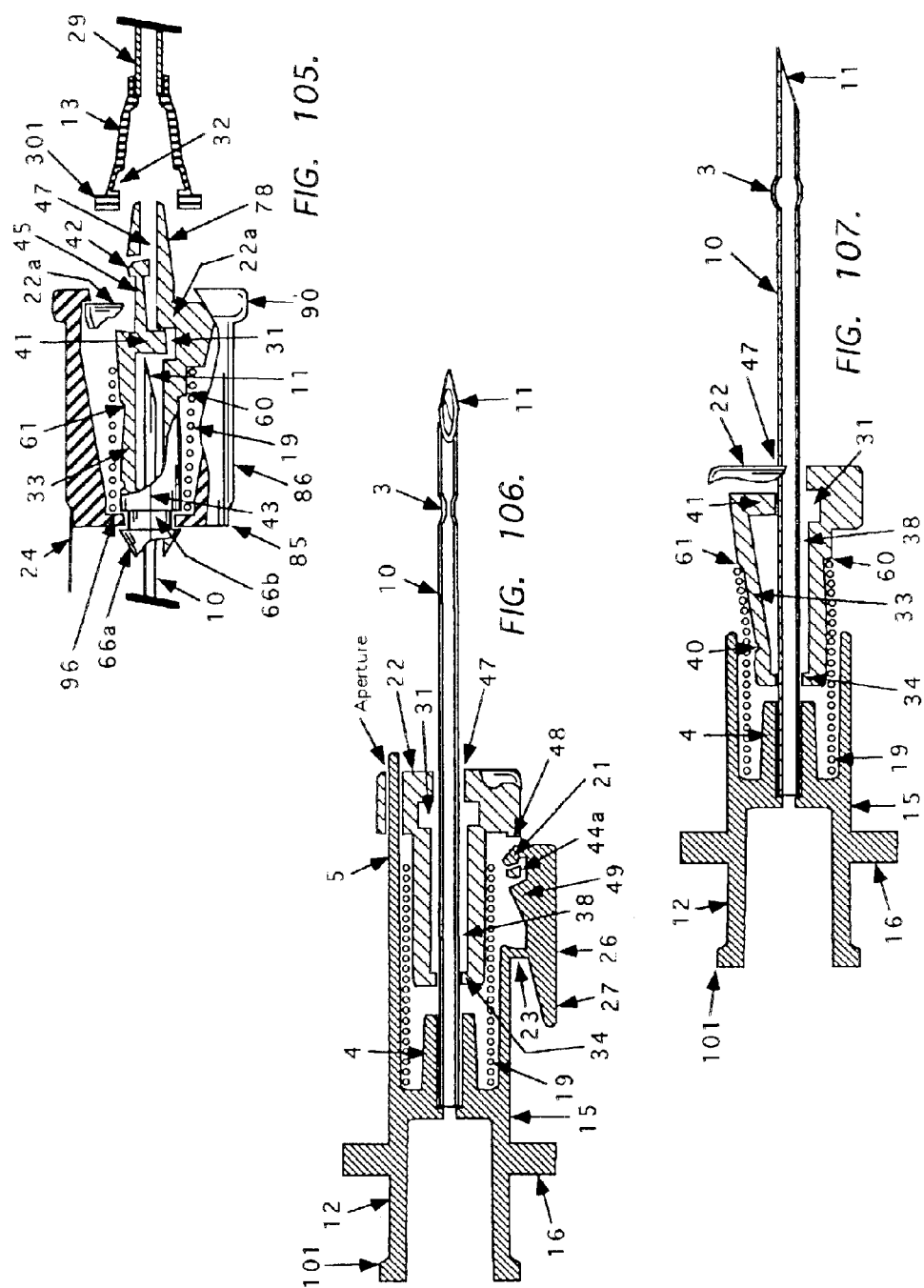

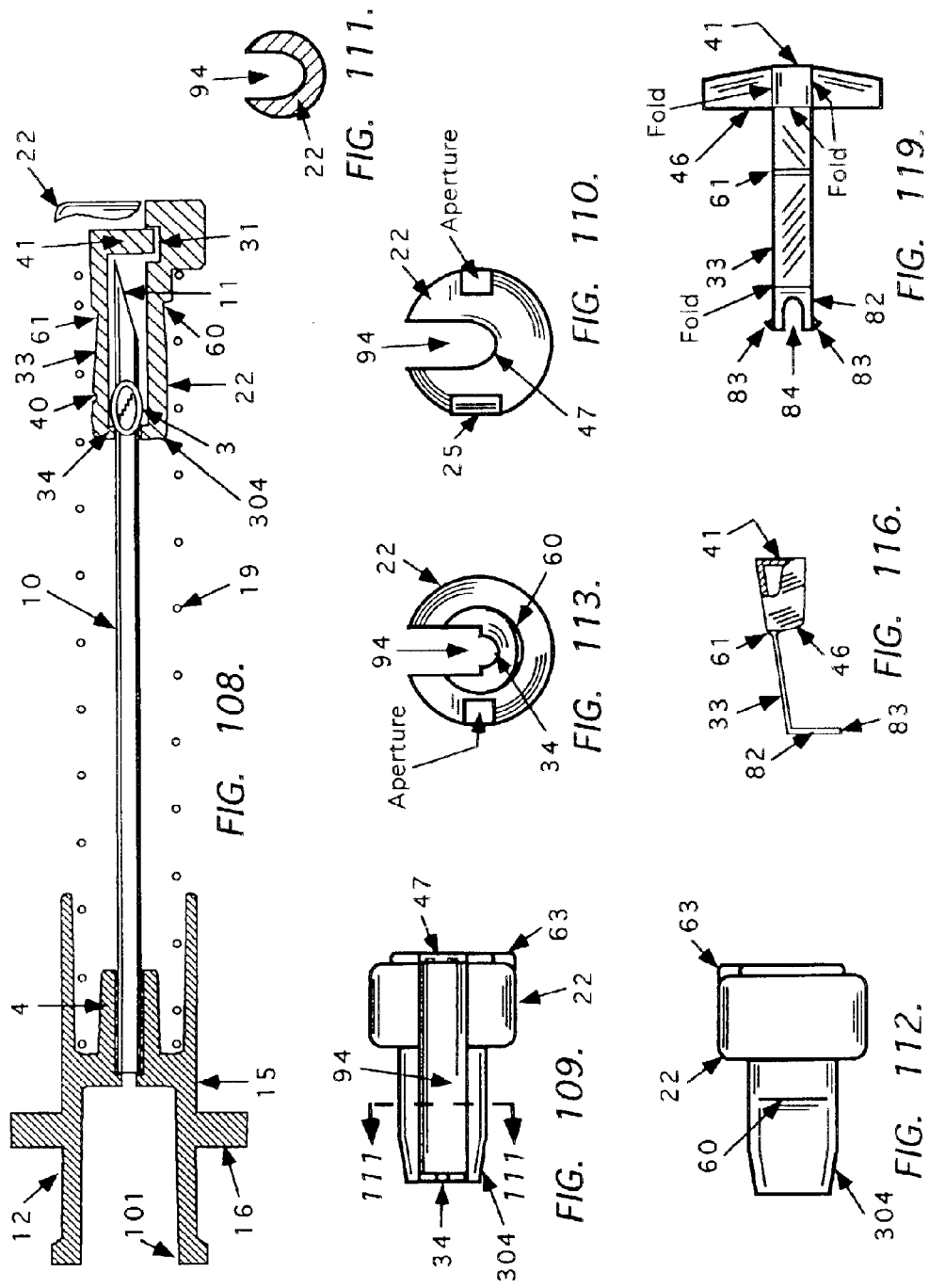

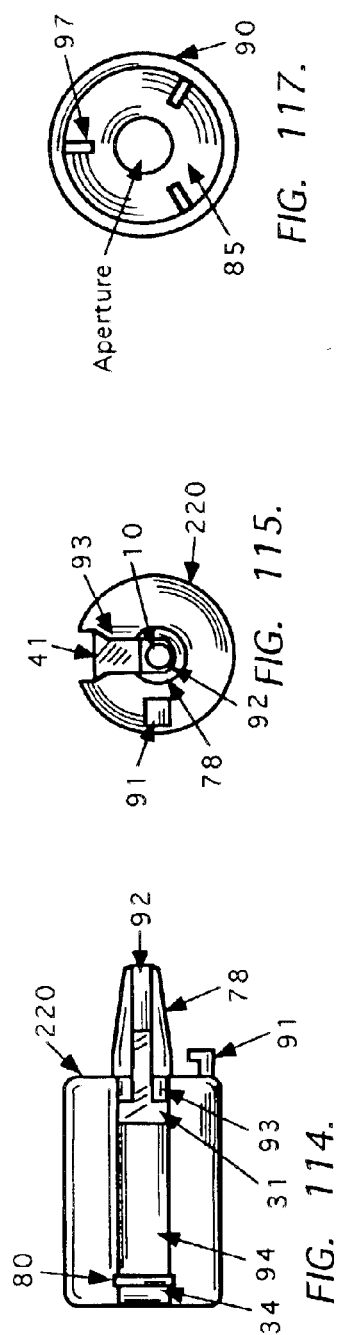

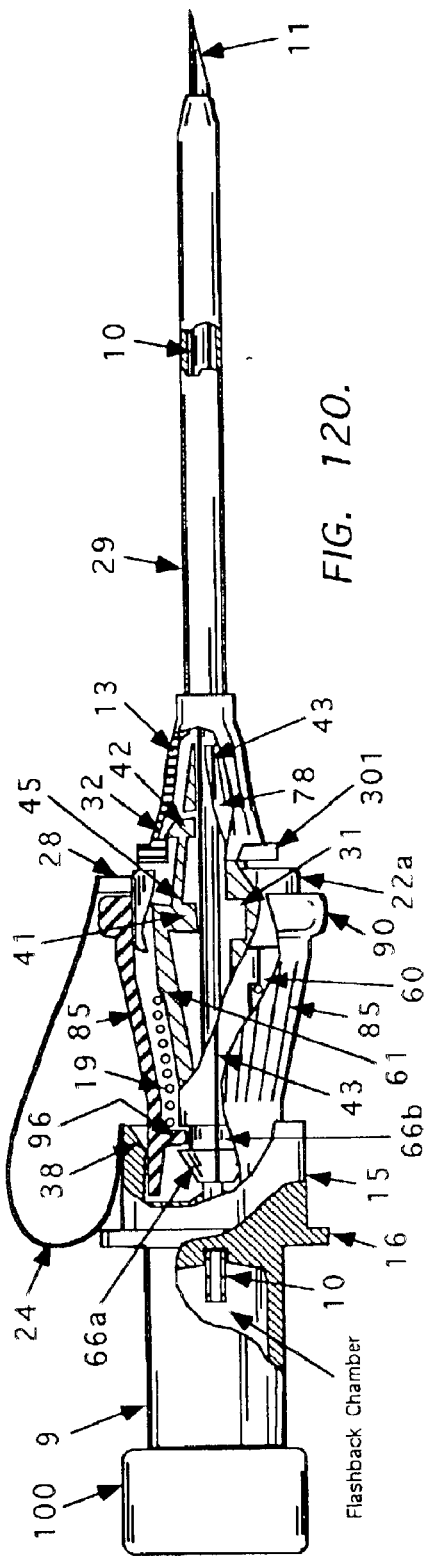
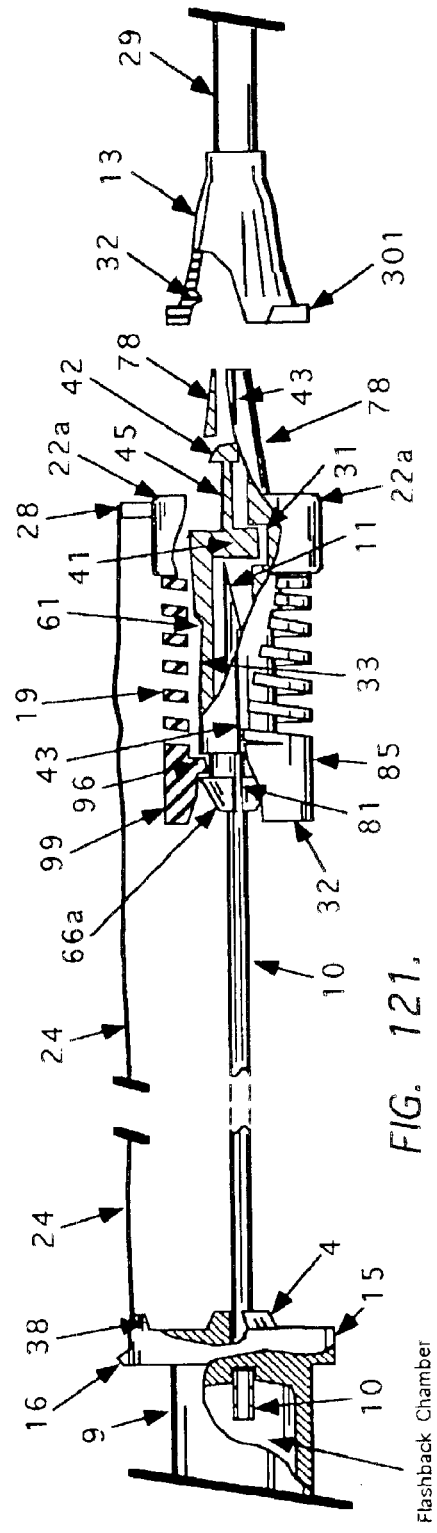
FIG. 120.
FIG. 121.

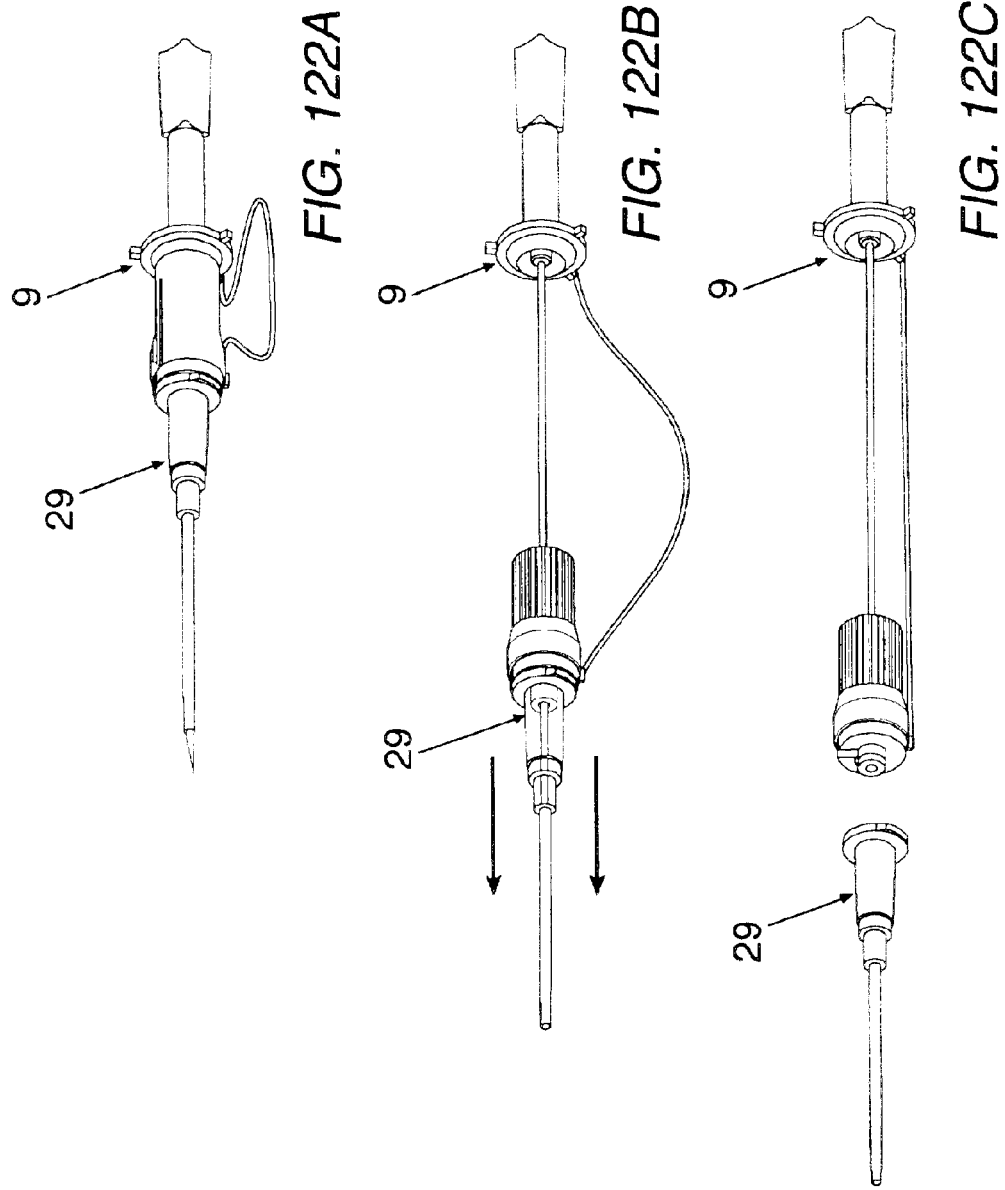

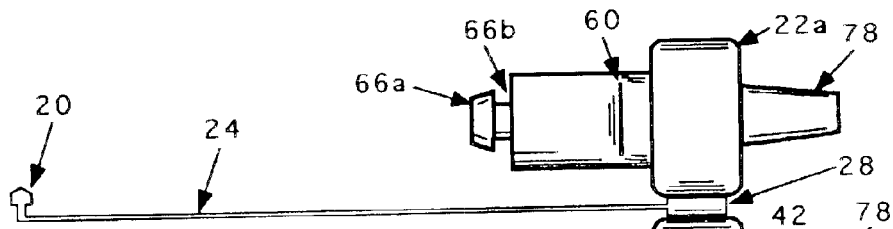
FIG. 125.
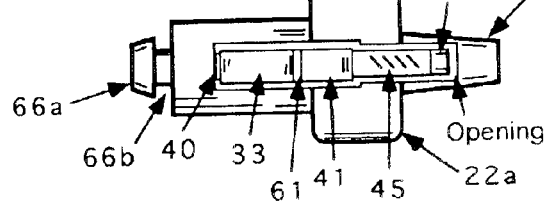
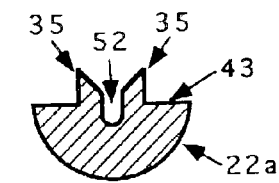
FIG. 129.
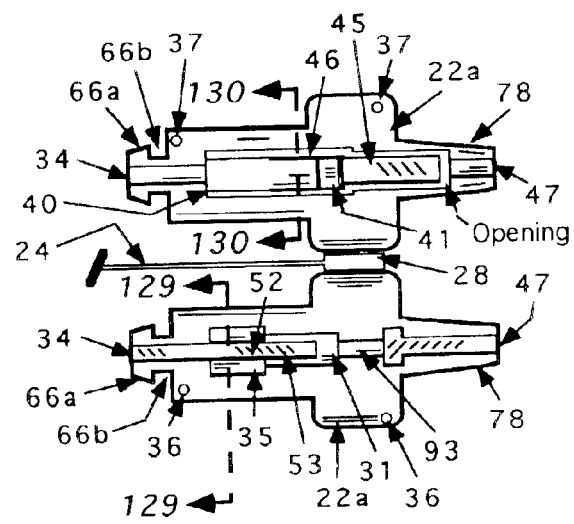
FIG. 126.
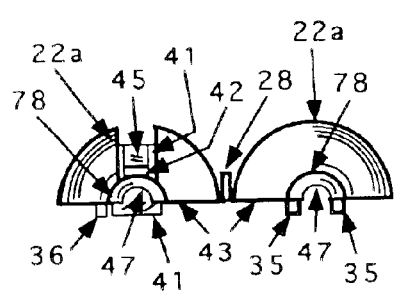
FIG. 127.
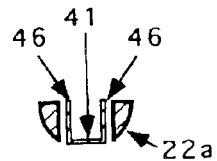
FIG. 130.
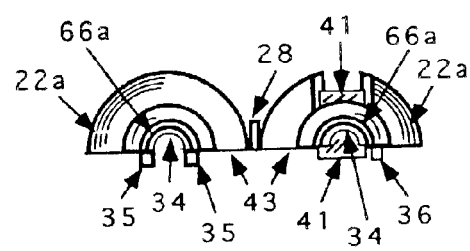
FIG. 128.

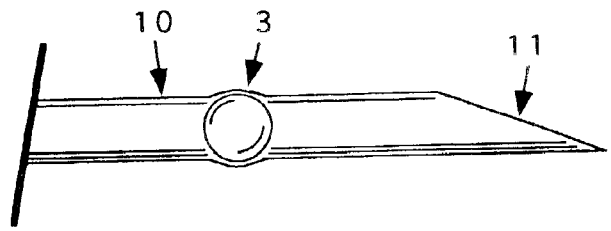
FIG. 131.
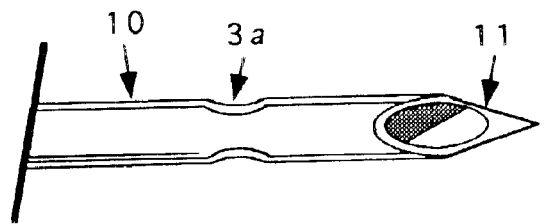
FIG. 132.
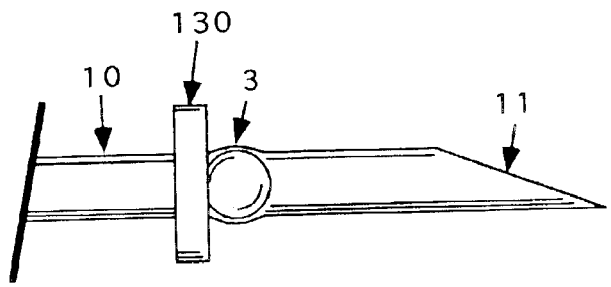
FIG. 133.
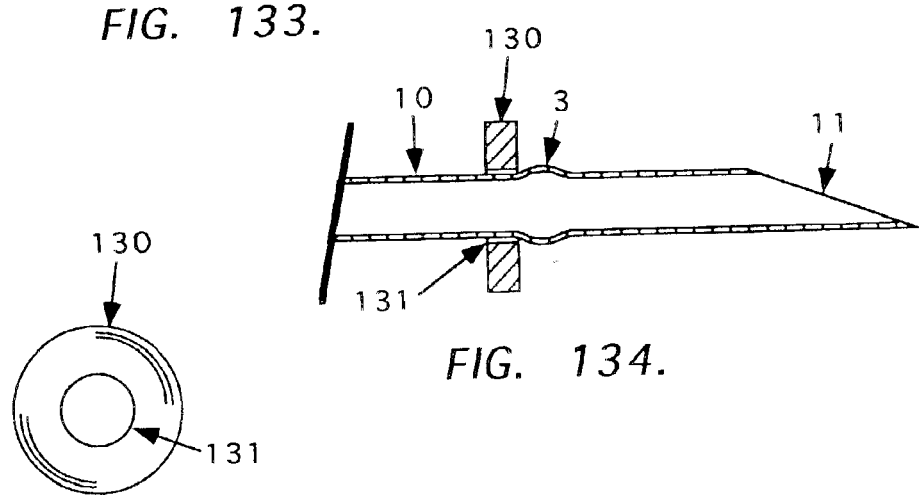
FIG. 134.
FIG. 135.

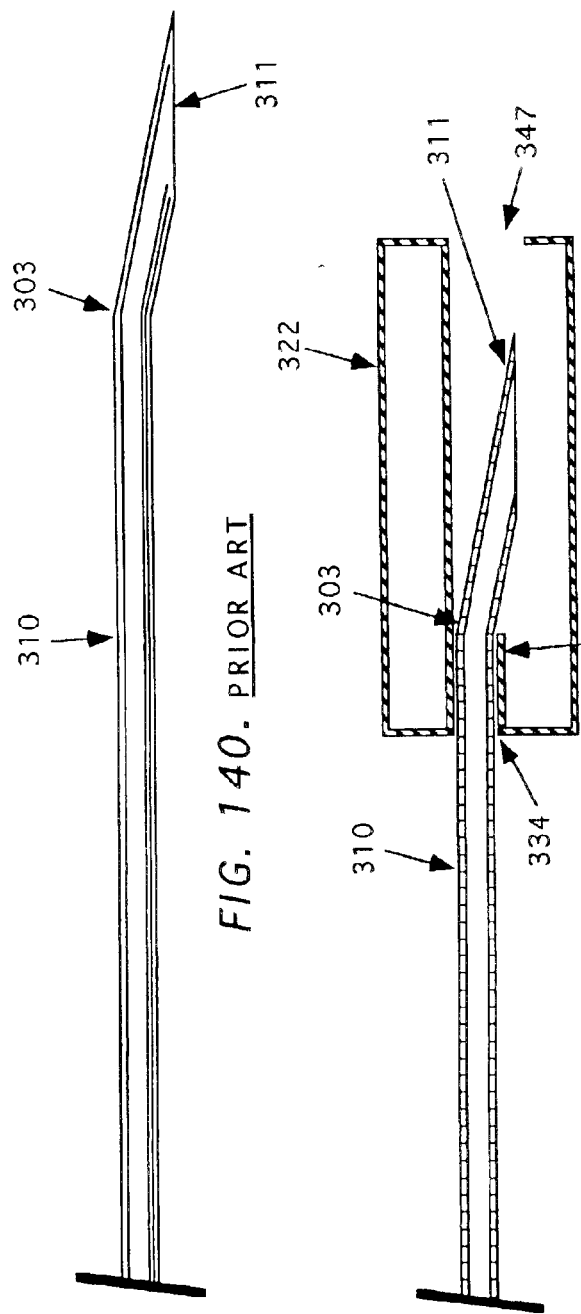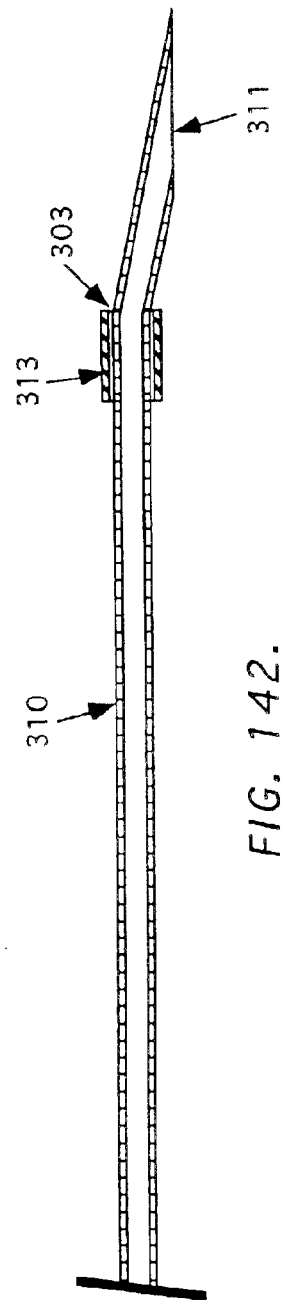

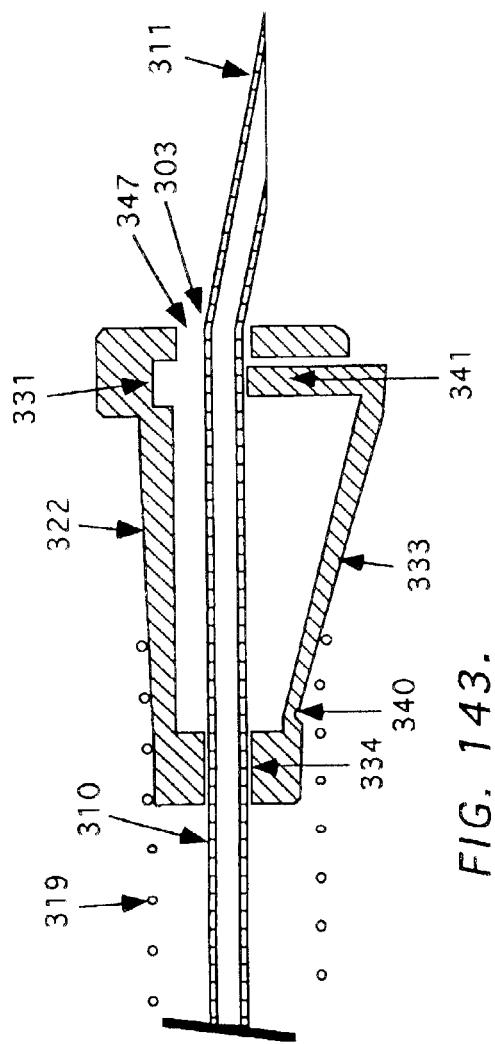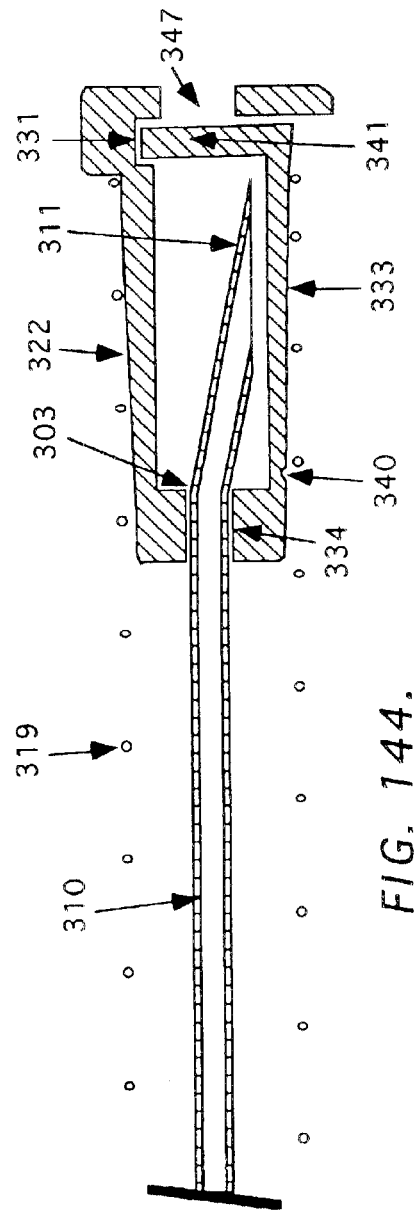
FIG. 143.
FIG. 144.

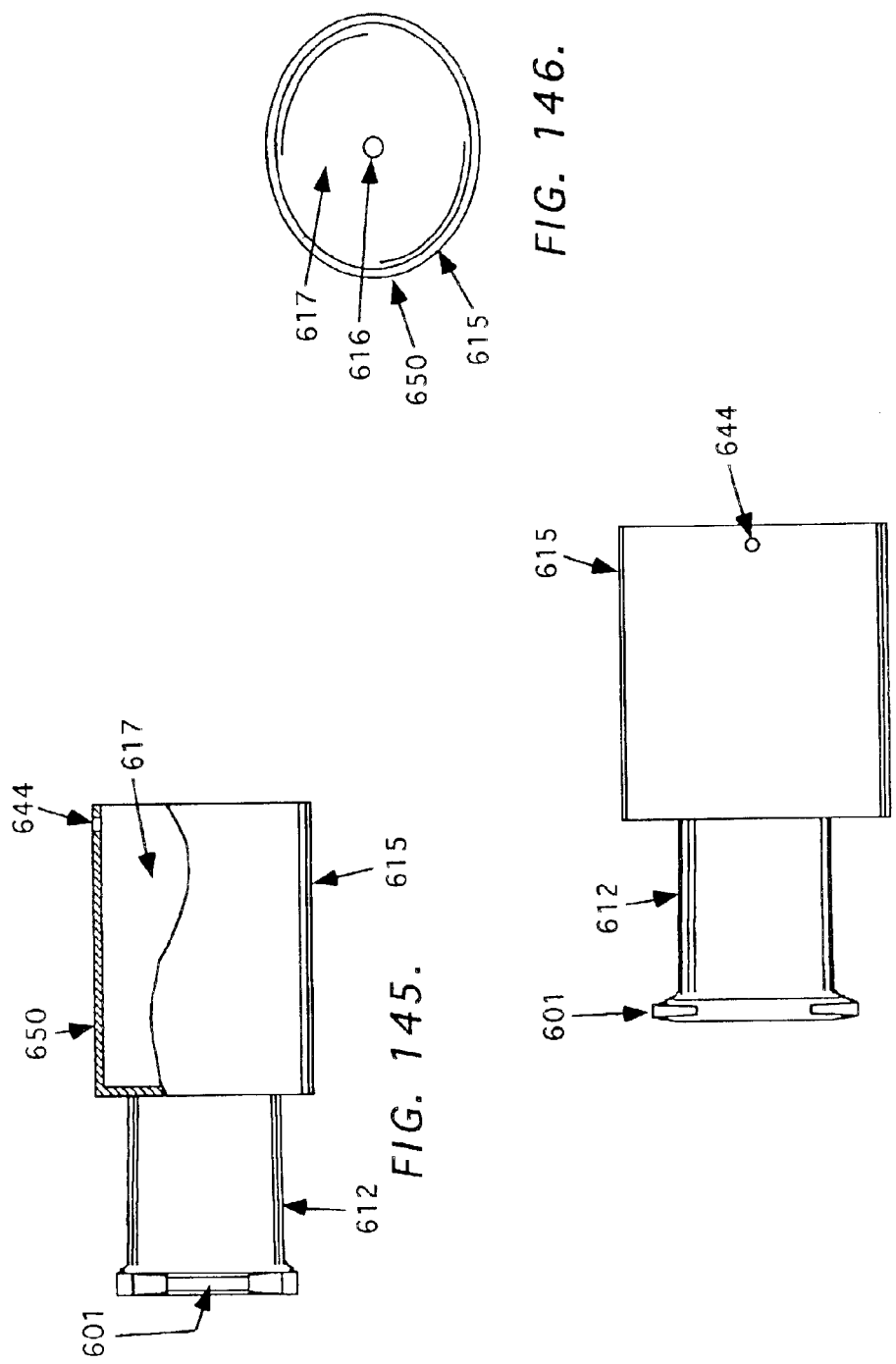

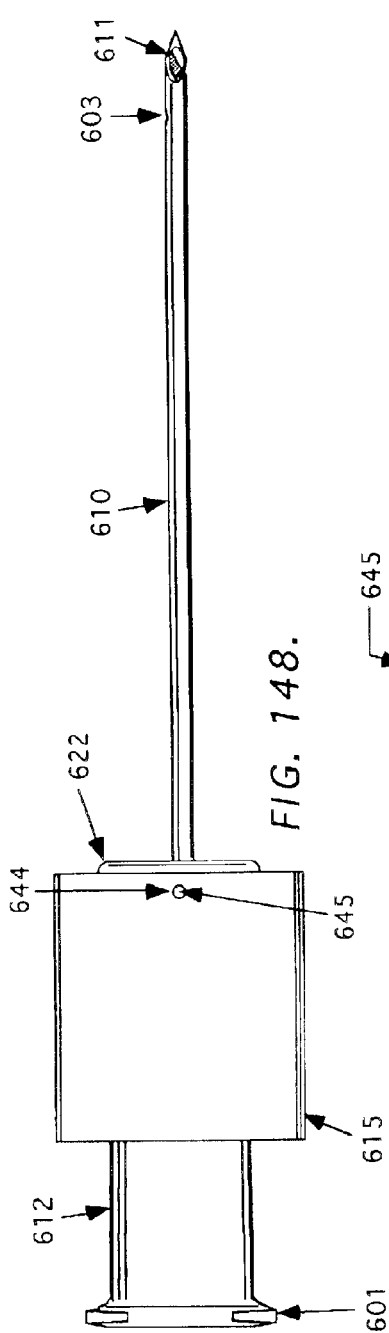
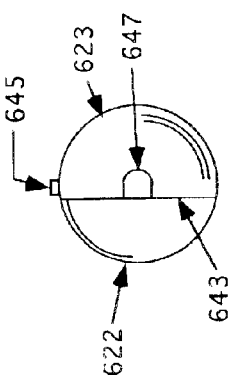
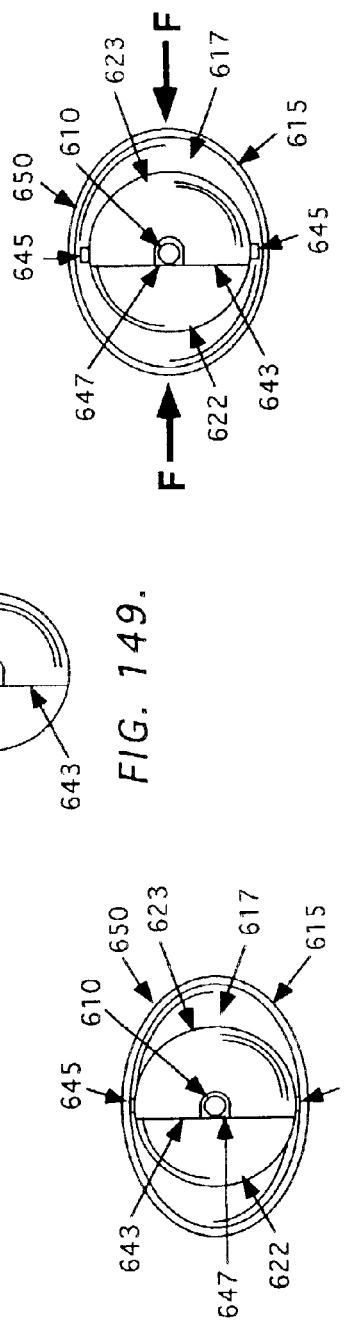
FIG. 148.
FIG. 149.
FIG. 150.
FIG. 151.

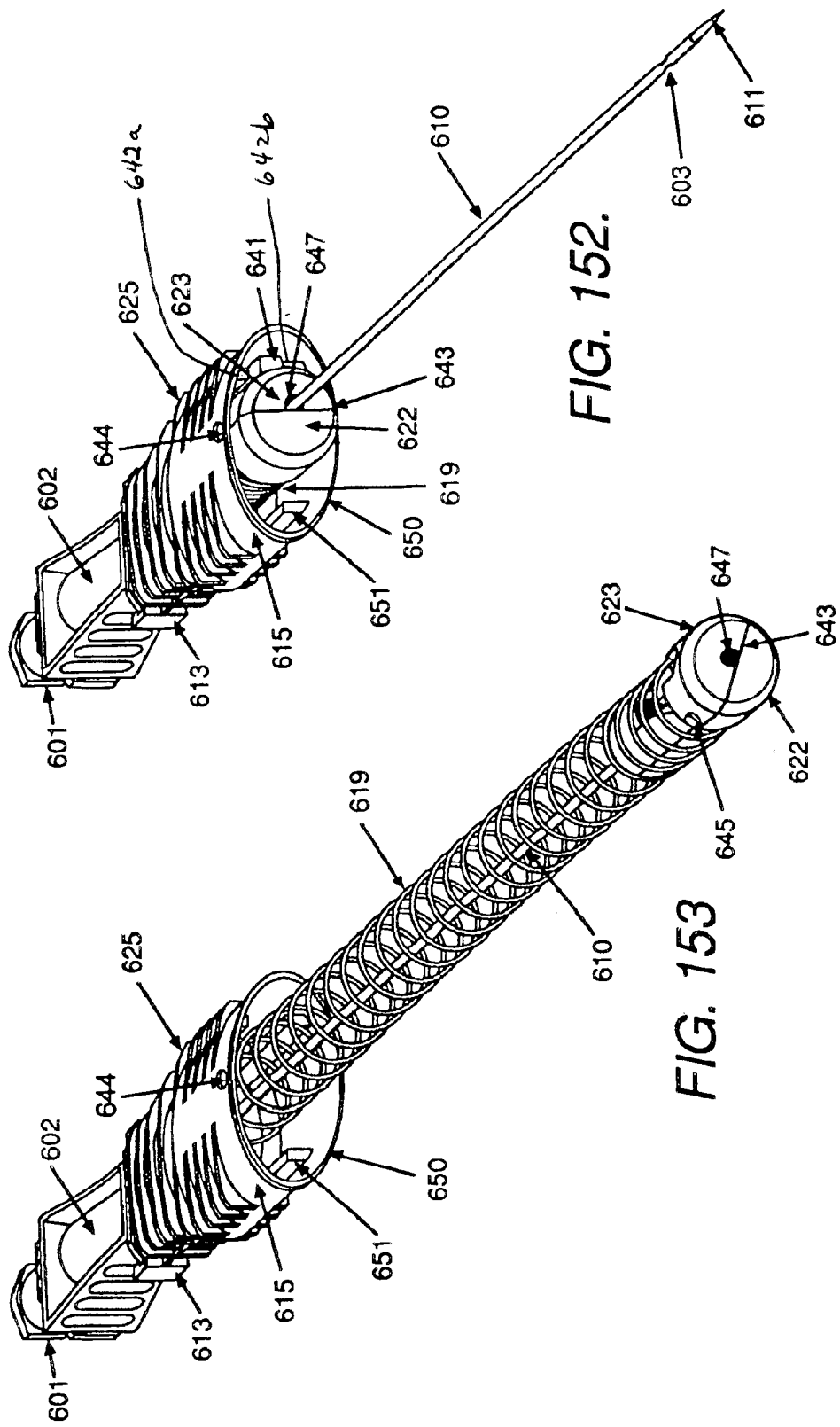

NEEDLE TIP GUARD FOR PERCUTANEOUS ENTRY NEEDLES

This is a continuation of U.S. application Ser. No. 09/846,706, filed Apr. 30, 2001, now U.S. Pat. No. 6,629,959.

CROSS-REFERENCE TO RELATED APPLICATIONS

This application is related to and claims the benefit of filing dates of the following U.S. Non-Provisional patent applications: (1) Ser. No. 60/012,343, entitled PROTECTED HYPODERMIC NEEDLE WITH AUTOMATIC AND MANUAL COVERING MEANS, filed Feb. 27, 1996; (2) Ser. No. 60/025,273, entitled HYPODERMIC DEVICES WITH SAFETY FEATURES, filed Sep. 12, 1996; and (3) Ser. No. 60/031,399, entitled HYPODERMIC DEVICES WITH IMPROVED SAFETY FEATURES, filed Nov. 19, 1996; (4) U.S. patent application Ser. No. 08/807,328 entitled NEEDLE TIP GUARD FOR HYPODERMIC NEEDLES, now issued as U.S. Pat. No. 5,879,337; (5) U.S. patent application Ser. No. 09/172,185 entitled INTRAVENOUS CATHETER ASSEMBLY, now issued as U.S. Pat. No. 6,001,080, filed on Oct. 13, 1998; and U.S. patent application Ser. No. 09/144,398 entitled NEEDLE TIP GUARD FOR HYPODERMIC NEEDLES, filed on Aug. 31, 1998, the teachings of which are expressly incorporated here and by reference.

BACKGROUND OF THE INVENTION

The advent of Human Immunodeficiency Virus (HIV), combined with the increasing incidence of other bloodborne pathogens such as Hepatitis B Virus (HBV) and Hepatitis C Virus (HCV), present healthcare workers with an occupational hazard unprecedented in modern medicine. The risk of contracting HIV from a needlestick injury is approximately 1 in 250, but for those who contract HIV infection as a result of a needlestick injury the risk becomes 1 in 1. The risk of contracting the more contagious HBV as a result of a needlestick injury ranges from 1 in 6 to 1 in 30.

There are also over twenty more known bloodborne pathogens which are transmitted via blood and bodily fluids. The presence of any of these pathogens in patients poses a risk to healthcare workers when invasive procedures are performed. Infectious diseases are now the third leading cause of death, behind heart disease and cancer, signifying a growing need for safer hypodermic equipment. Ten years ago, infectious diseases were classified as the fifth leading cause of death, they are now ranked third. This increase of infectious disease is attributed mainly to the over-use of antibiotics and the growing availability of re-usable, hollow-bore hypodermic equipment.

As the population of infected individuals increases, more people will be treated by healthcare workers, further increasing the odds of disease transmission from patient to healthcare worker. Also, the use of disposable hypodermic equipment is increasing at approximately 7% per annum. Additionally, a meaningful number of clusters of patient to patient transmission in the healthcare setting has been identified throughout the world. Early data suggests improper infection control techniques contribute directly to this increase: including improper use of hypodermic equipment, multiple-dose medicine vials; and failure to change protective gloves and gear for each new patient.

Recent studies also cite the discovery of significant blood contamination on re-usable blood collection vacuum tube holders which are routinely used to collect blood from different patients. Common practice is to ship one vacuum tube holder with 100 blood collection needles. It is likely that new routes of disease transmission will also be found in the future. Healthcare workers are increasingly at risk to disease transmission and nurses perform the majority of invasive hypodermic procedures, such as injecting medicine, collecting blood and inserting indwelling intravenous (I.V.) catheters. Nurses and other healthcare personnel are routinely injured by the exposed, sharp lancet of the needle after use on a patient. The critical time where a percutaneous injury can occur is from the moment the needle is withdrawn from the patient, or I.V. port, to the time the contaminated needle is safety discarded.

There are approximately 5.6 million workers in the United States (U.S.) whose jobs place them at risk for sustaining an accidental needlestick injury. Medical literature cites approximately one million reported needlestick accidents occur in the U.S. each year, with an additional two-thirds believed to be unreported. One million injuries per year translates to a needlestick injury, on average, every thirty-two seconds. Prior to the proliferation of HIV and serum hepatitis, a needlestick injury was considered a routine part of providing patient care. A needlestick injury now carries a life-threatening consequence and healthcare workers must live with this terror on a daily basis.

Hypodermic needles are used in a wide variety of invasive medical procedures with approximately 12 billion units being consumed on an annual basis. Basically, the great majority of hypodermic needles are intended for a single-use on an individual patient and are provided sterile in a variety of lengths and gauges. Hypodermic needles are normally discarded after a single use into a specially designed, puncture-proof biohazard container.

Hypodermic needles are used in medicine, science, veterinary medicine, the biotechnology and pharmaceutical industries, and also in the chemical industry. Medical and veterinary uses range from injecting medication or diluent into a patient or I.V. port, collecting blood, bodily fluids or specimens from patients and, preparing medication. The biotechnology and pharmaceutical applications mainly involve research where substances, liquids, gases or compounds are injected, mixed or withdrawn through a membrane or barrier into a specimen or controlled field. Chemical industry applications involve injecting or removing substances, liquids, gases or compounds to or from a specimen or controlled field. In each and every instance, whether medical or industrial, exposed needles pose a danger of injuring the user.

In medicine, in addition to the danger of contacting contaminated blood or bodily fluids, highly reactive or toxic substances are used for chemotherapy or therapeutic purposes. In the biotechnology, pharmaceutical and chemical industries, toxic, highly reactive, corrosive materials or substances are combined or withdrawn from a variety of experiments or projects.

Despite all the obvious dangers associated with the use of exposed hypodermics, and the availability of manually activated safety hypodermic devices, unguarded, exposed hypodermic needles still dominate the marketplace. This is due to the common practice in the industry where exposed hypodermic needles are sold at discounted prices and usually come packaged with other medical equipment and supplies. Medical institutions continue to purchase exposed hypodermics in this fashion simply for economic reasons.

The basic problem with many of the present day safety hypodermic devices is that they are meant to be manually activated, or in the language of the medical device industry, they are considered "active" devices. They may have safety shields, retractable needles, moveable sheaths or the like; but they generally require the user to complete another procedure to facilitate engagement of the safety mechanism. Although there are a number of retractable needle into syringe devices available, the manufacturing costs associated with these devices are prohibitively high.

What is needed is a low-cost safety hypodermic apparatus with a universal application.

BRIEF SUMMARY OF THE INVENTION

It is therefore an object of this invention to provide a needle point guard that effectively shields the sharpened distal tip of the needle after use.

It is another object of this invention to provide a safety hypodermic apparatus which is automatic and/or semi-automatic covering, fail-safe and single-use in nature.

It is another object of this invention to provide a safety hypodermic apparatus which looks similar to a standard, exposed, disposable hypodermic needled device (i.e., the needle and needle tip are exposed prior to performing the hypodermic procedure).

It is another object of this invention to provide a safety hypodermic apparatus which conforms to existing procedures for aspirating medication into a syringe, administering injections, and allowing unrestricted access for vascular access or catheter insertion.

It is yet another object of this invention to provide a safety hypodermic apparatus which provides an exposed sharpened tip for bevel-up needle viewing.

It is still another object of this invention to provide a safety hypodermic apparatus which automatically and/or manually entraps or captures the sharpened tip of the needle after use.

It is a further object of this invention to provide a safety hypodermic apparatus which allows medication or diluent to be aspirated into a syringe without prematurely activating the automatic and/or manually covering safety mechanism.

It is a still further object of the invention to provide a safety hypodermic apparatus which can be used with a double lancet needle for piercing a cartridge in a pre-filled syringe, or a stopper in a blood collection vacuum tube.

It is an additional object of this invention to provide a safety hypodermic apparatus which lends itself to automated manufacturing.

It is another object of this invention to minimize any mechanical resistance or component fatigue inherent to the stored energy components of the invention when the hypodermic needle is stored.

It is yet another object of the invention to leave the delicate, sharpened needle tip untouched during assembly procedures, ensuring the sharpest needle tip possible to minimize any patient discomfort during use of the hypodermic device.

It is a further object of the invention to reduce the number of components to the lowest possible number needed to accomplish the intended task of providing acceptable, low cost, fail-safe, single-use hypodermic devices for the healthcare industry.

It is yet another object of the invention to prevent catheter separation from the catheter carrying device until the needle tip is safely contained in a protective cover.

It is another object of the invention to provide a safety hypodermic apparatus that allows a protective cover to be used with long needles, such as epidural needles, spinal needles, or percutaneous entry needles for placing guidewires.

It is yet another object of the invention to provide a safety hypodermic apparatus that allows a protective cover to be used with needles that include a change in axis at the distal tip, such as implanted port needles, or needles with a "Huber" tip.

It is yet a further object of the invention to provide a safety hypodermic apparatus that allows a protective cover to be used with straight needle shafts, or bent needle shafts that include a change in axis at the distal tip, such as implanted port, needles or needles with a "Huber" tip.

It is yet another object of the invention to provide a safety hypodermic apparatus that includes a deformable retaining means for retaining and selectively releasing a protective member or cover.

It is another object of the invention to provide a safety hypodermic apparatus that includes a deformable retaining means that may be an integral part of a needle hub.

It is a further object of the invention to provide a safety hypodermic apparatus that includes a deformable retaining means that may be retrofitted to an existing needle hub.

It is another object of the invention to provide a safety hypodermic apparatus that includes a deformable retaining means that may include a gripping means.

In one embodiment the needle guard assembly of the present invention includes a needle guard that is slidably mounted on a hypodermic needle having a needle tip located at the distal end of the needle. The needle guard contains a movable needle trap that is biased against or toward the hypodermic needle. The needle trap advances over the tip of the needle, entrapping the needle tip as the needle guard is urged forward near the sharpened distal end of the hypodermic needle. A tether, or other limiting means, limits the forward movement of the needle guard along the needle. In one embodiment, the needle guard is manually urged forward along the shaft of the needle by the user. In yet another embodiment, a spring, or other biasing means, is used to move the needle guard along the shaft of the needle.

In another embodiment, a hypodermic needle is attached to a housing or hub. A coil spring is positioned between the hub, or housing, and the needle guard assembly. The spring provides the biasing force for advancing the needle guard assembly forward along the shaft of the needle. Prior to use, the needle guard assembly is releasably retained near the proximal end of the needle by a latching arm that is attached to the hub or housing. In one embodiment, the latching arm is automatically disengaged from the needle guard when a longitudinal compressive force is exerted on the retained needle guard. In yet another embodiment, the latching arm may be disengaged manually by the user.

In another embodiment, a hypodermic needle is attached to a housing or hub. A coil spring is positioned between the hub, or housing, and the needle guard assembly. The spring provides the biasing force for advancing the needle guard assembly forward along the shaft of the needle. Prior to use, the needle guard assembly is releasably retained near the proximal end of the needle by at least one protrusion that is selectively inserted into at least one aperture on a deformable member or housing. The needle guard is selectively released by squeezing the housing and expanding the housing diameter at the retaining interface to allow the protrusion to disengage from the aperture on the housing.

In another embodiment, a side-loadable needle guard assembly is provided that permits the needle tip protective device to be assembled without disturbing the delicate sharpened needle tip. In one embodiment the side-loadable needle guard assembly includes a slotted configuration. In yet another embodiment, the side-loadable needle guard assembly includes a "clam-shell" configuration.

In yet another embodiment, the needle guard assembly includes a coupling mechanism that prevents a mechanical separation from the catheter until the needle tip is safely contained within the needle trap. In one embodiment, the coupling mechanism includes an arm having a proximal end and a distal end. The proximal end of the arm is attached to the movable needle trap. The distal end of the arm includes a projection that is releasably retained within a recess of a catheter hub. Hence, as the needle trap moves inward to entrap the needle tip, the arm also moves inward. The inward movement of the arm causes the arm's distal projection to be released from the catheter hub recess, thereby permitting a separation between the needle guard assembly and the catheter hub.

Other objects and benefits of this invention will become apparent from the description which follows hereinafter when read in conjunction with the figures that accompany it.

BRIEF DESCRIPTION OF THE DRAWINGS

FIG. 1 illustrates a full side view of a prior art hypodermic needle attached to a hub.

FIG. 2 is a front view of the hypodermic needle hub shown in FIG. 1.

FIG. 3A is a full side view of the hypodermic needle hub shown in FIG. 1.

FIG. 3B is a full top view of the hypodermic needle hub shown in FIG. 1.

FIG. 4 is a cross sectional view of the hypodermic needle hub shown in FIG. 1.

FIG. 5 is a full side view of a hub in accordance with one embodiment of the present invention.

FIG. 6 is a cross sectional view of the hub shown in FIG. 5.

FIG. 7 is a cross sectional view of the hub shown in FIG. 5 having a flange section for retaining a removable cover.

FIG. 8 is a full side view of the hub shown in FIG. 7 with the addition of a protrusion for engaging a removable cover.

FIG. 9 is a full rear view of the needle hub shown in FIG. 7.

FIG. 14 is a full side view of one embodiment of the present invention comprising a unitary construction.

FIG. 15 illustrates one embodiment of the present invention in a ready-to-use state.

FIGS. 16–18 illustrate the needle guard assembly being activated to cover the tip of a hypodermic needle.

FIGS. 19–22 illustrate other embodiments of the present invention.

FIG. 23 illustrates another embodiment of the present invention.

FIGS. 24 and 25 show the present invention attached to a blood collection device.

FIG. 26 shows the present invention included in a catheter device.

FIG. 27 shows the present invention unitarily attached to a syringe.

FIG. 36 is an isometric open view of the needle guard shown in FIG. 34.

FIG. 37A shows the needle tip guard assembly of FIG. 35 in a ready to use state.

FIG. 37B shows the needle tip guard assembly of FIG. 37A after it has been activated.

FIGS. 38A and 38B show a needle tip protective device attached to a fillable syringe in a ready-to-use and shielded position, respectively.

FIGS. 39A and 39B show a needle tip protective device attached to a prefilled syringe in a ready-to-use and shielded position, respectively.

FIGS. 40A and 40B show a needle protective device attached to a prefilled cartridge.

FIGS. 42A and 42B illustrate another embodiment of the present invention.

FIG. 42C illustrates a needle guard assembly in one embodiment of the present invention.

FIGS. 43A and 43B show separate embodiments of the needle guard assembly of the present invention.

FIG. 44A illustrates another embodiment of the present invention.

FIG. 44B illustrates an enlarged cross-section view of the needle guard shown in FIG. 44A.

FIGS. 45A–C, 46 and 47 illustrate a needle hub in one embodiment of the present invention.

FIGS. 48A–C illustrate several retrofit hub configurations in accordance with the present invention.

FIG. 49A shows a full side view of the present invention attached to a prior art needle hub.

FIG. 49B is a cross-sectional view of FIG. 49A.

FIG. 50 is cross-sectional side view of the present invention attached to a prefilled syringe.

FIG. 51 is cross-sectional side view of the present invention attached to a prefilled cartridge syringe hub.

FIG. 52 is a cross-sectional side view of the present inventions intergrally molded to a prefilled cartridge syringe hub.

FIG. 56 illustrates the present invention attachable to a blood collection device.

FIG. 57 illustrates a full front view of a needle guard assembly in one embodiment of the present invention.

FIG. 58 is a cross sectional side view of a prior art prefilled syringe cartridge hub.

FIG. 59 is a cross sectional side view of the present invention being threadedly attached to a glass cartridge hub.

FIG. 60 is a cross sectional side view of the present invention fixedly attached to a glass cartridge.

FIGS. 61–63 illustrate a catheter in accordance with one embodiment of the present invention.

FIGS. 64–67 illustrate another embodiment of the present invention.

FIG. 68 illustrates a full side view of another embodiment of the present invention.

FIGS. 69–77 illustrate a needle guard assembly in accordance with one embodiment of the present invention.

FIG. 78 is a cross sectional side view of the present invention for use on a male luer syringe in a ready-to-use state.

FIG. 79 is a cross sectional side view of the present invention for use on a prefilled syringe or a prefilled cartridge syringe in a ready-for-use state.

FIG. 80 is cross sectional side view of the hub and cover shown in FIG. 78.

FIG. 81 is a cross sectional view of the needle and cover shown in FIG. 79.

FIGS. 82 and 83 illustrate a collar for use in one embodiment of the present invention.

FIG. 84 illustrates another embodiment of the present invention.

FIG. 85 illustrates yet another embodiment of the present invention.

FIG. 86 is a graph depicting the interaction of a resilient member and a sliding member without a needle guard notch.

FIG. 87 is graph depicting the interaction of resilient member and a sliding member with a needle guard notch.

FIGS. 88–94 illustrate a number of different embodiments of the present invention.

FIGS. 97–102 show the embodiments of FIGS. 50, 51, 52, 54 and 55 with a needle having a change in contour.

FIGS. 103–105 illustrate a catheter in yet another embodiment of the present invention.

FIGS. 106–108 show a cross sectional view of another embodiment of the present invention.

FIGS. 109–113 illustrate a side-loadable needle guard in one embodiment of the present invention.

FIGS. 114 and 115 show a needle guard assembly for use in a catheter.

FIGS. 116 and 119 show a needle trap in one embodiment of the present invention.

FIG. 117 is a full top view of a housing in one embodiment of the present invention.

FIG. 118 illustrates a cross sectional and cut-away view of a catheter introducer in one embodiment of the present invention.

FIGS. 120 and 121 illustrate catheter assemblies in yet other embodiments of the present invention.

FIGS. 122A–122C show an isometric view of a catheter in one embodiment of the present invention.

FIGS. 123 and 124 show a needle trap assembly for use in a catheter.

FIGS. 124–130 illustrate a needle guard in yet another embodiment of the present invention.

FIG. 131 illustrates a needle having an expanded change in profile near the sharpened tip.

FIG. 132 illustrates a needle having a reduced change in profile near the sharpened tip.

FIG. 133 illustrates a needle having an expanded change in profile near the sharpened tip limiting axial movement of a washer or bushing.

FIG. 134 illustrates a cross sectional view of the needle and washer shown in FIG. 133.

FIG. 135 illustrates a washer shown in FIGS. 133 and 134.

FIG. 140 is a full side view of a needle having a bend in the shaft, or change in axis, near the distal tip.

FIG. 141 is a cross sectional side view of a needle shown in FIG. 140 with a sliding cover being limited in movement by the change in axis of the needle shaft.

FIG. 142 is a cross sectional side view of a needle shown in FIG. 140 with a sliding bushing being limited in movement by the change in axis of the needle shaft.

FIG. 143 is a cross sectional side view of a needle guard assembly having a needle trap that is biased against or towards the hypodermic needle having a change in axis.

FIG. 144 shows a needle entrapped within a needle guard assembly shown in FIG. 143.

FIG. 145 illustrates a full side view of a needle hub having a deformable member or housing.

FIG. 146 illustrates a full front view of the needle hub shown in FIG. 145.

FIG. 147 illustrates a full top view of a needle hub having a deformable member or housing shown in FIG. 145.

FIG. 148 illustrates a full top view of a needle guard apparatus of the present invention shown in a ready to use state having a needle guard being releasably retained in a needle hub having a distal deformable member or housing shown in FIG. 147.

FIG. 149 illustrates a full front view of a needle guard assembly with an off set split line shown in one embodiment of the present invention.

FIG. 150 illustrates a full front view of the needle guard assembly of FIG. 148 being retained in a deformable housing shown in one embodiment of the present invention.

FIG. 151 illustrates a full front view of a needle guard assembly of FIG. 150 being selectively released by compressing and deforming the housing.

FIG. 152 illustrates an isometric view of a needle tip guard assembly being retained in a deformable member or housing in a ready to use state.

FIG. 153 shows the needle tip guard assembly of FIG. 152 after it has been activated.

DETAILED DESCRIPTION OF THE INVENTION

Figure 10:
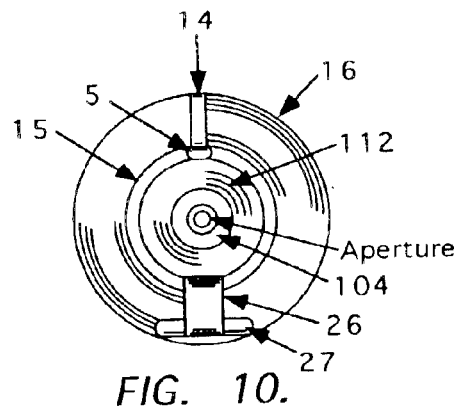
FIG. 10 is a full front view of the hub shown in FIG. 7.

A needle tip protective device is described. In this regard, to the extent applicable, this application is related to and claims the benefit of filing dates of the following U.S. Non-Provisional patent applications: (1) Ser. No. 60/012,343, entitled PROTECTED HYPODERMIC NEEDLE WITH AUTOMATIC AND MANUAL COVERING MEANS, filed Feb. 27, 1996; (2) Ser. No. 60/025,273, entitled HYPODERMIC DEVICES WITH SAFETY FEATURES, filed Sep. 12, 1996; and (3) Ser. No. 60/031,399, entitled HYPODERMIC DEVICES WITH IMPROVED SAFETY FEATURES, filed Nov. 19, 1996; (4) U.S. patent application Ser. No. 807,328 entitled NEEDLE TIP GUARD FOR HYPODERMIC NEEDLES, now issued as U.S. Pat. No. 5,879,337; (5) U.S. patent application Ser. No. 09/172,185 entitled INTRAVENOUS CATHETER ASSEMBLY, now issued as U.S. Pat. No. 6,001,080, filed on Oct. 13, 1998; and U.S. patent application Ser. No. 09/144,398 entitled NEEDLE TIP GUARD FOR HYPODERMIC NEEDLES, filed on Aug. 31, 1998, the teachings of which are expressly incorporated here and by reference. In the following description, numerous specific details are set forth in order to provide a thorough understanding of the present invention. However, it will be obvious to one of ordinary skill in the art that the invention may be practiced without these specific details. In other instances, well-known structures and processing steps have not been shown in particular detail in order to avoid unnecessarily obscuring the present invention. Additionally, it should be noted that throughout this discussion reference will be made to a variety of hypodermic needle devices such as fillable syringes, prefilled syringes, prefilled cartridge syringes, blood collection devices, percutaneous entry needles, implanted port needles and catheters. It is appreciated, however, that the present invention is not limited to these devices, and may be used in any application where it is desirable to provide a protective covering at the tip of a needle or other elongated object.

Also keep in mind that the needle covering invention disclosed herein in regard to an I.V. catheter can easily be adapted to all types of other catheters where a needle may be used, including, but not limited to, neurological, urological, central venous, oximetry, thermodilution, PTCA, PTA, angiography, atherectomy, enlectrophysiology, suction and wound drainage, cardiovascular, pulmonary and spinal catheters. The needle covering invention described herein on a syringe can also be easily adapted to a blood collection needle, or any other needles used in invasive procedures, including, but not limited to, angiography, cardiovascular, ophthalmological, orthopedic, dentistry, veterinary, chemotherapy and arterial blood gas.

FIG. 1 is a full side view drawing of a prior art standard, exposed hypodermic needle 10, having a sharpened needle tip 11 at the distal end with the opposite, or proximal end of the needle 10 attached to a hub 12, with at least one flange 1 at the very proximal end for attaching the needle hub 12 to a male luer fitting, a needle nest 4 at the distal end of the needle hub 12, for fixedly attaching the needle 10, and a plurality of fins 2 on the needle nest 4.

FIG. 2 is a full front view drawing of the prior art hypodermic needle hub 12 with an aperture creating a fluid/gaseous path to the hypodermic needle, a needle nest 4 for fixedly attaching the hypodermic needle 10 therein, with the needle nest 4 surrounded by a plurality of fins 2 and a plurality of flanges 1.

FIG. 3A is a full side view drawing of the prior art hypodermic needle hub 12 with at least one flange 1 for attaching the needle hub 12 to a male luer fitting, a needle nest 4 for fixedly attaching the needle (not shown here) and a plurality of fins 2.

FIG. 3B is a full top view drawing of the prior art hypodermic needle hub 12 with at least one flange 1 for attaching the needle hub 12 to a male luer fitting, a needle nest 4 for fixedly attaching the needle (not shown here) and a plurality of fins 2.

FIG. 4 is a cross-sectional view of the prior art hypodermic needle hub shown in FIG. 2 along axis 4—4 comprising a hub portion 12 with a flange 1, an aperture creating a fluid/gaseous path to the hypodermic needle (not shown here), a needle nest 4 for fixedly attaching a hypodermic needle (not shown here), and a plurality of fins 2.

FIG. 5 is a full side view drawing of the hub section of the disclosed invention comprising a hypodermic needle hub 112 with at least one flange 101 for attaching the needle hub 112 to a male luer fitting, a needle nest 104 (not shown here) for fixedly attaching the needle (not shown in this view), an inner aperture creating a fluid/gaseous path between the needle hub 112 and the needle (not shown here), a protrusion 5 located at the distal end of the needle hub 112, the protrusion being connected to the extended sidewall section 15 at the distal end of the needle hub 112, and a moveable latching arm 26 with a finger pad 27 attached to the needle hub 112 by a hinge section 23, with the moveable latching arm 26 having a protrusion 21 for retaining a component in a releasable position on the needle hub 112, said moveable latching arm 26 shown in the preferred molded position.

FIG. 6 is a cross-sectional side view of FIG. 5. Needle hub 112 includes an inner aperture that provides a fluid/gaseous path between the needle hub 112 and the needle (not shown here). Arrow "M" indicates the directional movement of latch 26.

FIG. 7 is a cross-sectional side view of FIG. 5 having a section 16 for removably holding a removable cover over the hypodermic needle.

FIG. 8 is a full side view of the hub 112 shown in FIG. 7, with the addition of at least one protrusion 14 located adjacent to section 16, said protrusion 14 being engagable with a removable cover. Protrusion 14, in conjunction with a contacting member of removable cover, is positioned to facilitate attachment or removal of a hypodermic needle from a connecting device. Hub 112 also includes a protrusion or cleat 17 with a cap or holding means 18 to attach a tether.

FIG. 9 is a full rear view of needle hub 112 shown in FIG. 7.

FIG. 10 is a full front view drawing of the disclosed hub invention comprising a hypodermic needle hub 112 with an extended wall section 15, an aperture creating a fluid/gaseous path to the hypodermic needle (not shown), a needle nest 104 for fixedly attaching the needle (not shown), a protrusion 5 which can be used as a guide for aligning another component, a section 16 for removably holding a removable cover over the hypodermic needle (not shown here), a protrusion 14 located adjacent to section 16 for engaging a corresponding component of a removable cover (not shown), and a moveable latching arm 26 with a finger pad 27 attached to the needle hub 112 by a hinge section 23 (not shown).

Figure 11:
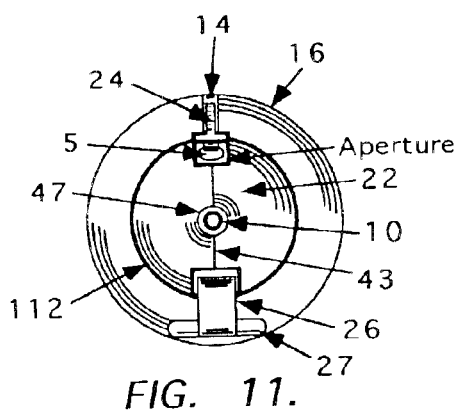
FIG. 11 is a full front view of a needle guard assembly in one embodiment of the present invention.

FIG. 11 is a full front view of a needle guard assembly 22 positioned on the front of the hub 112 comprising a guide aperture 47 with a hypodermic needle 10 therethrough, said aperture 47 being created by coupling the open-faced sections of the needle guard assembly 22 together at a split line 43, a protrusion 5 which is used as a guide for aligning the needle guard assembly 22 on the hub 112 whereby an aperture is created on the needle guard assembly 22 when the open-faced sections of the needle guard assembly 22 are coupled together, a section 16 for removably holding a removable cover over the hypodermic needle 10, a protrusion 14 located adjacent to section 16 for engaging a corresponding component of a removable cover (not shown). In one embodiment needle guard 22 also includes a moveable latching arm that is attached to needle hub 112 by a hinge section. A tether (not shown) is generally used to fixedly attach needle guard 22 to hub 112.

Figure 12:
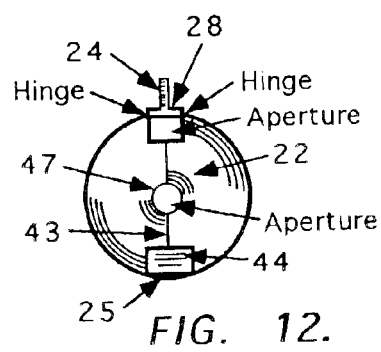
FIG. 12 is a full front view of the needle guard assembly shown in FIG. 11.

FIG. 12 is a full front view of the needle guard assembly 22 shown in FIG. 11 comprising a guide aperture 47 created by coupling the open-faced sections of the needle guard assembly 22 together at the split line 43, a recess 25 with a protrusion 44 at the rear or inner end of the recess 25, a tether 24 connected to a hinge section 28 and an aperture adjacent to the hinge section.

Figure 13:
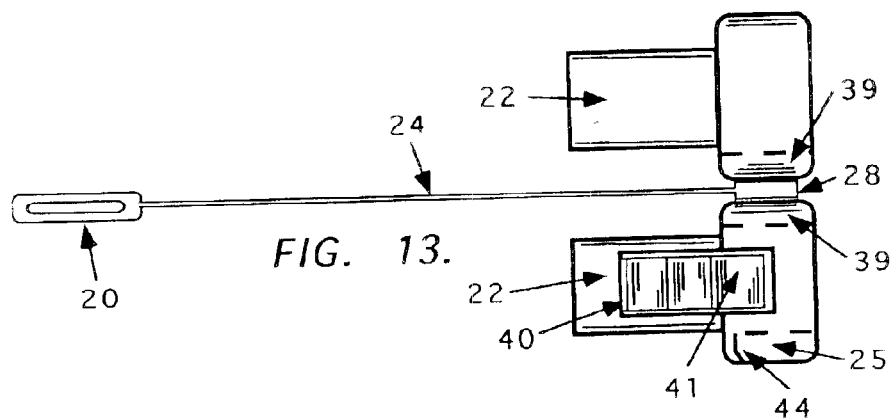
FIG. 13 is a full outside view of a needle guard assembly and tether in one embodiment of the present invention.

FIG. 13 is a full outside, top view of the needle guard assembly 22 and tether 24 as manufactured comprising an openfaced needle guard 22 with a hinge section 28, with adjacent lands 39 which create an aperture when the needle guard assembly 22 is coupled together, a needle tip guard 41 with a hinge section 40 allowing the needle tip guard 41 to move, a recess 25 with a protrusion 44 and a tether 24 with a connector or loop 20.

FIG. 14 is a full side view of a unitary, one piece embodiment of the invention comprising a hypodermic needle hub 112, having at least one flange 101, an extended wall section 15, a protrusion 5, a moveable latching arm 26 connected to said hub 112 by a hinge 23, said latching arm having a finger pad 27 at the proximal end and a hooking protrusion 21 at the distal end, a protrusion 17 connecting a tether 24 to a slidable needle guard assembly 22, with a moveable needle tip guard 41 and a hinge section 40. In addition to serving as an alignment guide needle guard 22, protrusion 5 may also serve as an aspiration stop when a needle is inserted into a medicine vial.

FIG. 15 is a full side view of the invention shown in the ready to use configuration comprising a hypodermic needle 10 with a sharpened tip 11, a needle hub 112, with at least one flange 101, an extended sidewall section 15, a section 16 for removably attaching a cover, a protrusion 14 located adjacent to section 16, said protrusion 14 being engagable with a removable cover, said protrusion 14 in conjunction with corresponding member of removable cover, being positioned to facilitate attachment or removal of a hypodermic needle from a connecting device, a moveable latching arm 26 connected to hub 112 by a hinge 23, said latching arm having a finger pad 27 at the proximal end and a hooking protrusion 21 at the distal end, said latching arm 26 releasably holding said needle guard 22 and a compressed resilient member 19 in a retained position, said needle guard 22 having a moveable needle tip guard 41 which is biasly contacting the hypodermic needle, a protrusion 5 on the hub 112 for aligning a needle guard assembly 22 to the needle hub 112 so the moveable latching arm 26 properly enters the corresponding recess 25 on the needle guard assembly 22, said needle guard assembly 22 being connected to said hub 112 by a tether 24.

FIG. 16 is a full side view FIG. 15 with a compressive longitudinal force being exerted on the needle guard assembly 22, whereby the needle guard assembly 22 and compressed resilient member 19 move enough to release the hold by the protrusion 21 of the moveable latching arm 26.

FIG. 17 is a full side view FIG. 15 with the released needle guard assembly 22 being urged to the distal end of the hypodermic needle 10 by the extending force of the resilient member 19, said needle tip guard 41 is biasly contacting said hypodermic needle 10 by the inherent memory of the molded configuration of said needle tip guard 41 and/or the extending force of the surrounding resilient member 19.

FIG. 18 is a full side view FIG. 15 with the resilient member 19 extended and still exerting force on the needle guard assembly 22, said resilient member 19 assists inherently molded bias of needle tip guard 41 by urging said needle tip guard 41 inwardly and ahead of the sharpened needle tip, said needle guard assembly 22 is limited from advancing further by the extended tether 24, with the sharpened hypodermic needle tip being entrapped within the needle guard assembly 22, with the needle tip guard 41 now securely positioned ahead of the sharpened needle tip said needle tip guard 41 blocking the aperture guide of the needle guard assembly 22, ensuring safe containment of the sharpened tip.

FIG. 19 is a full bottom view of FIG. 15 showing the elements of the invention and a rectangular finger pad configuration, although the finger pad configuration only needs to be suitable (round, square, triangular or the like) to facilitate a manual force to release the hold on retained needle guard assembly 22, said needle guard assembly 22 having a recess 25 for engaging the distal end of the movable latching arm 26 to the corresponding section on the needle guard assembly 22.

FIG. 20 is a full top view of FIG. 15 showing the elements of the invention and having a tether 24 which can have a round, square, elliptical or ribbon-like cross section and hinge section 28. It is important to note that the tether can comprise either rigid or flexible characteristics, and can be unitary molded with other components, or be a separate component. A rigid tether would have to be able to slide along the side of a syringe, prefilled syringe or cartridge, blood collection needle holder or I.V. catheter when the device is used, and said tether could slide through an aperture which would limit the axial forward movement of the tether and needle guard. This rigid tether would have to have a proximal end larger than the aperture, so the tether would be limited in its slidable movement.

A flexible tether can be made more resilient or rigid by changing the molecular alignment of the molecules of the tether component by stretching, heating, radiation processing or the like. The tether can be manufactured separately, or connected to either the hub component, the needle guard assembly or the needle guard housing. The tether could be comprised from a single variety, or a combination of materials including, but not limited to: plastic resin, synthetic material, organic material, cloth, woven material, stranded material, metal, silk, or a composite material.

FIG. 21 is a full side view of FIG. 15 having an extended protrusion 105 for preventing premature release of the releasable needle guard assembly 22. This embodiment can be used for blood collection purposes, indwelling catheter placement or preventing premature activation during medicine aspiration.

FIG. 22 is a full top view of FIG. 15 having an extended protrusion 105 for preventing premature release of the releasable needle guard assembly 22.

FIG. 23 is a cross-sectional view of the invention ready for use having the elements described herein, with the resilient member 19 in a compressed position with the needle guard assembly releasably held by the protrusion 21 of the moveable latching arm 26, an aperture for orienting said needle guard assembly 22 adjacent to said hub portion 112, and an aperture 47 with a hypodermic needle 10 therethrough, said latching arm 26 having a protrusion 49 for engaging said needle guard assembly 22 when said needle guard assembly is moved toward said hub portion 112, said protrusion 49 manually moves said latching arm 26 in an outward manner ensuring said latching arm 26 moves outwardly releasing the hold on the needle guard assembly 22.

FIG. 24 is a full side view of the invention for blood collecting purposes showing the elements described and notated in the previous drawings in addition to a double-lancet hypodermic needle 110 having a sharpened tip 11 at the distal end and a sharpened tip 111 at the proximal end (see FIG. 25), a hub 212 having a threaded section for removably attaching the hub into a needle holder 45 (see FIG. 25) by means of threads 74, and a piercable, collapsible cover 48 on the distal end of the needle 110 and a protrusion 105.

FIG. 25 is a full side view of the invention for blood collecting purposes showing the elements described and notated in the previous drawings in addition to the invention being removably attached to a needle holder 45, said needle holder 45 having a larger opening at the proximal end for inserting a removable blood collection tube, and a smaller opening at the distal end for removably attaching a blood collection needle 110 and hub 212. A manual releasing means is activated by pressing the finger pad 27 in a downward or inward manner, this is indicated by the arrow "F" pointing toward the finger pad 27.

It may be noted that the attachment means of connecting the invention to a blood collection needle holder 45 is not limited to the threaded means 74 shown throughout this application. Other attachment means, such as frictional engagement, snap fit, wedging or the like may also be used to accomplish the same function.

FIG. 26 is a full side view of the invention with a removable, indwelling catheter, having a hub 312 attached to a hollow bore needle 210 with a distal stylet 211 and a removable, indwelling catheter 51 and catheter hub 50 slidably disposed on said needle 210. All other elements notated are described in the previous drawings.

FIG. 27 is a full side view of the invention in a ready to use state unitarily attached to a syringe 6 by the hub 112. All other elements notated are described in the previous drawings.

Figure 28:
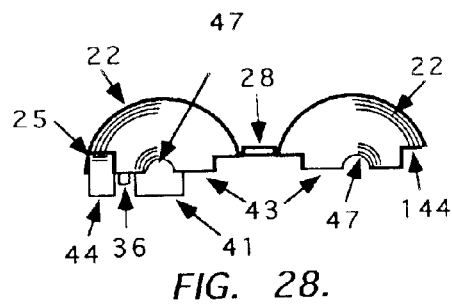
FIGS. 28 and 29 show a needle guard in accordance with one embodiment of the present invention.

FIG. 28 is a full front view of the needle guard assembly shown in an open-faced configuration comprising a needle guard assembly 22 having a hinge section 28 joining each section, a split line 43 where the sections mate together, an aperture guide 47 on each section, a recess 25 on one section having a protrusion 44 for joining with the corresponding element 144 on the other section of said needle guard assembly 22, a moveable needle tip guard 41 and a post 36 for joining the needle guard assembly 22 sections together.

Figure 29:
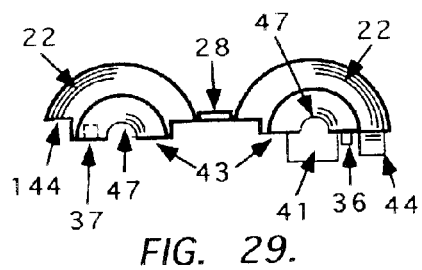

FIG. 29 is a full rear view of the needle guard assembly shown in an open-faced configuration comprising a needle guard assembly 22 having a hinge section 28 joining each section, a split line 43 where the sections mate together, an aperture guide 47 on each section, a protrusion 44 for joining with the corresponding element 144 on the other needle guard assembly 22 section, a moveable needle tip guard 41, at least one post or protrusion 36 on one needle guard assembly 22 section which enters at least one corresponding slot 37 on the other needle guard assembly 22 section for securing the sections together.

Figure 30:
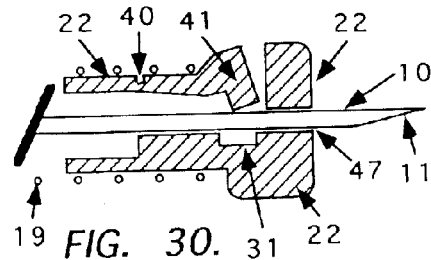
FIG. 30 shows a needle trap that is biased against or towards the hypodermic needle.

FIG. 30 is a cross-sectional side view showing the interaction of the needle guard assembly 22 with the resilient member 19 and hypodermic needle 10 and sharpened needle tip 11, comprising a moveable needle guard assembly 22 with a hypodermic needle 10 therethrough, with resilient member 19 urging the needle guard assembly 22 toward the distal end of the hypodermic needle 10. The needle guard assembly 22 having a moveable needle tip guard 41 with a hinge section 40, said needle tip guard 41 is molded in a manner whereby the needle tip guard 41 comprises an inherent biasing force toward the hypodermic needle 10, another biasing force is exerted on the needle tip guard 41 by the extending force of the resilient member 19, said needle tip guard 41 enters the corresponding recess 31 when said needle tip guard 41 advances beyond the sharpened needle tip 11, said needle tip guard 41 slidably contacts said hypodermic needle 10. The needle guard 22 is attached to a hub element 12 by means of a tether 24 as described and notated in the previous drawings.

Figure 31:
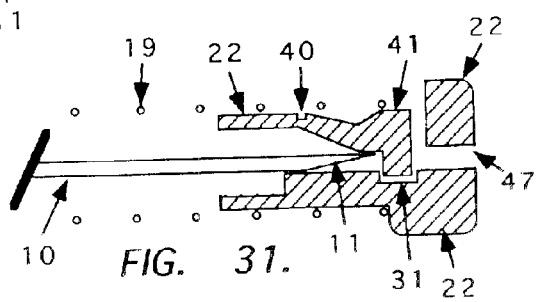
FIG. 31 shows a needle entrapped within a needle guard assembly in one embodiment of the present invention.

FIG. 31 is cross-sectional side view showing containment of the sharpened needle tip 11 within the needle guard assembly 22 comprising a needle guard assembly 22 with a hypodermic needle 10 therethrough, said needle guard assembly 22 being urged beyond the distal end of the hypodermic needle 10 and sharpened needle tip 11 by the extending force of a resilient member 19 whereby the moveable, self-biasing needle tip guard 41 of the needle guard assembly 22 moves in front of the sharpened needle tip 11, containing the sharpened needle tip 11 within the needle guard assembly 22 and behind the substantially impenetrable needle tip guard 41 having a hinge section 40. Additionally, the extending force of the resilient member 19 urges the needle tip guard 41 inwardly to a covering position, said resilient member 19 surrounds both the needle guard assembly 22 and the outer wall of the needle tip guard 41 holding the needle tip guard 41 in a closed, protective position by a radially confining force. In the protected, closed position, the needle tip guard 41 enters the corresponding recess 31 of the needle guard assembly 22, preventing movement and ensuring safe containment of the sharpened needle tip 11 within the needle guard assembly 22. The needle guard 22 is attached to a hub or housing by means of a tether as described and notated in the previous drawings.

Figure 32:
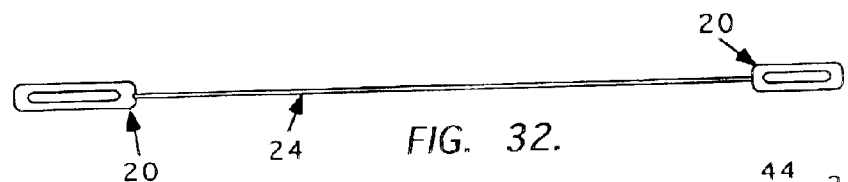
FIG. 32 illustrates a tether in one embodiment of the present invention.

FIG. 32 is a full top view of a separate tether 24 with connecting loops 20 at the proximal and distal ends. This tether embodiment is used with a separate hub component and separate needle guard assembly component.

Figure 33:
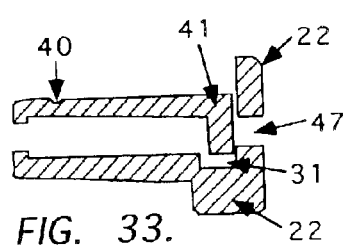
FIG. 33 illustrates a needle trap in one embodiment of the present invention.

FIG. 33 is a cross sectional side view of the needle guard assembly 22 comprising a needle tip guard 41 having a hinge section 40 connected to the needle guard assembly 22. Said needle tip guard 41 is molded in a self-biasing manner as shown and is moveable to an open and closed position. Said needle tip guard may comprise a substantially impenetrable plastic resin and/or a substantially impenetrable metal.

Figure 34:
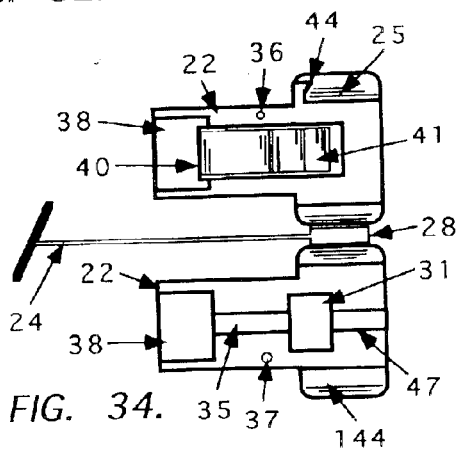
FIG. 34 is a full open view of a needle guard assembly in one embodiment of the present invention

FIG. 34 is a full open view of the interior of the open-face needle guard assembly 22 as manufactured and before being joined together. Said needle guard assembly 22 comprising two joining sections which are connected by a hinge section 28 having a tether 24, one needle guard assembly section having a moveable, self-biasing, substantially impenetrable needle tip guard 41 with a moveable hinge 40 connected to said needle guard assembly 22, a post or protrusion 36, a recess 25 with a protrusion 44 and a recess 38 for nesting said needle guard assembly 22 adjacent to the needle hub 112, 212 or 312 as shown in the previous drawings; with the corresponding needle guard assembly section having a corresponding slot 31 for said needle tip guard 41 to enter, a slot 37 for receiving the corresponding post 36, a proximal inner guide section 35 and a distal inner guide section 47 for the hypodermic needle 10 (not shown), a corresponding receiving section 144 for recess 25 and protrusion 44, and a recess 38 for nesting said needle guard assembly 22 adjacent to the needle hub 112, 212 or 312 as shown in other drawings herein.

Figure 35:
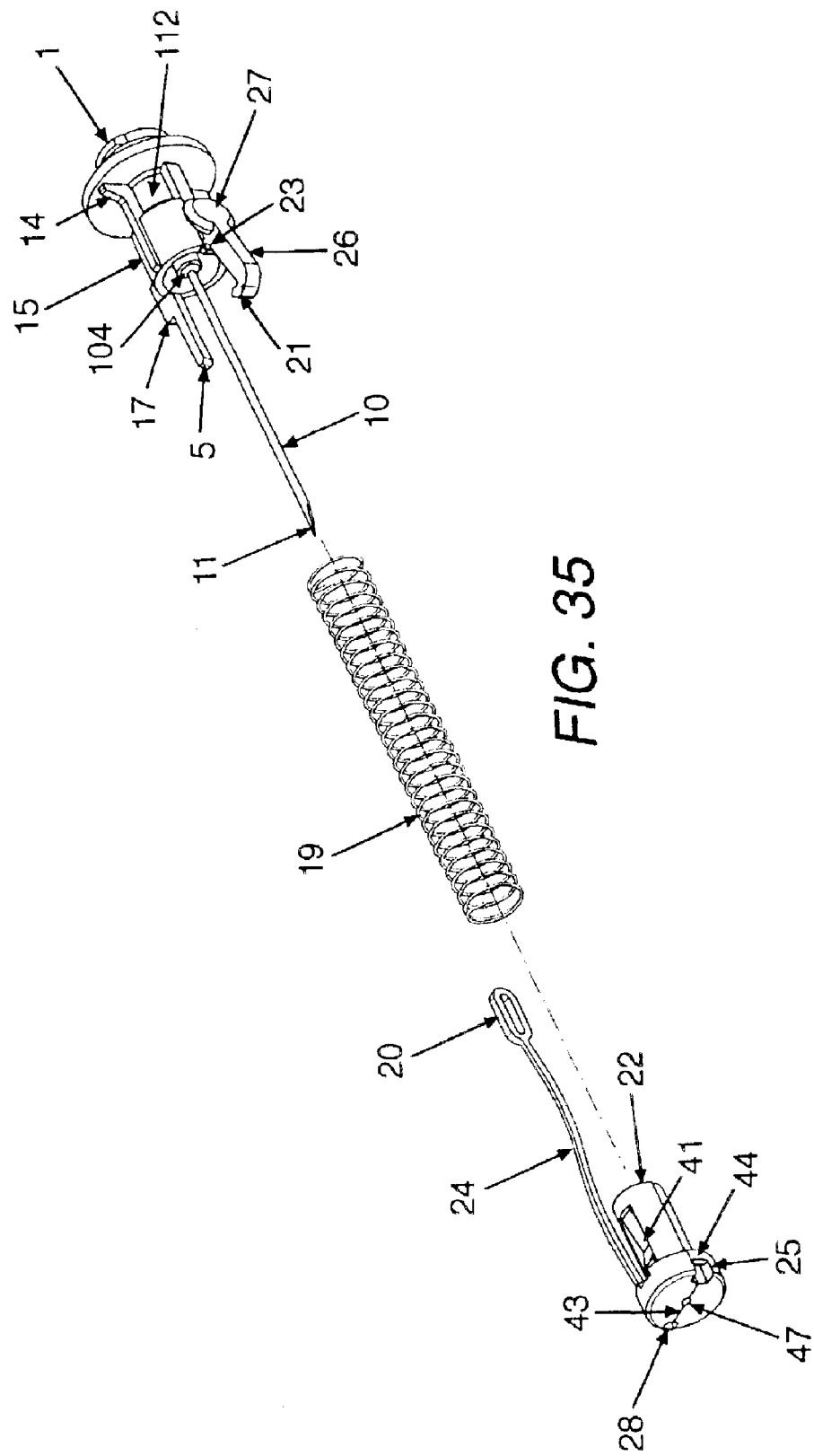
FIG. 35 is a exploded view of one embodiment of the present invention.

FIG. 35 is a full, exploded view of the invention having the elements described herein the other accompanying drawings comprising a slidable needle guard assembly 22 in the closed face configuration having a tether 24 and loop 20; a resilient member 19; and a hypodermic needle 10 fixedly attached the needle hub. FIG. 36 shows needle guard assembly 22 in a full view, open-faced configuration. The open face, or "clam-shell" configuration of the needle guard make this embodiment feasible using standard injection molding techniques. The sharpened needle 10 is first attached to the hub portion 112, then the needle 10 is coated with a friction-reducing lubricant, the resilient member 19 is concentrically disposed over the needle 10 and compressed, then the needle guard assembly 22 is assembled from the side of the needle 10 keeping the sharpened tip 11 from being contacted, the needle guard assembly 22 and tether 24 are then attached to the hub 122 by a connecting means 20.

The extended wall section 15 can be eliminated for the invention to work, but shields the resilient member 19. The elements of the needle guard assembly 22, in relation to each other, and in relation to the bevel of the sharpened needle tip 11, can also be oriented as may be deemed necessary to suit a specific procedure or purpose.

FIG. 37A is an isometric drawing of a needle tip protective device 500 in one embodiment of the invention. FIG. 37A shows protective device 500 in a ready-to use position. FIG. 37B shows the protective device 500 shielding the needle tip within the needle guard assembly 22.

FIGS. 38A and 38B show a needle tip protective device 500 in one embodiment of the invention attached to a fillable syringe 501 in a ready-to-use position and a shielded position, respectively.

FIGS. 39A and 39B show a needle tip protective device 500 in one embodiment of the present invention attached to a prefilled syringe 502 in a ready-to-use position and a shielded position, respectively.

FIGS. 40A and 40B show a needle protective device 500 in one embodiment of the invention attached to a prefilled cartridge 503. FIG. 40A shows the prefilled cartridge 503 before use. FIG. 40B shows the prefilled cartridge 503 after the protective device 500 is activated.

Figure 41A:
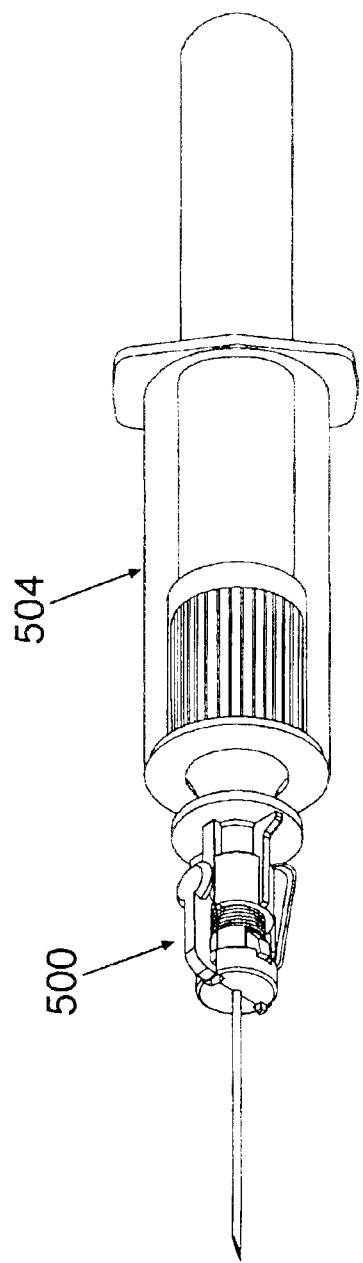
FIGS. 41A and 41B show a needle protective device attached to a blood collection apparatus in a ready to use and shielded position, respectively.
Figure 41B:
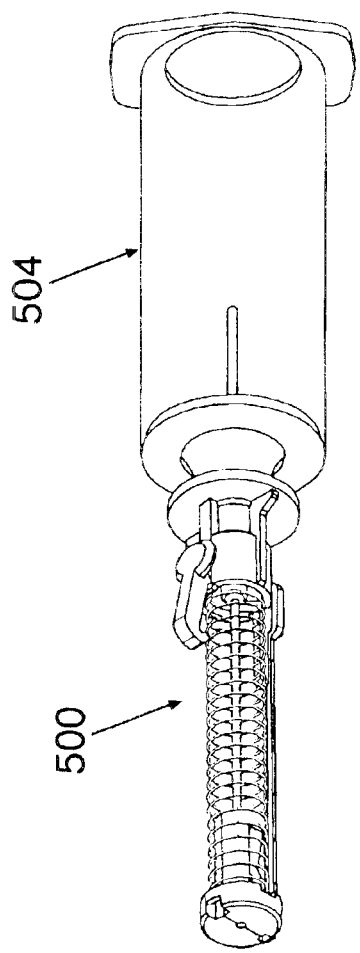

FIGS. 41A and 41B shows a needle protective device 500 in one embodiment of the invention attached to a blood collection device 504 in a ready-to-use position and a shielded position, respectively.

FIG. 42A illustrates a needle tip guard assembly in yet another embodiment of the present invention for protecting the distal tip 11 of a standard hypodermic needle 10. The assembly 20 includes a needle guard 22 that is slidably mounted on needle 10. Needle guard 22 contains a movable needle trap 41 that is biased against or toward the shaft of needle 10. Needle trap 41 advances over the tip 11 of the needle 10, entrapping the needle tip 11, when needle guard 22 is positioned near the distal tip of needle 10. FIG. 42B shows distal needle tip 11 captured within needle guard 22.

In the embodiment of FIG. 42A, needle guard 22 is moved forward along the shaft of needle 10 by the user. In FIG. 42A, needle trap 41 is shown as a detachable element of needle guard 22 that is insertable into a slot 80 located adjacent the proximal end of needle guard 22. Needle trap 41 generally comprises a flexible metal member. Other impregnable materials that are not susceptible to fatigue may also be used. For example, some plastics or other resin based materials may be used. In such instances, needle trap 41 may be integrally molded with needle guard 22. A recess 31 may be included within needle guard 22 for receiving needle trap 41. A flexible tether 24 limits the forward movement of the needle guard 22 along the needle 10. Other limiting means, such as, for example, a change in contour in needle 10 or the use of a rigid tether assembly may be used in lieu of the flexible tether. These limiting devices will be described in greater detail later in this description.

FIG. 42C shows needle guard 22a that is another embodiment of the needle guard 22 shown in FIGS. 42A and 42B. The needle guard 22a of FIG. 42C includes an integrally molded needle trap 41a, a notch 61a, a recess 61b in trap 41a, and needle guard 22, respectively. A resilient member 102 is held within notch 61a and recess 61b. The stored energy of resilient member 102 urges needle trap 41a toward or against needle 10. Resilient member 102 may comprise a "v" shape or may simply comprise a member that has been curved to create a stored energy.

FIG. 43A is a full side view one embodiment of the present invention with the resilient member 119 extended and still exerting force on the needle guard assembly 22, said resilient member 119 assists inherently molded bias of needle guard trap 41 by urging said needle guard trap 41 inwardly and in front of the sharpened needle tip 11 (see FIG. 33), said needle guard assembly 22 is limited from advancing further by the limiting tether 24, with the sharpened hypodermic needle tip being entrapped within the needle guard assembly 22, with the needle guard trap 41 now securely positioned in front of the sharpened needle tip 11 said needle guard trap 41 blocking the aperture guide opening 47 of the needle guard assembly 22, ensuring safe containment of said sharpened tip 11 within the needle guard assembly 22. The needle guard trap 41 is attached to the needle guard assembly 22 by a hinge section 40. A hollow bore hypodermic needle 10 is fixedly attached to a hub 112, said hub 112 having at least one proximal flange 101 for attaching said hub 112 to a male luer fitting, said hub 112 also having a flange 16 for removably attaching a protective storage cover (not shown), said flange 16 having at least one shoulder or projection 14 for interfacing with a corresponding portion of a storage cover to allow twisted attachment and/or removal of said hub 112 to or from a medical device, said hub also having a body portion 15, a protrusion 5, and a movable latching arm 26, said latching arm 26 being fixedly attached to said hub body 15 by a hinge section 23, said latching arm also having a hook 21, a protrusion, cam, or ramp 49 and a finger pad or button 27.

FIG. 43B shows the protective needle guard assembly of FIG. 43A attached to a syringe 6. The protective needle guard assembly may be integral to syringe 6, or may be attached as an add-on component.

FIG. 44A is a full side view of the disclosed invention with the resilient member 119 extended and still exerting an extending force on the needle guard assembly 22, said resilient member 119 assists inherently molded bias of needle guard trap 41 by urging said needle guard trap 41 inwardly and in front of the sharpened needle tip 11 said needle guard assembly 22 is limited from advancing further by the limiting tether 24, with the sharpened hypodermic needle tip 11 being trapped within the needle guard assembly 22, with the needle guard trap 41 now securely positioned in front of the sharpened needle tip 11. Said needle guard 22 having an extended slot section 44a for releasably holding said needle guard assembly 22 in a retained position. Said extended slot section 44a places the interface between the latching arm hook 21 and the needle guard assembly 22 away from any potential binding which may occur during needle insertion. If the retaining means interface is too close to the insertion surface, the latching arm 26 may be prevented from releasably holding the needle guard assembly 22. A flexible projection 107 is included within the needle guard assembly for retaining the end coil of spring 119 in a locked position after the needle tip protection device has been activated. FIG. 44B illustrates a cross-sectional view of flexible projection 107. The needle guard trap 41 is attached to the needle guard assembly 22 at a hinge section 40. The needle 10 is fixedly attached to a hub 112, said hub 112 having at least one proximal flange 101 for attaching said hub 112 to a male luer fitting, said hub also having a body portion 15, a protrusion 5, and a movable latching arm 26, said latching arm 26 being fixedly attached to said hub body 15 by a hinge section 23, said latching arm also having a hook 21 and protrusion 49.

FIG. 45A is a full side view drawing of the needle hub 412, in accordance with one embodiment of the invention comprising a hypodermic needle hub 412 with a flange 401 for attaching the needle hub 412 to a male luer fitting, a needle nest 404 for fixedly attaching the needle, a plurality of fins 402, and a land 75 for attaching another component to the hub 412.

FIG. 45B is a full top view of the needle hub 412 shown in FIG. 45B having a flange 401 for attaching the needle hub 412 to a male luer fitting, a needle nest 404 for fixedly attaching a needle, a plurality of fins 402, and a land 75 for attaching another component to the hub 412.

FIG. 45C is a cross sectional side view of FIG. 45A comprising a hypodermic needle hub 412 with a flange 401 for attaching the needle hub 412 to a male luer fitting a needle nest 404 for fixedly attaching the needle 10, an aperture therethrough creating a fluid/gaseous path from the said hub 412 to said needle 10, a plurality of fins 402, and a land 75 for attaching another component to the hub 412.

FIG. 46 is a full side view drawing of the disclosed invention comprising a hypodermic needle hub 412 with a flange 401 for attaching the needle hub 412 to a male luer fitting, a needle nest 404 for fixedly attaching the needle, at least one, or a plurality of shortened fins 403, and a land 75 for attaching another component to the hub 412.

FIG. 47 is a full front view drawing of FIGS. 45A and 46 comprising a hypodermic needle hub 412 with an aperture creating a fluid/gaseous path to the hypodermic needle 10, a needle nest 404 having adjacent at least one, or a plurality of fins 402 or 403, at least one, or a plurality of flanges 401 and a land 75.

FIG. 48A is a is a full side view of the invention having a retrofitted hub portion 215 being fixedly attached to a hub portion 412 by a heatstake connection. Said hub portion 215 having an annular flange 16 for connecting a protective storage cover, a protrusion 17 for attaching a tether, said protrusion 17 having an aperture for insertably attaching or bonding the tether, said protrusion 17 having an angled proximal end to eliminate any possibility of the tether catching on the protrusion 17 when the needle guard 22 is activated. A hub portion 215 also includes a well or pocket 18 for removably inserting a tether in an out of the way fashion, and a retaining means 77 for releasably holding said needle guard 22 in a retained position adjacent to said hub portion 215.

FIG. 48B is a full front view of the hub 215 described in FIG. 48A comprising a hypodermic needle hub 215 having an aperture with a plurality of slots which correspondingly fits onto the distal end of a hypodermic needle hub shown throughout this application, said slots accept the fin or fins 402 from said hub 412, an annular flange 16, a protrusion 17 for attaching a tether or the like, a well or pocket 18 for removably inserting a tether or the like, and a retaining means 77 having an aperture 78 for releasably holding said needle guard 22 in a retained position adjacent to said hub portion 215.

FIG. 48C is a full front view of FIG. 48A comprising a hypodermic needle hub portion 215, an aperture which correspondingly fits onto the distal end of a hypodermic needle hub shown throughout this application, an annular flange 16. There is one slot shown with the aperture, and at least one slot is needed to secure the needle hub 412 and hub portion 215 together to keep the hub portion 215 and needle hub 412 aligned when a circumferential force is exerted on the adjacent components.

FIG. 49A is a full side view of the disclosed invention being fixedly attached to a prior art needle hub 12 having at least one flange 1 for attaching the needle hub 12 to a male luer fitting, a section 16 for removably holding a protective storage cover 54 over the hypodermic needle 10 (shown in other drawings in this application), a protrusion 5 located at the distal end of the hub portion 15, said protrusion 5 being connected to the hub portion 15 at the distal end of the hub portion 15, said section 16 having a shoulder 14 for twistedly attaching said invention to said storage cover, and a moveable latching arm 26 with a finger pad 27, attached to the hub portion 15 by a hinge section 23, said finger pad 27 having at least one protrusion for creating a more positive grip or contact with said finger pad 27. Finger pad 27 also comprising a different, or bright color, which serves as a visual indicator for the user to easily locate the finger pad for manual release of said needle guard assembly 22 or the like, with the moveable latching arm 26 having a protrusion 21 for retaining a component in a releasable position adjacent to said hub portion 15, said moveable latching arm 26 shown in the preferred molded position.

FIG. 49B is a cross-sectional side view of FIG. 49A showing the disclosed invention attached to a prior art needle hub 12 said needle hub 12 comprising a hypodermic at least one flange 1 for attaching the needle hub 12 to a male luer fitting, on one side a needle nest 4 for fixedly attaching the needle (not shown) said needle nest 4 having at least one, or a plurality of fins 2 and an inner aperture creating a fluid/gaseous path between the needle hub 12 and the needle. The invention is shown being retrofitted to said prior art hub 12, said attachment means comprising a spin weld, sonic weld, heat weld, or mechanical attachment means as shown by the protrusion 64 being attached by means of a snap fit or friction fit, said needle nest 4 having a recess or slot manufactured to accept said protrusion 64 of hub portion 15, said hub portion 15 having a protrusion 5 located at the distal end of the hub portion 15, said protrusion 5 being connected at the distal end of the hub portion 15, said hub portion 15 also having a section 16 for removably attaching a protective storage covers (not shown) said section 16 also having a means for creating a tortuous path preventing contamination from entering the sterile field created by enclosing the needle 10, needle guard 22 and hub portion 15 within a protective storage cover. Hub portion 15 includes a moveable latching arm or lever 26 attached to the hub portion 15 by a hinge section 23, with the moveable latching arm 26 having finger pad or button 27, a protrusion 21 for retaining a component in a releasably held position adjacent to the hub portion 15, said latching arm 26 also having a protrusion 49 for biasing the latching arm 26 in an outward manner when a compressive force is applied to the releasably held needle guard 22 with said moveable latching arm 26 shown in the preferred position for retaining at least one component in a retained position on the hypodermic needle hub 12.

FIG. 50 is a cross-sectional side view of the invention attached to a prior art glass pre-filled syringe 6 having a nest bead 7 and a hypodermic needle 10 showing the disclosed invention attached to said glass pre-filled syringe 6. Hub body 15 is fixedly attached to syringe 6 at the nest bead 7 by the attaching section 65; said hub body 15 having a protrusion 5 located at the distal end of said hub portion 15, said protrusion 5 being connected at the distal end of the hub portion 15, said hub portion 15 having a fixedly attached tether 24, said hub body 15 also having a section 16 for removably attaching a protective storage cover a moveable latching arm or lever 26 attached to the hub body 15 by a hinge section 23, said lever 26 having a touch pad 27, a protrusion 21 for retaining a component in a releasable position on the hub portion 15, said latching arm 26 also having a protrusion 49 for urging said latching arm 26 in an outward manner when a compressive force is applied to a releasably held needle guard with said moveable latching arm 26 shown in the preferred position for retaining at least one component in a retained position on the hub portion 15.

FIG. 51 is a cross-sectional side view of the invention attached to a prior art pre-filled cartridge syringe hub 8a having a fixedly attached needle 10 with a sharpened proximal end 111 and a sharpened distal end, said sharpened proximal end 111 for piercing the stopper of a medicine or fluid cartridge. Hub portion 15 is fixedly attached to said syringe hub 8a at the needle nest 4 said hub portion 15 having a protrusion 5 located on said hub portion 15, said protrusion 5 having an attachment section 17 with an aperture for inserting a tether (not shown), said attachment section 17 having a chamfered face on the proximal side to eliminate any possibility of the tether catching and hanging up on said attachment section 17 when said needle guard is released from a retained position, said hub portion 15 also having a section 16 for removably attaching a protective storage cover and a moveable latching arm or lever 26 with a touch pad 27 attached to the hub portion 15 by a hinge section 23, with the moveable latching arm 26 having a protrusion 21 for retaining a component in a releasably held position on the hub portion 15, said latching arm 26 also having a protrusion 49 for urging the latching arm 26 in an outward manner when a compressive force is applied to a releasably held needle guard with said moveable latching arm 26 shown in the preferred position for retaining at least one component in a retained position on the hub body 15.

FIG. 52 is a cross-sectional side view of the invention integrally molded to a pre-filled cartridge syringe hub 8b having a fixedly attached needle 10 with a sharpened proximal end 111 and a sharpened distal end (not shown) said sharpened proximal end 111 is for piercing the stopper of a medicine or fluid cartridge. Integral hub portion 15 having a needle nest 4, protrusion S located on said hub portion 15, said protrusion 5 having an attachment section 17 with an slot for inserting a tether (not shown) said attachment section 17 having an chamfered face on the proximal side to eliminate any possibility of the tether 24 catching and hanging up on said attachment section 17, said hub portion 15 also having a section 16 for removably attaching a protective storage cover, a moveable latching arm or lever 26 attached to the hub portion 15 by a hinge section 23, with the moveable latching arm 26 having a protrusion 21 for retaining a component in a releasable position adjacent to the hub portion 15, said latching arm 26 also having a protrusion 49 for urging the latching arm 26 in an outward manner when a compressive force is applied to a releasably held needle guard 22 (shown in other drawings in this application), with said moveable latching arm 26 shown in the preferred position for retaining at least one component in a retained position on the hub portion 15.

Figure 53:
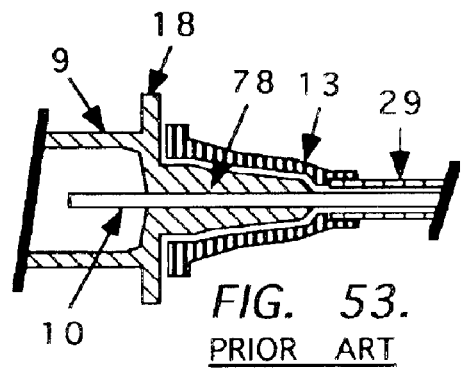
FIG. 53 is cross sectional side view of a prior art I.V. catheter adapter.

FIG. 53 is a cross-sectional side view drawing of a prior art indwelling intravenous (I.V.) catheter 29 having a catheter mounting section 9 with a section 18 for removably attaching a protective storage cover, a fixedly attached hypodermic needle 10, and a male section 78 for removably attaching an indwelling I.V. catheter hub 13.

Figure 54:
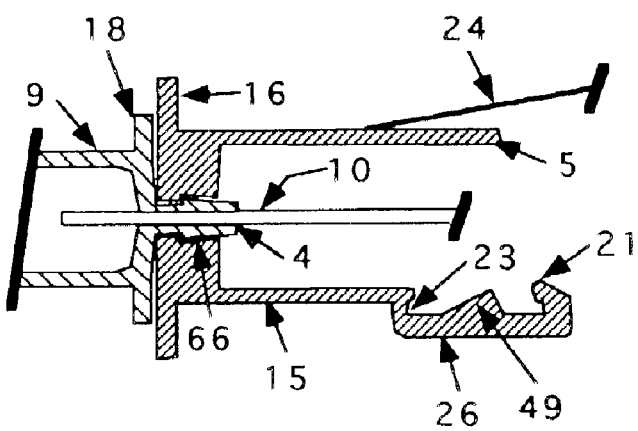
FIG. 54 shows the present invention retrofitted to an I.V. catheter adapter.

FIG. 54 is a cross-sectional side view an I.V. catheter having a mounting section 9, a section 18 for removably attaching a protective storage cover a hypodermic needle 10 being fixedly attached to a needle nest 4; said catheter mounting section 9 being retrofitted with the present invention. The invention comprises a hub portion 15 being fixedly attached to said catheter mounting section 9 at the nest 4 by the attaching section 66, said hub portion 15 having a protrusion 5 located at the distal end of said hub portion 15, said protrusion 5 being connected to the hub portion 15, said hub portion 15 having a fixedly attached tether 24, said hub portion 15 also having a section 16 for removably attaching a protective storage cover, a moveable latching arm or lever 26 attached to the hub portion 15 by a hinge section 23, with the moveable latching arm 26 having a protrusion 21 for retaining a component in a releasable position on the hub portion 15, said latching arm 26 also having a protrusion 49 for urging the latching arm 26 in an outward manner when a compressive force is applied to the releasably held needle guard (not shown), with said moveable latching arm 26 shown in the preferred position for retaining at least one component in a retained position on the hub portion 15.

Figure 55:
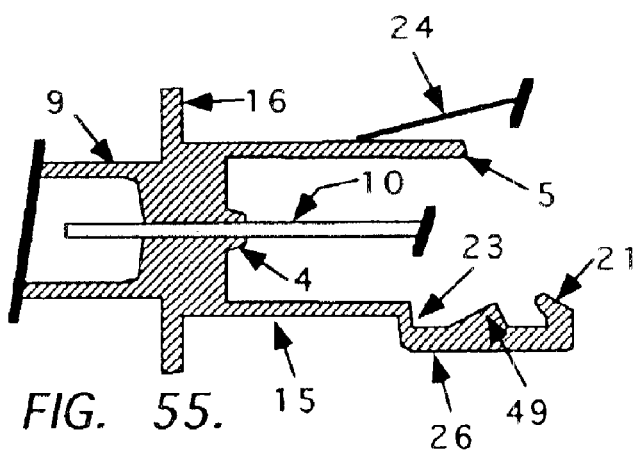
FIG. 55 shows the present invention integrally molded to an I.V. catheter adapter.

FIG. 55 is a cross-sectional side view of the present invention integrally molded to an I.V. catheter mounting section 9.

FIG. 56 illustrates a hub portion 15 of the present invention that may be attached to a blood collection device similar to that showing FIG. 25.

FIG. 57 is a full front view of the needle guard assembly 22 of FIG. 11 further comprising at least one fin 63 protecting the movement of said latching arm 26, allowing said latching arm 26 to freely disengage when the needle guard 22 is moved towards the hub 12 when said needle guard 22 contacts the protrusion 49.

FIG. 58. is a cross-sectional side view of a prior art pre-filled syringe cartridge comprising a glass cartridge 6, a glass cartridge hub 68 having a needle nest 4 for fixedly attaching a needle 10, said needle 10 having a sharpened distal end 11 said hub 68 also having a threaded section 67.

FIG. 59 is a cross sectional side view of the invention being threadedly attached to a glass cartridge hub 68, said glass cartridge 25 hub 68 being fixedly attached to a glass cartridge 6, said hub 68 having a needle nest 4 for fixedly attaching a needle 10, said needle 10 having a sharpened distal end (not shown) said hub 68 also having a threaded section 67. Hub body 15 is fixedly attached to said glass cartridge hub 68 by the threaded section 67, said hub 15 having a protrusion 5 located at the distal end of said hub portion 15, said protrusion 5 being connected at the distal end of the hub portion 15, said hub portion 15 having a fixedly attached tether 24. Hub body 15 also includes a section 16 for removably attaching a protective storage cover (FIGS. 78 and 79), a moveable latching arm or lever 26 with a touch pad 27 attached to the hub body 15 by a hinge section 23, with the moveable latching arm 26 having a protrusion 21 for retaining a component in a releasable position on the hub portion 15, said latching arm 26 also having a protrusion 49 for urging said latching arm 26 in an outward manner when a compressive force is applied to a releasably held needle guard with said moveable latching arm 26 shown in the preferred position for retaining at least one component in a retained position on the hub body 15.

FIG. 60 is a cross sectional side view of the invention being fixedly attached to a glass cartridge 6, comprising a hub 69 having a needle nest 4 for fixedly attaching a needle 10, a hub portion 15 being integrally molded to said hub 69; said hub portion 15 having a protrusion 5 located at the distal end of said hub portion 15, said protrusion 5 being connected at the distal end of the hub portion 15, said hub portion 15 having a fixedly attached tether 24, said tether 24 could also be fixedly attached to section 16, said hub 69 also having a section 16 for removably attaching a protective storage cover, a moveable latching arm or lever 26 attached to the hub portion 15 by a hinge section 23, with the moveable latching arm 26 having a protrusion 21 for retaining a component in a releasable position on the hub portion 15, said latching arm 26 also having a protrusion 49 for urging said latching arm 26 in an outward manner when a compressive force is applied to a releasably held needle guard 22, with said moveable latching arm 26 shown in the preferred position for retaining at least one component in a retained position on hub 69.

FIG. 61 is a cross sectional top view of the invention shown on an indwelling catheter 29 embodiment, having a movable needle guard 22a and a separable indwelling I.V. catheter 29, said catheter 29 being fixedly attached to a catheter hub 13, an I.V. catheter mounting section 9 having a fixedly attached hollow bore hypodermic needle 10 having a sharpened distal end 11; a hub portion 15 having a section 16 for removably attaching a protective storage cover 54, a slidable needle guard 22a being fixedly attached to said hub portion 15 by means of a limiting tether, said needle guard 22a having a projection or finger post 80 for advancing said separable catheter 29 and said needle guard 22a along said hypodermic needle 10 so said catheter may be inserted into a blood vessel, said hypodermic needle 10 being slidable through a guide aperture 47 in said movable needle guard 22a, said needle guard 22a having a movable needle trap 41 with a corresponding slot 31 for receiving the needle trap 41 when said trap 41 moves beyond the needle tip 11, said needle guard 22a having an open collar or washer 30 for retaining the resilient member 19 on the proximal end of said needle guard 22a, said resilient member 19 being slidably held on said needle guard 22a by the notch or indentation 60, said movable needle trap 41 having a lead-in area 33 for locating said resilient member 19 on said needle guard 22a into notches 60 and/or 61, said needle trap 41 also having a notch or indentation 61 for retaining said end coils of said resilient member 19, with the distal end of said needle guard 22a having a male section 78 for removably attaching an indwelling I.V. catheter hub 13, with a section of said male section 78 having a movable arm 42 for releasably retaining a catheter hub 13 from said male section 78 during initial insertion of the catheter 29 into a patient. Said catheter hub 13 having an inner channel, recess, slot or undercut 32 for being releasably held by said movable arm 42. Said movable arm 42 could also comprise a metal component which is inserted during or after said male section 78 is manufactured.

Said hub portion 15 could also comprise the latching arm 26 shown in other drawings in this application, otherwise said needle guard 22a would be releasably held adjacent to said hub portion 15 prior to use by a frictional or wedged means. FIG. 62 is a cross sectional top view of the movable needle guard 22a shown in FIG. 61 on an indwelling catheter embodiment, containing the elements shown and described in the movable needle guard 22a, whereby the catheter 29 has been inserted in a blood vessel and the needle 10 is being retracted into said needle guard 22a as the needle 10 is being pulled away from said catheter insertion site, whereby the movable arm 42 on the male section 78 is free to move where the needle has been residing within the distal male section 78 of the needle guard 22a, allowing the catheter hub 13 to remain in the blood vessel and freely separate from the needle guard 22a, with the needle trap 41 sliding on said needle 10. The needle guard 22a is attached to the hub portion 15 shown in FIG. 61 whereby a fixedly attached tether (not shown) limits the forward movement of the needle guard 22a, safely trapping the needle tip 11.

Said catheter hub 13 having an inner channel, recess, slot or undercut 32 for being releasably held by said movable arm 42.

FIG. 63 is a cross sectional top view of the movable needle guard 22a shown in FIGS. 61 and 62 on an indwelling catheter 29 embodiment, containing the elements shown and described in FIGS. 61 and 62, including the movable needle guard 22a, a tether (not shown) and catheter 29, whereby the catheter 29 has been inserted in a blood vessel and the needle 10 is safely retracted within said needle guard 22a where by the movable arm 42 has moved inwardly releasing the hold on the catheter hub 13, with the needle trap 41 now safely trapping the needle tip 11. Movable arm 42 includes a corresponding receiving slot 166 for receiving said movable arm 42. Said needle guard 22a having said movable needle trap 41 located within the corresponding slot 31 after said trap 41 has moved beyond the needle tip 11. Said needle guard 22a is attached to the hub portion 15 as shown in FIGS. 61 and 62 whereby a tether limits the forward movement of the needle guard 22a, safely trapping the needle tip 11. Said catheter hub 13 having an inner channel, recess, slot or undercut 32 for being releasably held by said movable arm 42.

The movable arm protrusion 42 can comprise a "v" shaped configuration which allows the catheter hub 13 to separate even in the event the movable arm 42 has taken a set during storage. A set during storage could inhibit the separation of said catheter hub 13 from said mounting section 78.

FIG. 64 is a cross-sectional side view of the present invention ready for use on a male luer syringe. FIG. 64 shows a full view of the hypodermic needle 10 comprising: a hub 12 with a fixedly attached needle 10, a means for retaining a separate, movable needle guard 22, said needle guard 22 having an aperture therethrough for said hypodermic needle 10, whereby the needle guard 22 is retained in a ready to use position on said hub 12, with said retained needle guard 22 being urged away from said needle hub 12 by a compressed resilient member 19, said resilient member 19 being located between, among or amid said hub 12 and said needle guard 22, said resilient member 19 also being located in an annular fashion surrounding a portion of said needle guard 22, said needle guard 22 is fixedly attached to said needle hub portion 15 by means of a limiting tether 24.

Said hub 12 having an aperture therethrough creating a fluid/gas path to said hypodermic needle 10, at least one flange 101 for attaching the needle hub 12 to a male luer fitting, a needle nest 4 for fixedly attaching the needle 10, said needle 10 having a sharpened distal end 11 and an unsharpened proximal end being fixedly attached to said hub 12 and an integral hub portion 15 having a protrusion 5 located at the distal end of said hub body 15, said protrusion 5 being connected to the hub portion 15, said protrusion 5 having a fixedly attached tether 24, said hub portion 15 also having a section 16 for removably attaching a protective storage cover, a moveable latching arm or lever 26 with a touch pad 27 attached to the hub portion 15 by a hinge section 23, with the moveable latching arm 26 having a protrusion 21 for retaining a component in a releasably retained position on the hub portion 15, said latching arm 26 also having a protrusion 49 for biasing the latching arm 26 in an outward manner when a compressive force is applied to the releasably held needle guard 22; and a movable needle guard 22 having a proximal guide section 34, an internal guide section 35, with a recess or void 38 residing between said proximal guide section 34 and said internal guide section 35, a distal needle guide aperture 47, a receiving slot 31 to receive the needle trap 41 (not shown), a retaining area 44*a* with an aperture 48 to receive said protrusion 21, said needle guard 22 having a compressed resilient member 19 positioned at the proximal end of said needle guard 22 said with the resilient member 19 exerting an extending force on said needle guard 22; with said needle guard 22 being releasable held in a compressed position by the protrusion 21 of the moveable latching arm 26 on said hub portion 15, an aperture for orienting said needle guard assembly 22 adjacent to said hub portion 12, said aperture having the hub protrusion 5 positioned therethrough, said latching arm 26 having a protrusion 49 for engaging said needle guard assembly 22 when said needle guard 22 is urged toward said hub portion 12, said needle guard 22 engages protrusion 49 and manually moves said latching arm 26 in an outward manner ensuring said latching arm 26 moves outwardly releasing the hold on the needle guard assembly 22.

FIG. 65 is a cross sectional top view of FIG. 64 containing the elements shown and described in FIG. 64 with the releasably held needle guard assembly 22 being releasably held adjacent to said hub portion 15, said guard assembly 22 being movable by the stored energy present in the compressed resilient member 19, said resilient member 19 being slidably retained on said needle guard 22 by the notch or indentation 60, said movable needle trap 41 having a lead-in area 33 for locating said resilient member 19 on said needle guard 22 into notches 60 and/or 61, said needle trap 41 also having at least one notch or indentation 61 for releasably retaining said end coils of said resilient member 19, said needle guard 22 having a proximal guide section 34, a distal needle guide aperture 47, a needle trap 41 biasly contacting said hypodermic needle 10 by the inherent memory of the molded configuration of said needle trap 41 and/or the extending force of the surrounding resilient member 19, whereby the advancing movement of said needle guard 22 is limited by a fixedly attached tether 24 (not shown), said needle 10 having a sharpened distal end 11 and an unsharpened proximal end being fixedly attached to said hub 12. Said needle trap 41 being hingedly attached to said needle guard 22 by a hinge section 40, said needle guard 22 having a receiving slot 31 to receive the needle trap 41, a distal needle guide aperture 47.

FIG. 66 is a cross sectional top view of FIGS. 64 and 65 containing the elements described in FIGS. 64 and 65 with the releasably held needle guard assembly 22 being urged toward the distal end of the hypodermic needle 10 by the extending force of the resilient member 19, having a needle trap 41 biasly contacting said hypodermic needle 10 by the inherent memory of the molded configuration of said needle tip guard 41 and/or the extending force of the surrounding resilient member 19, whereby the advancing movement of said needle guard 22 is limited by a fixedly attached tether (not shown). Said resilient member 19 being slidably retained on said needle guard 22 by the notch or indentation 60, said movable needle trap 41 having a lead-in area 33 for locating said resilient member 19 on said needle guard 22 into notches 60 and/or 61, said needle trap 41 also having at least one notch or indentation 61 for releasably retaining said end coils of said resilient member 19. Said needle trap 41 being hingedly attached to said needle guard 22 by a hinge section 40, said needle guard 22 having an integral metal guard 75 and a distal needle guide aperture 47. Said needle guard 41 also having a tapered or reducing proximal section 304 for non-binding access by the movable resilient member 19. Said resilient member 19 being movably positioned in an annular manner about or around the proximal section of said needle guard 22.

FIG. 67 is a cross sectional top view FIGS. 64, 65 and 66 showing the needle tip 11 being trapped within the needle guard 22 by the movable needle guard 41, comprising a hypodermic needle 10 having a sharpened tip 11, said needle guard 22 being movably attached to said hub portion by means of a limiting tether (not shown), with the resilient member 19 extended and maintaining an extending force on the needle guard assembly 22, said needle guard is prevented from advancing further by the limiting feature of said limiting tether, said needle guard 22 having only one notch 60 for maintaining an extending force of said resilient member 19 on said needle guard 22, said needle guard 22 maintaining alignment on said hypodermic needle 10 by means of the guide sections shown throughout this application. Said proximal guide 34 is shown here maintaining the needle guard 22 in a substantially concentric manner on said hypodermic needle 10. Said needle guard 41 also having a tapered or reducing proximal section 304 for non-binding access by the movable resilient member 19.

FIG. 68 is a full side view of the invention without the needle 10, comprising a hub 12 that is attachable to a male luer fitting, said hub 12 having at least one flange 101 at the proximal end a hub portion 15, said hub portion 15 having a protrusion 5, a protrusion 17 having an aperture for attaching a tether 24, a movable latching arm 26 having a hook 21 and a protrusion 49, said latching arm 26 being hingedly attached to said hub portion 15 by a hinge 23, with said tether 24 being fixedly attached to a movable needle guard 22, said needle guard 22 having a movable needle trap 41 being hingedly attached to said needle guard 22 by the hinge 40, said needle trap 41 having at least one notch or multi-level landing 61 for proper positioning of a resilient member 19 (not shown), said needle trap 41 having a lead in section 33 also for locating said resilient member 19 in a compressed and/or extendible position, said needle guard 22 having a protrusion 44*a* for maintaining a releasable hold on said needle guard 22 when said needle guard 22 is retained adjacent to said hub portion 15 by said latching arm 26 and hook 21, said needle trap having a different, or brightly colored indicator 64 which is visible only when the resilient member is retained in a compressed positioned on said needle guard 22 before the needle guard 22 is activated. The resilient member covers said indicator 64 shielding said indicator 64 from view when the needle guard 22 is activated and said resilient member 19 is extended around said needle guard 22 and the movable needle trap 41. Said resilient member 19 maintains said needle trap 41 in a protective position on said needle guard 22. Said indicator 64 could easily be located anywhere on said needle guard 22 where the advancing resilient member 19 hides the indicator 64 from view alerting the user that the device is safely shielding the sharpened needle tip 11 thus preventing an unintentional percutaneous needlestick injury.

FIG. 69 is a full, outside, top view of the needle guard assembly 22 shown in its molded configuration comprising a foldable, open-faced needle guard 22 having a hinge section 28, with adjacent lands 39 which create an aperture when said needle guard assembly 22 is coupled together, a front section 62, at least one fin 63 for allowing adequate clearance for a latching arm to freely be urged from a releasably holding position on said needle guard 22 when the invention is activated during use. A slot or void 25 is created when the needle guard 22 sections are joined together. A retaining protrusion 44*b* is located adjacent to said slot 25, said retaining protrusion 44*b* interfaces with the hook of a latching arm (not shown), a notch 60 for positioning and maintaining the extending force of a resilient member on said needle guard 22 when said guard 22 is in a retained and extending mode, a tapered or reduced proximal end 45 for eliminating any binding effect caused when the resilient member moves around or about the proximal end of said needle guard 22, said needle guard 22 having a movable needle trap 41 being hingedly attached to said needle guard by the hinge 40, said needle trap 41 having at least one notch or multi-level landing 61 for proper positioning of a resilient member said needle trap 41 having a lead in section 33 also for locating said resilient member in a compressed and/or extendible position. Said needle trap 22 being fixedly attached to a tether 24, said tether having at least one protrusion 20 for fixedly attaching said tether 24 to said hub portion 15 or hub 12, or flange 16.

FIG. 70 is a view of the proximal end of the tether 24 having a plurality of protrusions 20*a* for fixedly attaching said tether 24 to said hub portion 15 or hub 12, or flange 16.

FIG. 71 is a is a full, inside face view of the needle guard assembly 22 shown in its molded configuration comprising a foldable, open-faced needle guard 22 having a hinge section 28, with adjacent lands 39 which create an aperture when said needle guard assembly 22 is coupled together, a slot or void 25 is created when the needle guard 22 sections are joined together, a distal guide section 47 is also created when the needle guard 22 sections are joined together, a retaining protrusion ramp 44*c* is located adjacent to said slot 25, said retaining protrusion interfaces with the hook 21 of the latching arm 26 (both shown in other drawings in this application), said needle guard 22 having a movable needle trap 41 being hingedly attached to said needle guard by the hinge 40, said needle trap 41 having at least one skirt or fin 46 for entrapping said sharpened needle tip 11 (see FIG. 75), said needle guard having a corresponding slot or opening 31 for receiving said needle trap 41, said needle guard 22 having at least one pin 36 and a corresponding opening 37 for frictionally engaging said needle guard 22 sections together about a hypodermic needle, said pin 36 and slot 37 can be positioned on either side of needle guard 22 sections, said needle guard 22 having an internal guide section 35 and a proximal guide section 34 with a void or space 38 between said guides 34 and 35, said needle trap having an internal landing 52 located between said internal guide 35, with said landing 52 having an adjacent landing 53 which serves to guide the hypodermic needle during assembly, storage and use, said landing 53 also houses said sharpened needle tip within said needle guard 22. Said needle guard 22 being fixedly attached to a tether 24. Said tether 24 having at least one protrusion 20 for fixedly attaching said tether 24 to said hub portion 15 or hub 12, or flange 16.

FIG. 72 is a full front view of the needle guard assembly 22 shown in an open-faced configuration comprising a needle guard assembly 22 having an internal guide section 35, a hinge section 28 with a plurality of needle guard 22 sections connected adjacent to said hinge section 28, said hinge section 28 having an adequate area for insert molding a separate tether or fixedly attaching a separate tether, said hinge section 28 also could have an aperture therethrough for fixedly inserting a separate tether, said needle guard 22 having a split line 43 where the needle guard 22 sections mate or join together, an aperture guide 47 on each section at the distal end, a recess 25 on one section having a protrusion 98*a* for joining with the corresponding element 98*b* on the other section of said needle guard assembly 22, and a post 36 for joining the needle guard assembly 22 sections together. Said post 36 is received by a corresponding slot or opening 37 (shown as a dotted line).

FIG. 73 is a full rear view of the needle guard assembly 22 shown in an open-faced configuration comprising a needle guard assembly 22 having a hinge section 28 joining each section, said hinge section 28 having a slot or recess for inserting a fixedly attached, separate tether (not shown), said hinge section 28 also having a fin 79 being hingedly attached to said hinge section 28, said fin 79 being bendable over said hinge section 28 for fixedly attaching a separate tether by a heat weld or press means, said needle guard 22 having a split line 43 where the needle guard 22 sections mate or join together, an aperture guide 34 on each needle guard 22 section, a protrusion 98*b* for joining with the corresponding element 98*b* on the alternate needle guard assembly 22 section, a moveable needle trap 41, at least one post or protrusion 36 on one needle guard assembly 22 section which enters at least one corresponding slot 37 on the other needle guard assembly 22 section for securing the sections together. Said post 36 is received by a corresponding slot or opening 37 (shown as a dotted line).

FIG. 74 is a full, inside face view of one half of the needle guard assembly 22 containing the elements shown and described in FIG. 71 showing said needle guard 22 in its molded configuration comprising a foldable, open-faced needle guard 22 having a hinge section 28 for attaching a separate tether with adjacent lands 39 which create an aperture when said needle guard assembly 22 is coupled together, a slot or void 25 is created when the needle guard 22 sections are joined together, a distal guide section 47 is also created when the needle guard 22 sections are joined together, said needle guard 22 having a corresponding slot or opening 31 for receiving said needle trap 41 (see FIG. 71), said needle trap having at least one pin 36 (see FIG. 71) and a corresponding opening 37 for frictionally engaging said needle guard 22 sections together about the hypodermic needle, said pin 36 and slot 37 (see FIG. 71) can be positioned on either side of needle guard 22 sections, said needle guard 22 having an internal guide section 35 and a proximal guide section 34 with a void or space 38 between said guides 34 and 35, said needle trap having an internal landing 52 located between said internal guide 35, with said landing 52 having an adjacent landing 53 which serves to guide said hypodermic needle during assembly, storage and use, said landing 53 also houses said sharpened needle tip within said needle guard 22. Said needle guard 22 being fixedly attached to a separate tether (not shown) at hinge section 28.

FIG. 75 is a cross sectional view of the needle guard 22 in FIG. 71 shown in axis 75—75 comprising a needle guard 22, a movable needle trap 41 and fins or skirts 46. Said skirts 46 maintain alignment of the trapped sharpened needle tip within said needle trap 41.

FIG. 76 is a cross sectional view of the needle guard 22 in FIG. 71 shown in axis 76—76 comprising a needle guard 22, a split line 43, a slot 37 and a landing 53.

FIG. 77 is a cross sectional view of the needle guard 22 in FIG. 74 shown in axis 77—77 comprising a needle guard 22, a split line 43, a guide section 35, said guide section 35 having chamfered or angled ends for aligning a hypodermic needle within said guide section 35 on said needle guard 22 during the assembly procedure, said hypodermic needle 10 (shown in other drawings in this application) resides adjacent to the landing 52.

FIG. 78 is a cross sectional side view of a hypodermic needle for use on a male luer syringe in a ready for use state in accordance with one embodiment of the present invention. The needle assembly is contained within a protective storage cover 54 and end cap 68, whereby needle 10, needle guard 22, resilient member 19, tether 24, hub 12 and flange 16 are held within said cover 54 by a wedging action of said flange 16 with the cover 54. FIG. 78 further illustrates a hub 12, a fixedly attached needle 10, a means for retaining a separate, movable needle guard 22, said needle guard 22 having an aperture therethrough for said hypodermic needle 10, whereby the needle guard 22 is retained in a ready to use position on said hub 12, with said retained needle guard 22 being urged away from said needle hub 12 by a compressed resilient member 19, said resilient member 19 being located between, among or amid said hub 12 and said needle guard 22, said resilient member 19 also being located in an annular fashion about or surrounding a portion of said needle guard 22, said needle guard 22 is fixedly attached to said needle hub portion 15 by means of a limiting tether 24.

Said hub 12 having an aperture therethrough creating a fluid/gas path to said hypodermic needle 10, at least one flange 101 for attaching the needle hub 12 to a male luer fitting, a needle nest 4 for fixedly attaching the needle 10, said needle 10 having a sharpened distal end 11 and an unsharpened proximal end being fixedly attached to said needle nest 4, and an integral hub portion 15 having a protrusion 5 located at the distal end of said hub portion 15, said protrusion 5 being connected to the hub portion 15, said hub portion 15 having a fixedly attached tether 24, said hub portion 15 also having a section 16 for removably attaching said protective storage cover 54, a moveable latching arm or lever 26 with a touch pad 27 attached to the hub portion 15 by a hinge section 23, with the moveable latching arm 26 having a protrusion 21 for retaining a component in a releasably held position adjacent or on said hub portion 15, said latching arm 26 also having a protrusion 49 for biasing the latching arm 26 in an outward manner when a compressive force is applied to said releasably held needle guard 22, said movable needle guard 22 having a proximal guide section 34, an internal guide section 35, with a recess or void 38 residing between said proximal guide section 34 and said internal guide section 35, a distal needle guard guide aperture 47, a receiving slot 31 to receive the needle trap 41 (not shown) a retaining area 44a with an aperture 48 to receive said protrusion 21, said needle guard 22 having a compressed resilient member 19 positioned at the proximal end of said needle guard 22 said with the resilient member 19 exerting an extending force on said needle guard 22; with said needle guard 22 being releasable held in a compressed position by the hook 21 of the moveable latching arm 26 on said hub portion 15, an aperture for orienting said needle guard assembly 22 adjacent to said hub portion 12, said aperture having the hub protrusion 5 positioned therethrough, said latching arm 26 having a protrusion 49 for engaging said needle guard assembly 22 when said needle guard 22 is urged toward said hub portion 12, said needle guard 22 engages protrusion 49 and mechanically urges said latching arm 26 in an outward manner ensuring said latching arm 26 moves outwardly releasing the hold on the needle guard assembly 22.

Said cover 54 having at least one internal projection 56, said projection holding said needle guard 22 and resilient member 19 in a retracted state during storage and prior to use, said cover 54 having a projection 55 for biasly holding or wedging said latching arm 26 in a retaining manner, said latching arm 26 releasably holding said needle guard 22 and said resilient member 19 in a retained position prior to use. The diameter of said cover 54 could also be sized to biasly hold said latching arm 26 in a retaining manner, therefore, eliminating the need for said projection 55.

A cap 68 is removably placed into or on said cover 54 to contain said needle assembly within said cover 54 and said cap 68, said cap 68 having a plurality of square shoulders 69, and a wall section 70 removably sealing said cover 54 and said cap 68 together at the tortuous path interface 71 maintaining a sterile field within said cover 54 and cap 68. Said projection 56 relieves the extending force of said resilient member 19 on said releasably held needle guard 22, said retaining latching arm 26 and said hinge 23 of said latching arm 26, by slightly compressing said resilient member 19, while said projection 55 holds said latching arm 26 in a wedged or confined position whereby said needle guard 22 is releasably held by said latching arm 26 when said cover 54 is removed from said needle assembly.

FIG. 79 is a cross sectional side view of the invention comprising a hypodermic needle for use on a pre-filled syringe or pre-filled cartridge syringe in a ready for use state having a needle guard 22 and hypodermic needle 10 being stored and retained in a protective storage cover 54, showing a full view of said hypodermic needle 10, said cover 54 having a means for retaining a separate, movable needle guard 22, said needle guard 22 having an aperture therethrough for said hypodermic needle 10, said needle 10 having a distal sharpened end 11, whereby the needle guard 22 is retained in a ready to use position, with said retained needle guard 22 being urged away from said prefilled syringe by a compressed resilient member 19, said resilient member 19 being located between, among or amid said prefilled syringe and said needle guard 22, said resilient member also being located in an annular fashion about or surrounding a portion of said needle guard 22, said needle guard 22 is fixedly attached to said needle hub portion 15 by means of a limiting tether 24.

Said integral hub portion 15 having a protrusion 5 located at the distal end of said hub portion 15, a moveable latching arm or lever 26 with a touch pad 27 attached to the hub portion 15 by a hinge section 23, with the moveable latching arm 26 having a protrusion 21 for retaining a component in a releasably held position adjacent to or on said hub portion 15, said latching arm 26 also having a protrusion 49 for urging said latching arm 26 in an outward manner when a compressive force is applied to said releasably held needle guard 22, said movable needle guard 22 having a proximal guide section 34, an internal guide section 35, a space or recess 38 between said proximal guide 34 and internal guide 35, a distal needle guard guide aperture 47, a receiving slot 31 to receive a needle trap 41 (not shown), a retaining area 44*a* with an aperture 48 to receive said protrusion 21, said needle guard 22 having a compressed resilient member 19 positioned at the proximal end of said needle guard 22 said with the resilient member 19 exerting an extending force on said needle guard 22; with said needle guard 22 being releasable held in a compressed position by the hook 21 of said moveable latching arm 26 on said hub portion 15, an aperture for orienting said needle guard assembly 22 adjacent to said hub portion 12, said aperture having the hub protrusion 5 positioned therethrough, said latching arm 26 having a protrusion 49 for engaging said needle guard assembly 22 when said needle guard 22 is urged toward said pre-filled syringe, said needle guard 22 engages protrusion 49 and mechanically urges said latching arm 26 in an outward manner ensuring said latching arm 26 moves outwardly releasing the hold on the needle guard assembly 22.

Said cover 54 having a soft elastomeric or rubber seal 72 inside or within the closed end of said cover 54 which sealingly engages said sharpened tip 11 and said needle 10 of a pre-filled syringe or pre-filled cartridge against leakage.

FIG. 80 is a cross sectional view of the hub 12 contained within a storage cover 54 in axis 80—80 of FIG. 78 and comprising a hub section 12, a storage cover 54 having at least one vane 57 for gripping a flange shoulder of said hub 12 so the needle 10, said hub 12 and said needle guard 22 can be safely turned or twistedly attached with the cover 54 on or off a medical device.

FIG. 81 is a cross sectional view of the needle 10 contained within a cover 54 in axis 81—81 of FIG. 79. Cover 54 includes at least one, or a plurality of internal projections 73, said projections 73 relieve the extending force of said resilient member 19 on said releasably held needle guard 22, said retaining latching arm 26 and said hinge 23 of said latching arm 26, by slightly compressing said resilient member 19 during storage.

FIG. 82 is a full front view of an open collar or washer 30 used with the indwelling I.V. catheter embodiment of the invention, said washer 30 retaining the resilient member 19 on the proximal end of the needle guard 22*a* on said catheter assembly shown in FIGS. 62, 63, and 64. Said washer having an angled entrance 63 for engaging said washer onto said needle guard 22*a*. Said washer 30 could comprise a flat configuration and be inserted into a corresponding slot on said needle guard 22*a* to hold said resilient member 19 on said needle guard 22*a*.

FIG. 83 is a cross sectional view of the washer 30 shown in along axis 83—83 in FIG. 82.

FIG. 84 is a cross sectional top view of the invention containing the elements shown and described in FIG. 64 having a movable metal needle trap 41 used to trap the sharpened needle tip 11 within said needle guard 22, comprising a hub 12 at least one proximal flange 101, a hub portion 15 and a flange 16 for wedgedly and removably attaching a protective cover, a releasably held needle guard assembly 22 being releasably held adjacent to said hub portion 15, said guard assembly 22 being movable by the stored energy present in the compressed resilient member 19, said resilient member 19 being slidably retained on said needle guard 22 by the notch or indentation 60, said metal needle trap 41 having a lead-in area 33 for locating said resilient member 19 on said needle guard 22 into notches 60 and/or 61, said needle trap 41 also having at least one notch or indentation 61 for releasably retaining said end coils of said resilient member 19, said needle guard 22 having a proximal guide section 34, a distal needle guide aperture 47, a metal needle trap 41 biasly contacting said hypodermic needle 10 by the inherent memory of the metal configuration of said needle trap 41 and/or the extending force of the surrounding resilient member 19, whereby the advancing movement of said needle guard 22 is limited by a fixedly attached tether (not shown), said needle 10 having a sharpened distal end 11 and an unsharpened proximal end being fixedly attached to said hub 12. Said needle trap 41 being hingedly inserted to said needle guard 22 at a hinge slot 40, said needle guard 22 having a receiving slot 31 to receive the needle trap 41, a distal needle guide aperture 47, said needle trap 41 having skirts 46 (shown in FIG. 75) to retain said sharpened needle end 11 within said metal needle trap 41.

Said needle trap 41 being insertable onto said needle guard 22 from the outside of said needle guard, allowing said needle trap 41 to be inserted onto said needle guard 22 either before or after said needle guard 22 is clasped around said hypodermic needle 10 from the side during assembly procedures.

FIG. 85 is a cross sectional top view of the invention containing the elements shown and described in FIGS. 64 and 84 having a movable metal needle trap 41 used to trap the sharpened needle tip 11 within said needle guard 22, comprising a hub 12 at least one proximal flange 101, a hub portion 15 and a flange 16 for wedgedly and removably attaching a protective cover, a releasably held needle guard assembly 22 being releasably held adjacent to said hub portion 15, said guard assembly 22 being movable by the stored energy present in the compressed resilient member 19, said resilient member 19 being slidably retained on said needle guard 22 by the notch or indentation 60, said metal needle trap 41 having a lead-in area 33 for locating said resilient member 19 on said needle guard 22 into notches 60 and/or 61, said needle trap 41 also having at least one notch or indentation 61 for releasably retaining said end coils of said resilient member 19, said needle guard 22 having a proximal guide section 34, a distal needle guide aperture 47, a metal needle trap 41 biasly contacting said hypodermic needle 10 by the inherent memory of the metal configuration of said needle trap 41 and/or the extending force of the surrounding resilient member 19, whereby the advancing movement of said needle guard 22 is limited by a fixedly attached tether (not shown), said needle 10 having a sharpened distal end 11 and an unsharpened proximal end being fixedly attached to said hub 12. Said needle trap 41 being hingedly inserted to said needle guard 22 at a hinge slot 40*d*, said needle guard 22 having a receiving slot 31 to receive the needle trap 41, a distal needle guide aperture 47, a receiving slot 31 to receive the metal needle trap 41, said needle trap 41 having skirts 46 (shown in FIG. 75) to retain said sharpened needle end 11 within said metal needle trap 41.

Said needle trap 41 being insertable onto said needle guard 22 from the inside of said needle guard, allowing said needle trap 41 to be inserted onto said needle guard 22 before said needle guard 22 is clasped around said hypodermic needle 10 from the side during assembly procedures.

FIG. 86 is a graph depicting the interaction of a resilient member and a sliding member, said sliding member being on an elongated shaft, said sliding member having a movable arm being urged away from said resilient member by an extending force, said moveable arm being movably wedged between the diameter of said resilient member and said shaft, said arm slidably contacting said shaft, and where another area of said resilient member is positioned around said sliding member, said resilient member being releasably retained by said movable arm on said sliding member, said resilient member having a portion of said sliding member within said resilient member's inside diameter, whereby the binding force of said resilient member on said sliding member and said movable arm eventually exceeds the extending force of said resilient member as said resilient member extends. Said extending force of said resilient member is greatest when said resilient member is completely compressed, and conversely, said extending force of said resilient member is weakest when said resilient member is completely elongated. The binding force of said resilient member on said movable arm is greatest when said resilient member is compressed.

FIG. 87 is a graph depicting the interaction of a resilient member and a sliding member, said sliding member being on an elongated shaft, said sliding member having a movable arm being urged away from said resilient member by an extending force, said moveable arm being movably wedged between the diameter of said resilient member and said shaft, said arm slidably contacting said shaft, and where another area of said resilient member is positioned in a notch or recess on said sliding member, said resilient member being releasably retained by said movable arm and said notch on said sliding member, said resilient member having a portion of said sliding member within said resilient member's inside diameter, whereby the binding force of said resilient member on said sliding member and said movable arm is always less than the extending force of said resilient member as said resilient member extends. Said extending force of said resilient member is exerted in the land created by said notch, maintaining a greater extending force on said sliding member and said movable arm than said binding force of said resilient member. Said movable arm is urged inwardly from a retaining position when said sliding member advances beyond the end of said shaft, thereby releasing the hold on said resilient member.

FIG. 88 is a cross-sectional side view of the present invention ready for use on a male luer syringe showing a full view of the hypodermic needle 10, and a cross sectional view of the releasing means shown and described in FIG. 48A comprising a hub 412 with a fixedly attached needle 10, a means for retaining a separate, movable needle guard 22, said needle guard 22 having an aperture therethrough for said hypodermic needle 10, whereby the needle guard 22 is retained in a ready to use position on said hub 412, with said retained needle guard 22 being urged away from said needle hub 412 by a compressed resilient member 19, said resilient member 19 being located between, among or amid said hub 412 and said needle guard 22, said resilient member 19 also being located in an annular fashion surrounding a portion of said needle guard 22, said needle guard 22 is fixedly attached to said needle hub portion 215 by means of a limiting tether 24.

Said needle guard 22 having a retaining means 77, said retaining means having an aperture 78 for releasably holding said needle guard 22 in a retained position adjacent to said hub portion 215, said needle guard 22 having a latching arm 81 being hingedly attached to said needle guard 22 at a hinge section 23, a protrusion 49 for urging said arm 81 from a releasably held position adjacent to said hub portion 215 when a compressive force is applied to said needle guard 22 and said protrusion 49 engages said retaining means 77 and mechanically releases said hold on said needle guard 22, said arm 81 having a protrusion 21 for releasably holding said arm 81 in said aperture 78 of said retaining means 77, said arm 81 having a finger pad 27 with projections which do not impede the movement of said pad 27 and said protrusion 21 through said aperture 78 as said needle guard 22 is urged away from said hub portion 215.

Said hub 412 having an aperture therethrough creating a fluid/gas path to said hypodermic needle 10, at least one flange 101 for attaching the hub 412 to a male luer fitting, a needle nest 4 for fixedly attaching the needle 10, said needle 10 a sharpened distal end 11 and an unsharpened proximal end being fixedly attached to said hub 412 and an integral hub portion 215 having a protrusion 5 located at the distal end of said hub portion 215, said protrusion 5 being connected to the hub portion 215, said protrusion 5 having a fixedly attached tether 24, said hub portion 215 also having a section 16 for removably attaching a protective storage cover said movable needle guard 22 having a proximal guide section 34, an internal guide section 35, with a recess or void 38 residing between said proximal guide section 34 and said internal guide section 35, a distal needle guide aperture 47, a receiving slot 31 to receive the needle trap 41 said needle guard 22 having a compressed resilient member 19 positioned at the proximal end of said needle guard 22 said with the resilient member 19 exerting an extending force on said needle guard 22; with said needle guard 22 being releasably held in a compressed position by the hook 21 of the moveable latching arm 81 on said needle guard 22, an aperture for orienting said needle guard assembly 22 adjacent to said hub portion 215, said aperture having the hub protrusion 5 positioned therethrough, said latching arm 81 having a protrusion 49 for engaging said retaining means 77 when said needle guard 22 is urged toward said hub portion 215, said needle guard 22 engages protrusion 49 and manually moves said latching arm 81 in an outward manner ensuring said latching arm 81 moves inwardly releasing the hold on the needle guard assembly 22.

FIGS. 89, 90 and 91 show a cross-section view of the invention described in FIGS. 84, 85 and 88, respectively, wherein hub 212 includes a threaded section 74 for attaching the hub to a blood collection device. (See FIG. 25.)

FIGS. 92, 93 and 94 show a cross-section view of the invention described in FIGS. 84, 85 and 88, respectively, being fixedly attached to a prefilled syringe.

Figure 95:
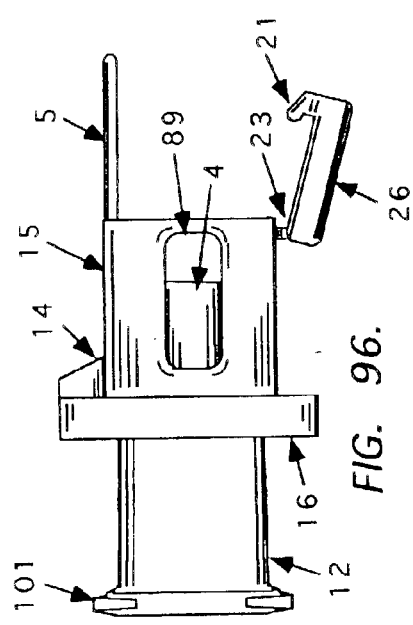
FIGS. 95 and 96 illustrates a full side view of a needle hub in one embodiment of the present invention.

FIG. 95 is a full side view drawing of the disclosed invention hub component 12, comprising a hypodermic needle hub 12 with a flange 101 for attaching the needle hub 12 to a male luer fitting, a needle nest 4, a section 16 for removably holding a protective storage cover over a hypodermic needle (not shown) a protrusion 5 located at the distal end of the hub portion 15, said hub portion 15 having at least one aperture 89 for inserting a glue carrying fixture or the like to apply glue to the needle during assembly, said aperture 89 also being a venting means to allow pneumatic pressure to escape during insertion of needle 10 with glue into said needle nest 4, said protrusion 5 being connected to the hub portion 15 at the distal end of the hub portion 15, said section 16 having a shoulder 14 for twistedly attaching said invention to a storage cover, and a moveable latching arm 26 with a finger pad 27, attached to the hub portion 15 by a hinge section 23, said finger pad 27 having at least one protrusion for creating a more positive grip or contact with said finger pad 27, said finger pad 27 also comprising a different, or bright color, which serves as a visual indicator for the user to easily locate the finger pad 27 for manual release of a needle guard assembly or the like, with the moveable latching arm 26 having a protrusion 21 for retaining a component in a releasable position adjacent to said hub portion 15, said moveable latching arm 26 shown in the preferred molded position.

Figure 96:
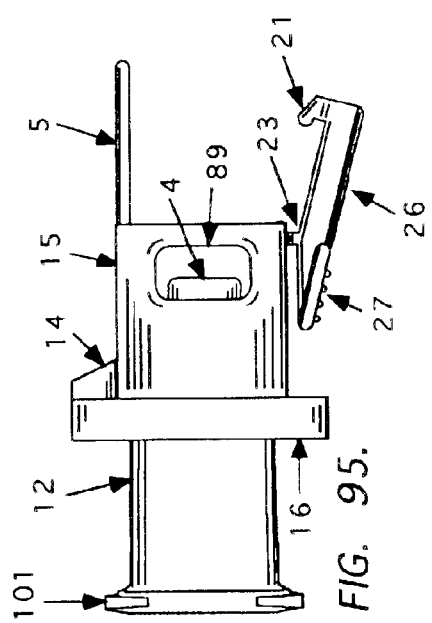

FIG. 96 is a full side view drawing of the disclosed invention hub component 12, comprising a hypodermic needle hub 12 with a flange 101 for attaching the needle hub 12 to a male luer fitting, a needle nest 4, a section 16 for removably holding a protective storage cover over the hypodermic needle (not shown), a protrusion 5 located at the distal end of the hub portion 15, said hub portion 15 having at least one aperture 89 for inserting a glue carrying fixture or the like to apply glue to said needle 10 during assembly, said aperture 89 also being a vent to allow pneumatic pressure to escape during insertion of needle 10 into said needle nest 4, said protrusion 5 being connected to the hub portion 15 at the distal end of the hub portion 15, said section 16 having a shoulder 14 for twistedly attaching said invention to a storage cover, and a moveable latching arm 26 attached to the hub portion 15 by a hinge section 23, with the moveable latching arm 26 having a protrusion 21 for retaining a component in a releasable position adjacent to said hub portion 15, said moveable latching arm 26 shown in the preferred molded position.

Figure 97:
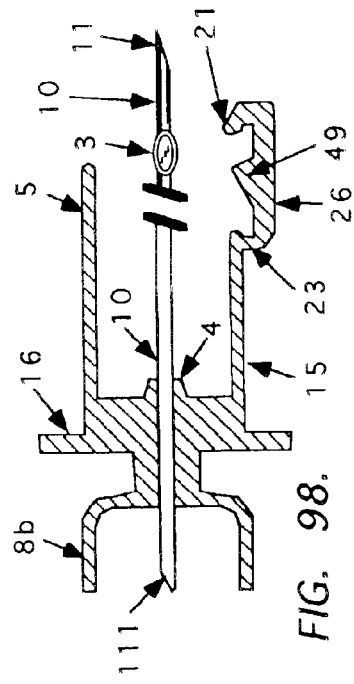

FIG. 97 is a cross-sectional side view of the invention attached to a prior art glass pre-filled syringe 6 having a nest bead 7 and a hypodermic needle 10 with a distal sharpened end 11, said needle 10 having a change in profile 3 near the distal end for limiting axial movement of a slidable needle guard 22 relative to the needle tip 11 after positioning the needle guard at the distal end of the needle 10. FIG. 97 further shows a hub body 15 being fixedly attached to said syringe 6 at the nest bead 7 by the attaching section 65; said hub body 15 having a protrusion 5 located at the distal end of said hub portion 15, said protrusion 5 being connected at the distal end of the hub portion 15, said hub body 15 also having a section 16 for removably attaching a protective storage cover, a moveable latching arm or lever 26 attached to the hub body 15 by a hinge section 23, said lever 26 having a touch pad 27, a protrusion 21 for retaining a component in a releasable position on the hub portion 15, said latching arm 26 also having a protrusion 49 for urging said latching arm 26 in an outward manner when a compressive force is applied to the releasably held needle guard 22 (shown in other drawings in this application), with said moveable latching arm 26 shown in the preferred position for retaining at least one component in a retained position on the hub portion 15.

Figure 98:
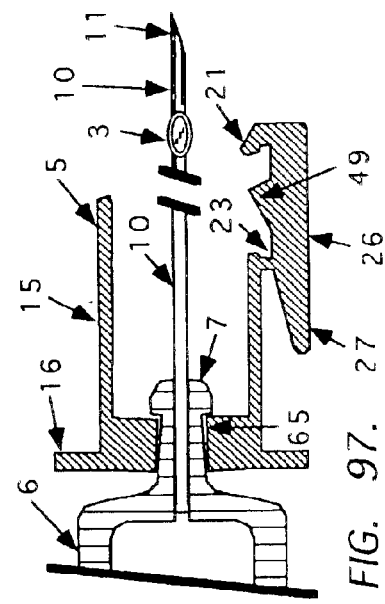

FIG. 98 is a cross-sectional side view of the invention integrally molded to a pre-filled cartridge syringe hub 8b having a fixedly attached needle 10 with a sharpened proximal end 111 and a sharpened distal end 11, said needle 10 having a change in profile 3 near the distal end for limiting axial movement of a slidable needle guard relative to the needle tip 11 after positioning said needle guard at the distal end of the needle 10, said sharpened proximal end 111 is for piercing the stopper of a medicine or fluid cartridge. The invention includes an integral hub portion 15, having a needle nest 4; said hub portion 15 having a protrusion 5 located on said hub portion 15, said hub portion 15 also having a section 16 for removably attaching a protective storage cover, a moveable latching arm or lever 26 attached to the hub portion 15 by a hinge section 23, with the moveable latching arm 26 having a protrusion 21 for retaining a component in a releasable position on the hub portion 15, said latching arm 26 also having a protrusion 49 for urging the latching arm 26 in an outward manner when a compressive force is applied to the releasably held needle guard 22 with said moveable latching arm 26 shown in the preferred position for retaining at least one component in a retained position on the hub portion.

FIG. 99 is a cross-sectional side view of the invention attached to a prior art pre-filled cartridge syringe hub 8a having a fixedly attached needle 10 with a sharpened proximal end 111 and a sharpened distal end 11, said needle 10 having a change in profile 3 near the distal end for limiting axial movement of a slidable needle guard (not shown) relative to the needle tip 11 after positioning a needle guard at the distal end of the needle 10, said sharpened proximal end 111 for piercing the stopper of a medicine or fluid cartridge. The invention includes a hub portion 15 being fixedly attached to said syringe hub 8a at the needle nest 4; said hub portion 15 having a protrusion 5 located on said hub portion 15, said hub portion 15 also having a section 16 for removably attaching a protective storage cover, a moveable latching arm or lever 26 with a touch pad 27 attached to the hub portion 15 by a hinge section 23, with the moveable latching arm 26 having a protrusion 21 for retaining a component in a releasably held position on the hub portion 15, said latching arm 26 also having a protrusion 49 for urging the latching arm 26 in an outward manner when a compressive force is applied to a releasably held needle guard, with said moveable latching arm 26 shown in the preferred position for retaining at least one component in a retained position on the hub body 15.

FIG. 100A is a cross-sectional side view an I.V. catheter introducer having a hub section 9, having a fixedly attached needle 10 with a sharpened distal end, said needle 10 having a change in profile 3 near the distal end for limiting axial movement of a slidable needle guard (not shown) relative to the needle tip 11 after positioning said needle guard 22 at the distal end of the needle 10, a section 18 for removably attaching a protective storage cover, a hypodermic needle 10 being fixedly attached to a needle nest 4; said catheter mounting section 9 being retrofitted with the present invention, wherein hub portion 15 is fixedly attached to said catheter mounting section 9 at the nest 4 by the attaching section 66, said hub portion 15 also having a section 16 for removably attaching a protective storage cover.

FIG. 100B is a cross-sectional side view of the present invention integrally molded to an I.V. catheter introducer comprising a hub 9, a hypodermic needle 10 being fixedly attached to a needle nest 4 said needle 10 having a sharpened distal end 11, said needle 10 having a change in profile 3 near the distal end for limiting axial movement of a slidable needle guard (not shown) relative to the needle tip 11 after positioning said needle guard 22 at the distal end of the needle 10, a hub portion 15, said hub portion 15 having a protrusion 5 located on said hub portion 15, said hub body 15 also having a section 16 for removably attaching a protective storage cover, a moveable latching arm or lever 26 attached to the hub portion 15 by a hinge section 23, with the moveable latching arm 26 having a protrusion 21 for retaining a component in a releasable position on the hub portion 15, said latching arm 26 also having a protrusion 49 for urging said latching arm 26 in an outward manner when a compressive force is applied to the releasably held needle guard with said moveable latching arm shown in the preferred position for retaining at least one component in a retained position on the hub portion 15.

FIG. 101 is a cross sectional side view of the invention being threadedly attached to a glass cartridge hub 68, said glass cartridge hub 68 being fixedly attached to a glass cartridge 6, said hub 68 having a needle nest 4 for fixedly attaching a needle 10, said needle 10 having a sharpened distal end 11, said needle 10 having a change in profile 3 near the distal end for limiting axial movement of a slidable needle guard relative to the needle tip 11 after positioning said needle guard 22 at the distal end of the needle 10, said hub 68 also having a threaded section 67 fixedly attaching hub body is to said glass cartridge hub 68 by the threaded section 67; said hub body 15 having a protrusion 5 located at the distal end of said hub portion 15, said protrusion 5 being connected at the distal end of the hub portion 15, said hub body 15 also having a section 16 for removably attaching a protective storage cover, a moveable latching arm or lever 26 with a touch pad 27 attached to the hub body 15 by a hinge section 23, with the moveable latching arm 26 having a protrusion 21 for retaining a component in a releasable position on the hub portion 15, said latching arm 26 also having a protrusion 49 for urging said latching arm 26 in an outward manner when a compressive force is applied to the releasably held needle guard 22 (shown in other drawings in this application), with said moveable latching arm 26 shown in the preferred position for retaining at least one component in a retained position on the hub body 15.

FIG. 102 is a cross sectional side view of the invention being fixedly attached to a glass cartridge 6, comprising a hub 68 having a needle nest 4 for fixedly attaching a needle 10, said needle 10 having a sharpened distal end 11, said needle 10 having a change in profile 3 near the distal end for limiting axial movement of a slidable needle guard relative to the needle tip 11 after positioning said needle guard 22 at the distal end of the needle 10, a hub portion 15 being integrally molded to said glass cartridge hub 69; said hub portion 15 having a protrusion 5 located at the distal end of said hub portion 15, said protrusion 5 being connected at the distal end of the hub portion 15, said hub body 15 also having a section 16 for removably attaching a protective storage cover, a moveable latching arm or lever 26 attached to the hub portion 15 by a hinge section 23, with the moveable latching arm 26 having a protrusion 21 for retaining a component in a releasable position on the hub portion 15, said latching arm 26 also having a protrusion 49 for urging said latching arm 26 in an outward manner when a compressive force is applied to the releasably held needle guard 22 (shown in other drawings in this application), with said moveable latching arm 26 shown in the preferred position for retaining at least one component in a retained position on the hub body 15.

FIG. 103 is a cross sectional top view of the invention shown on an indwelling catheter 29 embodiment, having a movable needle guard 22a and a separable indwelling I.V. catheter 29, said catheter 29 being fixedly attached to a catheter hub 13; a hub 9 having a fixedly attached hollow bore hypodermic needle 10 having a sharpened distal end 11, said needle 10 being fixedly attached to a hub portion 15 having a section 16 for removably attaching a protective storage cover, a slidable needle guard 22a being fixedly attached to said hub portion 15 by means of a limiting tether 24, said tether 24 being slidably disposed through an aperture on said hub 9, said needle guard 22a having a projection or finger post 80 for advancing said separable catheter 29 and said needle guard 22a along said hypodermic needle 10 so said catheter 29 may be inserted into a blood vessel, said hypodermic needle 10 being slidable through a guide aperture in said movable needle guard 22a, said needle guard 22a having a movable needle trap 41 with a corresponding slot 31 for receiving the needle trap 41 when said trap 41 moves beyond the needle tip 11, said needle guard 22a having an open collar or washer 30 for retaining the resilient member 19 on the proximal end of said needle guard 22a, said resilient member 19 being slidably held on said needle guard 22a by the notch or indentation 60, said movable needle trap 41 having a lead-in area 33 for locating said resilient member 19 on said needle guard 22a into notches 60 and/or 61, said needle trap 41 also having a notch or indentation 61 for retaining said end coils of said resilient member 19, with the distal end of said needle guard 22a having a male section 78 for removably attaching an indwelling I.V. catheter hub 13, said needle trap 41 having a movable arm 45 and projection 42 for releasably retaining a catheter hub 13 from said male section 78 after insertion of the catheter 29 into a patient. Said catheter hub 13 having at least one flange 301 and an inner channel, recess, slot or undercut 32 for being releasably held by said movable arm 42. Said movable arm 42 could also comprise a metal component which is inserted during or after said male section 78 is manufactured. Said channel 32 can comprise an annular, or segmented configuration.

Said hub portion 15 could also comprise the latching arm 26 shown in other drawings in this application, otherwise said needle guard 22a would be releasably held adjacent to said hub portion 15 prior to use by a frictional or wedged means. The disclosed invention is shown in a ready to use state in FIG. 103.

FIG. 104 is a cross sectional top view of the invention shown showing the catheter introducer needle tip 11 being withdrawn into the needle guard 22a. The catheter 29 and catheter hub 13 remain releasably held adjacent to said needle guard 22a as the needle 10 is being withdrawn from the catheter insertion site through the distal guide 47 of said needle guard 22a. This drawing shows said needle guard 22a being held within a housing or shroud 85. Said housing 85 having an inner chamber for receiving a resilient member 19 and a slidable needle guard 22a, said housing 85 also having exterior projections 86 serving as a non-slip gripping means, said projections 86 can be longitudinal, radial or the like, and may comprise any surface or contour which improves the hold by the user on said housing 85. Said housing 85 may also have an internal projection 88 for fixedly attaching said needle guard 22a within said housing 85, and internal fins 97 to concentrically locate said resilient member 19 within said housing 85. Said needle guard 22a being held within said housing 85 by a snap-fit means created by the wedge 66a and slot 66b at the proximal end of said needle guard 22a. Said housing 85 having a corresponding aperture to receive said wedge 66a and slot 66b, said aperture having a "lead-in" 96 for easy assembly of said guard 22a into said housing 85. Said housing also may have an internal ring or at least one projection 88 which correspondingly is received by a slot 89 in said needle guard 22a. Said slot 89 and projection 88 may be placed either on the guard 22a or housing 85.

Said slidable needle guard 22a being fixedly attached to a hub portion by means of a limiting tether 24, said hypodermic needle 10 being slidable through a proximal guide aperture 34 in said movable needle guard 22a, said needle guard 22a having a movable needle trap 41 with a corresponding slot 31 for receiving the needle trap 41 when said trap 41 moves beyond the needle tip 11, said needle guard 22a having a notch or indentation 60 for releasably holding said resilient member 19 on said needle guard 22a, said movable needle trap 41 having a lead-in area 33 for locating said resilient member 19 on said needle guard 22a into notches 60 and/or 61, said needle trap 41 also having a notch or indentation 61 for retaining said end coils of said resilient member 19, with the distal end of said needle guard 22a having a male section 78 for removably attaching an indwelling I.V. catheter hub 13, said needle trap 41 having a movable arm 45 and projection 42 for releasably retaining a catheter hub 13 from said male section 78 after insertion of the catheter 29 into a patient. Said catheter hub 13 having at least one flange 301 and an inner channel, recess, slot or undercut 32 for being releasably held by said movable arm 45 and said projection 42. Said movable arm 45 could also comprise a metal component which is inserted during or after said male section 78 is manufactured.

Said hub portion 15 could also comprise the latching arm 26 shown in other drawings in this application, otherwise said needle guard 22a would be releasably held adjacent to said hub portion prior to use by a frictional or wedged means.

FIG. 105 is a cross sectional and cut away top view of the movable needle guard 22a on an indwelling catheter 29 embodiment containing the elements shown and described in FIG. 104, showing the needle tip 11 being safely contained within the needle guard 22a with the arm 45 and projection 42 correspondingly moved inwardly and activated with the needle trap 41, including a few different versions of the components: said tether 24 being fixedly attached to the housing 85, said housing 85 having at least one longitudinal nonslip projection 86, said housing having a distal projection 90 which may snap over said needle guard 22a when said needle guard 22a is contained within said housing 85, said needle guard 22a having a split line 43, said projection 42 having a "v" shape. The shape of the projection 42 is not limited to a singular or double faced surface, but might be oval, round, radial, smooth or rough or a combination of any surfaces described herein.

FIG. 106 is a cross-sectional and cut away side view of the present invention ready for use on a male luer syringe shows a full view of the hypodermic needle 10 having a change in profile 3 near the distal end for limiting axially movement of a slidable needle guard 22 relative to the needle tip 11 after positioning said needle guard 22 at the distal end of the needle 10 comprising: a hub 12 with a fixedly attached needle 10, a means for retaining a separate, movable needle guard 22, said needle guard 22 having an aperture therethrough for said hypodermic needle 10, whereby the needle guard 22 is retained in a ready to use position on said hub 12, with said retained needle guard 22 being urged away from said needle hub 12 by a compressed resilient member 19, said resilient member 19 being located between, among or amid said hub 12 and said needle guard 22, said resilient member 19 also being located in an annular fashion surrounding a portion of said needle guard 22.

Said hub 12 having an aperture therethrough creating a fluid/gas path to said hypodermic needle 10, at least one flange 101 for attaching the needle hub 12 to a male luer fitting, a needle nest 4 for fixedly attaching the needle 10, said needle 10 a sharpened distal end 11 and an unsharpened proximal end being fixedly attached to said hub 12 and an integral hub portion 15 having a protrusion 5 located at the distal end of said hub body 15, said protrusion 5 being connected to the hub portion 15, said hub portion 15 also having a section 16 for removably attaching a protective storage cover, a moveable latching arm or lever 26 with a touch pad 27 attached to the hub portion 15 by a hinge section 23, with the moveable latching arm 26 having a protrusion 21 for retaining a component in a releasably retained position on the hub portion 15, said latching arm 26 also having a protrusion 49 for biasing the latching arm 26 in an outward manner when a compressive force is applied to the releasably held needle guard 22; and a movable needle guard 22 having a proximal guide section 34, a distal needle guide section 47 and a movable needle trap 41 (not shown in this view), a receiving slot 31 to receive the needle trap, a retaining area 44a with an aperture 48 to receive said protrusion 21, said needle guard 22 having a compressed resilient member 19 positioned at the proximal end of said needle guard 22 said with the resilient member 19 exerting an extending force on said needle guard 22; with said needle guard 22 being releasably held in a compressed position by the hook 21 of the moveable latching arm 26 on said hub portion 15, an aperture for orienting said needle guard assembly 22 adjacent to said hub portion 12, said aperture having the hub protrusion 5 positioned therethrough, said latching arm 26 having a protrusion 49 for engaging said needle guard 22 when said needle guard 22 is urged toward said hub portion 12, said needle guard 22 engages protrusion 49 and manually moves said latching arm 26 in an outward manner ensuring said latching arm 26 moves outwardly releasing the hold on the needle guard 22.

FIG. 107 is a cross sectional and cut away top view of FIG. 106 containing the elements shown and described in FIG. 106 with the releasably held needle guard assembly 22 (shown in a partial cut away view) being releasably held adjacent to said hub portion 15, said guard assembly 22 being movable by the stored energy present in the compressed resilient member 19, said resilient member 19 being slidably retained on said needle guard 22 by the notch or indentation 60, said movable needle trap 41 having a lead-in area 33 for locating said resilient member 19 on said needle guard 22 into notches 60 and/or 61, said needle trap 41 also having at least one notch or indentation 61 for releasably retaining said end coils of said resilient member 19, said needle guard 22 having a proximal guide section 34, a distal needle guide aperture 47, a needle trap 41 biasly contacting said hypodermic needle 10 by the inherent memory of the molded configuration of said needle trap 41 and/or the extending force of the surrounding resilient member 19, whereby the advancing movement of said needle guard 22 is limited by a change in profile 3 of said needle 10, said needle 10 having a sharpened distal end 11 and an unsharpened proximal end being fixedly attached to said hub 12.

Said needle 10 being fixedly attached to hub 12 in a needle nest 4, said hub 12 having a flange 16 for removably attaching a protective cover, and at least one flange 101. Said needle trap 41 being hingedly attached to said needle guard 22 by a hinge section 40, said needle guard 22 having a receiving slot 31 to receive the needle trap 41.

FIG. 108 is a cross sectional and cut away top view FIGS. 106 and 107 showing the needle tip 11 being trapped within the needle guard 22 by the movable needle guard 41, comprising a hypodermic needle 10 having a sharpened tip 11, said needle guard 22 being limited in its axial movement by means of a change in profile 3 near the distal end of said needle 10, with the resilient member 19 extended and maintaining an extending force on the needle guard assembly 22, said needle guard 22 is prevented from advancing further by the limiting feature of said change in profile 3, said resilient member 19 being slidably retained on said needle guard 22 by the notch or indentation 60, said movable needle trap 41 having a lead-in area 33 for locating said resilient member 19 on said needle guard 22 into notches 60 and/or 61, said needle trap 41 also having at least one notch or indentation 61 for releasably retaining said end coils of said resilient member 19, said needle guard 22 having a proximal guide section 34, a distal needle guide aperture 47, a needle trap 41 biasly contacting said hypodermic needle 10 by the inherent memory of the molded configuration of said needle trap 41 and/or the extending force of the surrounding resilient member 19, whereby the advancing movement of said needle guard 22 is limited by a change in profile 3 of said needle 10, said needle 10 having a sharpened distal end 11 and an unsharpened proximal end being fixedly attached to said hub 12. Said needle 10 being fixedly attached to hub 12 in a needle nest 4, said hub 12 having a flange 16 for removably attaching a protective cover, and at least one flange 101. Said needle trap 41 being hingedly attached to said needle guard 22 by a hinge section 40, said needle guard 22 having a receiving slot 31 to receive the needle trap 41.

Said proximal guide 34 is shown here maintaining the needle guard 22 in a substantially concentric manner on said hypodermic needle 10. Said needle guard 41 also having a tapered or reducing proximal section 304 for non-binding access by the movable resilient member 19.

FIG. 109 is a full top view of a needle guard 22 having a proximal guide section 34, a reducing section 304, a longitudinally shaped chamber 94, a projection 63 to allow free movement of a movable latch, and a distal guide section 47. This embodiment utilizes a separate needle guard component.

FIG. 110 is a full front view of a needle guard 22 shown in FIG. 109, having a longitudinal chamber 94, a slot 25 to accept a latching means, a distal guide section 47, and an aperture.

FIG. 111 is a cross sectional view of the needle guard 22 shown in FIG. 109 along axis 111—111 showing the slotted configuration, of chamber 94.

FIG. 112 is a full bottom view of a needle guard 22 shown in FIG. 109 having a notch 60, a reducing section 304 and a projection 63 to allow free movement of a movable latch.

FIG. 113 is a full rear view of the movable needle guard 22 shown in FIG. 112 having a chamber 94, an aperture, a notch 60 and a proximal guide section 34.

FIG. 114 is a full top view of the needle guard 220 for a catheter introducer having an inner chamber 94, a proximal guide section 34, a recess 31 to receive a movable needle trap, a middle guide section 93 for locating a needle 10 during assembly procedures, a slot 80 for receiving the proximal end of a separate needle trap 41, a slotted catheter adapter 78, a distal guide section 92, and a projection 91 for releasably holding a catheter hub 13 in a specific orientation on said needle guard 220.

FIG. 115 is a full front view of the needle guard 220 for a catheter introducer shown in FIG. 114 having a middle guide section 93 for locating a needle 10 during assembly procedures, a slotted catheter adapter 78, a distal guide section 92, and a projection 91 for releasably holding a catheter hub 13 in a specific orientation on said needle guard 220. Said needle guard 220 having a needle 10 therethrough, said needle being contained through said needle guard 220 by the separately attached needle trap 41. Said needle 10 being concentrically located through said needle guard 220 located by the needle trap 41.

FIG. 116 is a cross sectional and cut away side view of a separate needle trap 41 having a proximal side 82 which inserts into a slot within a slidable needle guard. Needle trap 41 includes a least one projection 83 for fixedly attaching said needle trap in a needle guard, a lead in side 33 for locating a resilient member during assembly procedures, a notch 61 for maintaining an extending force of said resilient member on said trap 41, and a plurality of sides or skirts 46 to contain a sharpened tip 11 of a needle 10 within said trap 41. Said needle trap 41 can comprise plastic, metal, or any other substantially impenetrable material.

FIG. 117 is a full top view of the housing 85 having a lip 90 and internal fins 97. Said fins 97 can be eliminated by shaping the cross section of said housing 85 to match the housing shape shown in FIG. 120.

FIG. 118 is a cross sectional and cut away top view of a catheter introducer comprising the components shown and described in FIG. 114, having a needle 10 with one sharpened distal end 11, said needle 10 having a change in profile 3 near the distal end of said needle 10, said needle 10 being fixedly attached to a hub 9 by a needle nest 4, said hub 9 having a flange or plurality of projections 16 to accept a removable storage cover, said needle 10 having a needle guard 220 being slidably disposed about said needle 10 and initially positioned adjacent to the proximal end of said needle 10. Said needle guard 220 having a receiving slot 31 for a movable needle trap 41, a slot 80 for fixedly attaching a separate needle trap 41, a catheter adapter 78, and a proximal guide section 34. Said needle trap 41 having a proximal side 82 which is received in said slot 80, a plurality of sharp projections 83 for fixedly attaching said needle trap 41 on said needle guard 220 into slot 80, an extending arm 45 and a projection 42 for releasably holding a catheter hub 13 adjacent to said needle guard 220, said side 82 having a guide section 84 for locating said needle centrally through said guard 220. Said separable catheter 29 having a hub 13 and an inner channel, recess, slot or undercut 32 for being releasably held by said movable arm 42. This embodiment still side loads onto a needle, leaving the delicate tip untouched and sharp.

FIG. 119 is a full top view of the separate needle trap 41 for a syringe or blood collecting assembly, comprising a needle trap 41, a plurality of skirts 46, each created by a fold, a notch 61, a lead in section 33, a proximal side 82, created by a fold, having a plurality of sharp projections 83 and a guide section 84. Notch 61 and lead in section 33 are optional.

FIG. 120 is a cross sectional and cut away top view of a catheter introducer ready for use comprising the components shown and described throughout this application, having a needle 10 with one sharpened distal end 11, said needle 10 being fixedly attached to a hub 9 by a needle nest, said hub 9 having a lead in area 38 for concentrically locating a movable housing 85 onto said needle 10, a flange or plurality of projections 16 to accept a removable storage cover, said needle 10 having a needle guard 22a being slidably disposed about said needle 10 and initially positioned adjacent to the proximal end of said needle 10. Said hub 9 also having a distal hub section 15 and a flashback chamber located at the distal end of said hub 9. Said flashback chamber being closed by means of a removable plug 100.

This drawing shows said needle guard 22a being held within a housing or shroud 85, said housing having a tapered configuration, allowing for concentric placement of said resilient member within said housing and an improved gripping means by the user. Said housing 85 having an inner chamber for receiving a resilient member 19 and a slidable needle guard 22a, said housing 85 may also have exterior serrations or channels serving as a non-slip gripping means. Said needle guard 22a being held within said housing 85 by a snap-fit means created by the wedge 66a and slot 66b at the proximal end of said needle guard 22a. Said housing 85 having a curb 90 serving as a gripping means, and a corresponding, proximal aperture to receive said wedge 66a and slot 66b, said aperture having a "lead-in" 96 for easy assembly of said guard 22a into said housing 85.

Said housing 85 and resilient member 19 are assembled onto the needle 10 by an over the needle 10 procedure. The proximal aperture of said housing 85 is substantially larger than the needle 10 diameter, allowing the housing 85 to easily be assembled onto the needle 10 without touching the delicate tip 11. A means to automatically and concentrically locate the housing 85 on the needle 10 is described in this application. The proximal guide section 34 of the needle guard 22a is only slightly larger than the needle 10 diameter, allowing a close, concentric fit necessary for the invention to function properly. The needle guard 22a is loaded onto the needle 10 from the side and once the clam shell guard 22a is closed, the concentrically located needle guard 22a slides down the needle 10 shaft and snap fits into the concentrically located housing 85 and resilient member 19. The side load guard 22a also works in the same concentric manner once the separate needle trap 41 is fixedly attached to the needle guard 22a once the guard 22a and trap 41 are concentrically located on the needle 10 shaft.

Said needle guard 22a comprising a clam-shell design having a split line 43, a receiving slot 31 for a movable needle trap 41, a distal catheter adapter 78, and a proximal guide section 34 (shown in other drawings in this application). Said needle trap 41 having an extending arm 45 and a projection 42 for releasably holding a catheter hub 13 adjacent to said needle guard 22a. Said separable catheter 29 having a hub 13, an inner channel, recess, slot or undercut 32 for being releasably held by said movable arm 45 and projection 42, and a plurality of flanges 301 to twistedly attach said hub 13 to a luer fitting.

Said slidable needle guard 22a being fixedly attached to a hub portion 9 by means of a limiting tether 24, said tether 24 being fixedly attached to said needle guard 22a by means of an extension 28. Said needle guard 22a having a notch or indentation 60 for releasably holding said resilient member 19 on said needle guard 22a, said movable needle trap 41 having a lead-in area 33 for locating said resilient member 19 on said needle guard 22a into notches 60 and/or 61, said needle trap 41 also having a notch or indentation 61 for retaining said end coils of said resilient member 19, with the distal end of said needle guard 22a having a male section 78 for removably attaching an indwelling I.V. catheter hub 13, said needle trap 41 having a movable arm 45 and projection 42 for releasably retaining a catheter hub 13 from said adapter section 78 after insertion of the catheter 29 into a patient. Said catheter hub 13 having at least one flange 301 and an inner channel, recess, slot or undercut 32 for being releasably held by said movable arm 45 and said projection 42.

Said needle guard lead in 33 section on said needle trap 41 could also comprise longitudinal channels to reduce the contact surface area of said resilient member, reducing frictional contact and reducing the amount of material used to manufacture the component.

FIG. 121 is a cross sectional and cut away top view of a catheter introducer safely trapping the needle tip 11 after the catheter 29 has been inserted into a patient, comprising a needle 10 with one sharpened distal end 11, said needle 10 being fixedly attached to a hub 9 by a needle nest 4, a flange of plurality of projections 16 to accept a removable storage cover, said needle 10 having a needle guard 22a being slidably disposed about said needle 10 and said needle tip 11 being safely positioned within said needle guard 22a. Said hub 9 also having a distal hub section 15 and a flashback chamber located at the distal end of said hub 9. Said flashback chamber being closed by means of a removable plug 100. Said hub 15 having a lead in area 38 for concentrically locating a movable housing 85 onto said needle 10.

FIG. 121 shows needle guard 22a being held within a housing or shroud 85 having an integral resilient member 19. Said housing 85 having an inner diameter which locates the compressed resilient member 19 on the notches 60 and/or 61 on said needle guard 22a, said housing 85 may also have exterior serrations or exterior channels serving as a non-slip gripping means, and a proximal skirt 99 which contacts said hub 15 during assembly, allowing said needle guard 22a to be pressed into said housing 85.

Said needle guard 22a being held within said housing 85 by a snapfit means created by the wedge 66a and slot 66b at the proximal end of said needle guard 22a. Said wedges 66a may have a longitudinal opening 81 at the split line 43 to allow said wedges 66a to compress as said needle guard 22a is snap fit into said housing 85. Said housing 85 may also have a distal curb 90, described in FIG. 105, serving as a gripping means, and a corresponding proximal aperture to receive said wedge 66a and slot 66b, said proximal aperture having a "lead-in" 96 for easy assembly of said guard 22a into said housing 85. Said housing 85 is centrally located onto said needle 10 by an over the needle procedure. Said housing 85 having a proximal skirt 99 with an internal annular chamfer for concentrically locating said housing 85 onto said needle 10 and hub 9 by means of chambered configuration of said needle nest 4. Said skirt 99 is not necessarily needed to implement the present invention.

Said needle guard 22a comprising a clam-shell configuration having a split line 43, a receiving slot 31 for a movable needle trap 41, a distal catheter adapter 78, and a proximal guide section 34 (shown in other drawings in this application). Said needle trap 41 having an extending arm 45 and a projection 42 for releasably holding a catheter hub 13 adjacent to said needle guard 22a. Said separable catheter 29 having a hub 13, undercut 32 for being releasably held by said movable arm 45 and projection 42, and a plurality of flanges 301 to attach said hub 13 to a luer fitting.

Said undercut 32 can be annular or segmented and still provide a holding means to keep said catheter hub 13 adjacent to said needle guard 22a until said needle tip 11 is fully contained within said needle guard 22a.

Said slidable needle guard 22a being fixedly attached to a hub portion 9 by means of a limiting tether 24, said tether 24 being fixedly attached to said needle guard 22a by means of a extension 28 or the like. Said needle guard 22a having a notch or indentation 60 for releasably holding said resilient member 19 on said needle guard 22a, said movable needle trap 41 having a lead-in area 33 for locating said resilient member 19 on said needle guard 22a into notches 60 and/or 61, said needle trap 41 also having a notch or indentation 61 for retaining said end coils of said resilient member 19, with the distal end of said needle guard 22a having a male section 78 for removably attaching an indwelling I.V. catheter hub 13, said needle trap 41 having a movable arm 45 and projection 42 for releasably retaining a catheter hub 13 from said adapter section 78 after insertion of the catheter 29 into a patient. Said catheter hub 13 having at least one flange 301 and an undercut 32 for being releasably held by said movable arm 45 and said projection 42.

FIGS. 122A, 122B and 122C show an isometric view of the catheter described in FIGS. 120 and 121 as the catheter adapter 9 is separated from catheter 29.

FIG. 123 is a full top view of the separate needle trap 41 for the indwelling catheter invention, comprising a needle trap 41, a plurality of skirts 46, each created by a fold or bend, a notch 61, a lead in section 33, a proximal side 82, created by a fold or bend, having a plurality of sharp projections 83 and a guide section 84, a ledge, or retainer 27 created by at least one fold or bend, an extending arm 45, created by a fold or bend, and a projection 42, created by a fold or bend.

FIG. 124 is a full and cut away view of FIG. 123 comprising a separate needle trap 41 for the indwelling catheter invention, comprising a needle trap 41, a plurality of skirts 46, each created by a fold or bend, a notch 61, a lead in section 33, a proximal side 82, created by a fold or bend, having a plurality of sharp projections 83, a ledge, or retainer 27 created by a fold or bend, an extending arm 45, created by a fold or bend, and a projection 42, created by a fold or bend.

FIG. 125 is a is a full, outside, top view of the needle guard assembly 22a for an indwelling catheter shown in its molded configuration comprising a foldable, open-faced needle guard 22a having an extended mounting section 28, a catheter adapter 78, a notch 60 for positioning and maintaining the extending force of a resilient member 19 (not shown) on said needle guard 22a when said guard 22a is in a retained and extending mode, and a wedge 66a and slot 66b at the proximal end of said needle guard 22a. Said needle guard 22a having a movable needle trap 41 being hingedly attached to said needle guard 22a by a hinge 40, said needle trap 41 having an extended arm 45 and projection 42 for releasably retaining a catheter hub from said adapter 78 after insertion of the catheter 29 into a patient. Said needle trap 41 also having at least one notch or multi-level landing 61 for proper positioning of a resilient member 19 (shown in other drawings in this application), said needle trap 41 having a lead in area 33 also for locating said resilient member 19 in a compressed and/or extendible position. Said needle guard 22a being fixedly attached to a tether 24, said tether 24 having at least one protrusion 20 for fixedly attaching said tether 24 to said hub portion 15 or hub 12, or flange 16.

FIG. 126 is a is a full, inside face view of the needle guard assembly 22a for an indwelling catheter shown in its molded configuration comprising a foldable, open-faced needle guard 22a having an extended hinge section 28, a wedge 66a and slot 66b located at the proximal end of said needle guard 22a, said needle guard 22a having a movable needle trap 41 being hingedly attached to said needle guard 22a by a hinge 40, said needle trap 41 having an extended arm 45 and projection 42 for releasably retaining a catheter hub from said adapter 78 after insertion of the catheter into a patient. Said needle guard 22a also having a proximal guide section 34 and a distal guide section 47, which are created when the needle guard 22a sections are joined together, said needle guard 22a also having a middle guide section 93. Said needle guard 22a having a movable needle trap 41 being hingedly attached by the hinge 40, said needle trap 41 having at least one skirt or fin 46 for entrapping said sharpened needle tip 11 (shown in other drawings in this application), said needle guard 22a having a corresponding slot or opening 31 for receiving said needle trap 41, said needle guard 22a having at least one pin 36 and a corresponding opening 37 for frictionally engaging or snap fitting said needle guard 22a sections together about the hypodermic needle 10 (as shown in previous drawings) said pin 36 and slot 37 can be positioned on either side of needle guard 22a sections, said needle guard 22a having an internal guide section 35 and a proximal guide section 34, said needle guard 22a having an internal landing 52 located between said internal guide 35, with said landing 52 having an adjacent landing 53 which serves to guide said hypodermic needle 10 (shown in other drawings in this application) during assembly, storage and use, said landing 53 also houses said sharpened needle tip 11 (shown in other drawings in this application) within said needle guard 22a.

Said needle guard 22a being fixedly attached to an integral, or separate, tether 24. Said tether 24 connects to a hub 15 (not shown).

FIG. 127 is a full front view of the clam shell needle guard assembly 22a for an indwelling catheter shown in an open-faced configuration comprising a needle guard assembly 22a having a movable needle trap 41, said needle trap 41 having an extended arm 45 and a projection 42, an internal guide section 35, a distal catheter adapter 78, an extended hinge section 28, with a plurality of needle guard 22a sections connected adjacent to said hinge section 28, said hinge section 28 having an adequate area for insert molding a separate tether or fixedly attaching said separate tether 24, said hinge section 28 also could have an aperture therethrough for fixedly inserting a separate tether 24. Said needle guard 22a having a split line 43 where the needle guard 22a sections mate or join together, an aperture guide 47 on each section at the distal end, and a post 36 for joining the needle guard assembly 22a sections together. Said post 36 is received by a corresponding slot or opening 37 on the adjacent half of said needle guard 22a.

FIG. 128 is a full rear view of the needle guard assembly 22a for an indwelling catheter shown in an open-faced configuration comprising a needle guard assembly 22a having an extended hinge 28 for joining each needle guard 22a section together, said extended hinge section 28 having a slot or recess for inserting a fixedly attached, or separate tether (not shown). Said needle guard 22a also having an internal guide section 35, a split line 43 where the needle guard 22a sections mate or join together, a proximal guide 34 and proximal wedge projection 66a located on each needle guard 22a section, a moveable needle trap 41, at least one post or protrusion 36 on one needle guard assembly 22a section which enters at least one corresponding slot 37 on the other needle guard assembly 22a section for securing the sections together. Said post 36 is received by a corresponding slot or opening 37.

FIG. 129 is a cross sectional view of the needle guard 22a in FIG. 126 shown along axis 129—129 and comprising a needle guard section 22a, an internal guide section 35 having an angled face to concentrically locate said hypodermic needle through said needle guard 22a, a landing 52 and a split line 43.

FIG. 130 is a cross sectional view of the disclosed needle guard 22a in FIG. 126 shown along axis 130—130 and comprising a needle guard section 22a, and a needle trap 41 having a plurality of skirts or wall sections 46.

FIG. 131 is a full side view of the hollow bore needle 10 of the present invention having an expanded change in profile 3 and a sharpened, distal tip 11.

FIG. 132 is a full top view of the disclosed hollow bore needle 10 having a reduced change in profile 3a and a sharpened, distal tip 11.

FIG. 133 is a full side view of the disclosed hollow bore needle 10 in FIG. 131 having an expanded change in profile 3 and a sharpened, distal tip 11 and a slidable washer or bushing 130 adjacent to said expanded change in profile 3. Washer 130 is limited in axial movement by larger size of expanded change in profile 3.

FIG. 134 is a cross sectional side view of FIG. 133 comprising a hollow bore needle 10 having an expanded change in profile 3 and a sharpened, distal tip 11 with a slidable washer or bushing 130 having an aperture 131 sized to allow washer 130 to slide axially on needle 10, but axial movement of washer 130 on needle 10 is limited by the expanded change in profile 3 because the aperture 131 is smaller than the change in profile 3.

FIG. 135 is s full front view of washer or bushing 130 having an aperture 131.

Figure 136:
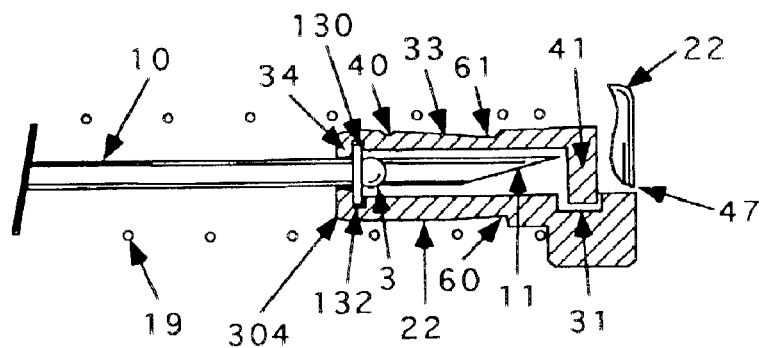
FIG. 136 illustrates an entrapped needle having a change in profile limiting the axial movement of a needle guard assembly that includes a washer or bushing in one embodiment of the present invention.

FIG. 136 is a cross sectional and cut away side view of the needle guard assembly of the present invention showing the needle tip 11 being trapped within the needle guard 22 by the movable needle guard 41, comprising a hypodermic needle 10 having an expanded change in profile 3 and sharpened tip 11, said needle guard 22 being limited in its axial movement by engagement of bushing or washer 130 with expanded change in profile 3 near the distal end of said needle 10, said washer being retained by slot 132 in needle guard 22, with the resilient member 19 extended over movable needle trap 41 and maintaining said needle trap 41 in a locked position. Said needle trap 41 being hingedly attached to said needle guard 22 by a hinge section 40, said needle guard 22 having a receiving slot or nest 31 to receive the needle trap 41.

Said proximal guide 34 and washer 130 are shown here maintaining the needle guard 22 in a substantially concentric manner on said hypodermic needle 10. Said needle guard 41 also having a tapered or reducing proximal section 304 for non-binding access by the movable resilient member 19.

Figure 137:
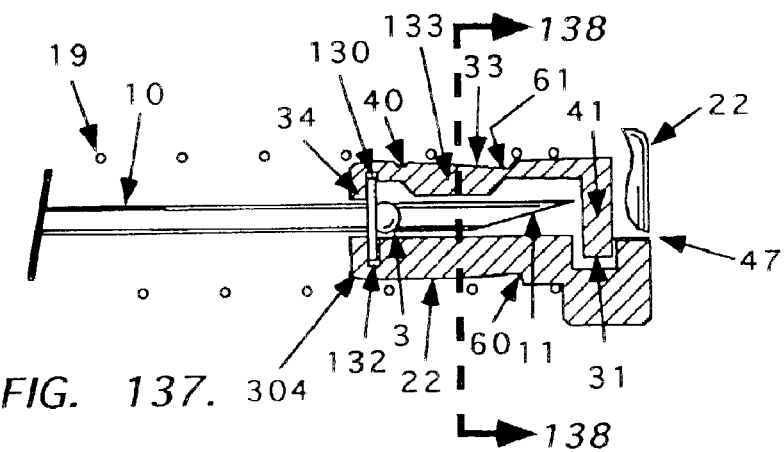
FIG. 137 illustrates an entrapped needle having a change in profile limiting the axial movement of a needle guard assembly that includes a protrusion to contain the needle within the needle guard.

FIG. 137 is a cross sectional and cut away side view of the needle guard assembly 22 shown in FIG. 136 showing the needle tip 11 being trapped within the needle guard 22 by the movable needle trap 41, said needle trap having a rib or protrusion 133 to closely contain said needle 10 within needle guard assembly 22, comprising a hypodermic needle 10 having an expanded change in profile 3 and sharpened tip 11, said needle guard 22 being limited in its axial movement by engagement of bushing or washer 130 with expanded change in profile 3 near the distal end of said needle 10, said washer being retained by slot 132 in needle guard 22, with the resilient member 19 extended over movable needle trap 41 and maintaining said needle trap 41 in a locked position. Said needle trap 41 being hingedly attached to said needle guard 22 by a hinge section 40, said needle guard 22 having a receiving slot or nest 31 to receive the needle trap 41.

Figure 138:
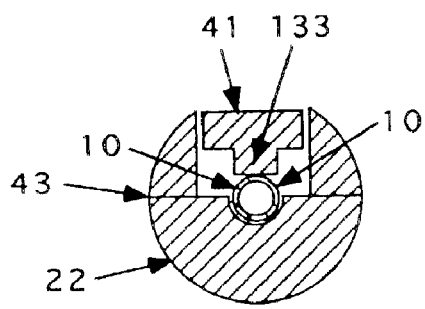
FIG. 138 is a cross sectional front view of the needle and needle guard assembly shown in FIG. 137.

FIG. 138 is a cross sectional front view of the needle guard assembly 22 shown in axis 138—138 of FIG. 137 showing the needle 10 being trapped within the needle guard 22 by the movable needle trap 41, said needle trap having a rib or protrusion 133 to closely contain said needle 10 within needle guard assembly 22.

Figure 139:
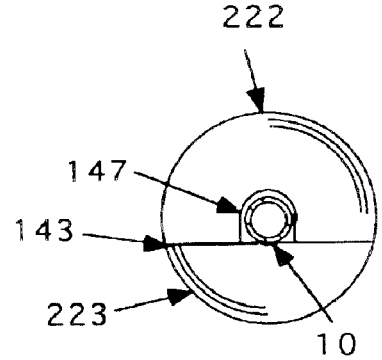
FIG. 139 is a full front view of a needle guard assembly having a split line that is off set.

FIG. 139 is a full front view of the needle guard assembly 222 comprising an off set split line 143 creating aperture 147 that needle 10 can slide through, and a corresponding needle guard section 223.

FIG. 140 is a full side view of a prior art needle 310 having an anti-coring tip 311 and a bend, or change in axis, 303 on needle shaft 310.

FIG. 141 is a cross sectional side view of needle 310 being covered with slidable housing 322, said needle 310 having an anti-coring tip 311 and a bend, or change in axis, 303 at a position on the needle shaft 310 that limits axial movement of housing 322 on shaft 310, said housing 322 having a distal opening 347, a proximal guide shaft 334 that is sized to slide on shaft 310, said housing 322 is limited in axial movement on shaft 310 by proximal guide 334 engaging bend 303. Said proximal guide 334 being sufficient to limit axial movement of housing 322 on needle 310.

FIG. 142 is a cross sectional side view of needle 310 having an anti-coring tip 311 and a bend, or change in axis,303 in the needle shaft 310 that limits axial movement of bushing 313 on shaft 310. A needle guard assembly as shown in FIGS. 136 and 137 may include bushing 313 to limit axial movement of a needle guard assembly on shaft 310.

FIG. 143 is a cross-sectional side view of the needle guard assembly of the present invention showing the interaction of the needle guard assembly 322 and resilient member 319, said hypodermic needle 310 having an anti-coring sharpened needle tip 311 and a change in axis 303, comprising a slidable needle guard assembly 322 with a hypodermic needle 310 therethrough, with resilient member 319 urging the needle guard assembly 322 toward the distal end of the hypodermic needle 310. The needle guard assembly 322 having proximal guide section 334, a movable needle tip guard 341 with a hinge section 340, said needle tip guard 341 is molded in a manner whereby the needle tip guard 341 comprises an inherent biasing force toward the hypodermic needle 310, another biasing force is exerted on the needle tip guard 341 by the extending force of the resilient member 319, said needle tip guard 341 enters the corresponding recess 331 when said needle tip guard 341 advances beyond the sharpened needle tip 311, said needle tip guard 341 slidably contacts said hypodermic needle 310.

FIG. 144 is cross-sectional side view of the needle guard assembly shown in FIG. 143 showing containment of the sharpened needle tip 311 within the needle guard assembly 322 comprising a needle guard assembly 322 with a hypodermic needle 310 therethrough, said needle guard assembly 322 being urged beyond the distal end of the hypodermic needle 310 and sharpened needle tip 311 by the extending force of a resilient member 319 whereby the moveable, self-biasing needle tip guard 341 of the needle guard assembly 322 moves in front of the sharpened needle tip 311, containing the sharpened needle tip 311 within the needle guard assembly 322 and behind the substantially impenetrable needle tip guard 341 having a hinge section 340. The needle guard assembly 322 having proximal guide section 334 that engages bend in needle 303 to limit axial movement of needle guard 322 on needle 310.

Additionally, the extending force of the resilient member 319 urges the needle tip guard 341 inwardly to a covering position, said resilient member 319 surrounds both the needle guard assembly 322 and the outer wall of the needle tip guard 341 holding the needle tip guard 341 in a closed, protective position by a radially confining force. In the protected, closed position, the needle tip guard 341 enters the corresponding recess 331 of the needle guard assembly 322, preventing movement and ensuring safe containment of the sharpened needle tip 311 within the needle guard assembly 322.

FIG. 145 is a full side view and cut away drawing of the needle hub of the present invention comprising a hypodermic needle hub 612 with at least one flange 601 for attaching the needle hub 612 to a luer fitting, a needle nest 604 (not shown in this view) for fixedly attaching the needle (not shown in this view), an inner aperture 616 (not shown in this view) creating a fluid/gaseous path between needle hub 612 and needle 610 (not shown in this view), at least one aperture 644 located at the distal end of a deformable housing 615 for receiving a protrusion for releasably retaining a member on needle hub 612, said housing 615 having an inner cavity or chamber 617 and deformable wall section 650.

FIG. 146 is a full front view drawing of the needle hub of FIG. 145 comprising a deformable housing 615 having an inner aperture 616 for creating a fluid/gaseous path between hub 612 (not shown in this view) and a hypodermic needle 610 (not shown in this view), said housing 615 having an inner cavity or chamber 617 and deformable wall section 650.

FIG. 147 is a full top view drawing of the needle hub of FIG. 145. comprising a hypodermic needle hub 612 with at least one flange 601 for attaching the needle hub 612 to a luer fitting, at least one aperture 644 located at the distal end of a deformable housing 615 for receiving a protrusion for releasably retaining a member on needle hub 612.

FIG. 148 is a full top view drawing of a ready to use needle apparatus of the present invention showing needle guard 622 being releasably retained in deformable housing 615 by engagement of protrusion 645 of needle guard 622 into aperture 644 of deformable member or housing 615, comprising a hypodermic needle hub 612 with at least one flange 601 for attaching the needle hub 612 to a luer fitting. Said needle guard 622 may include a resilient member (not shown in this view) to propel needle guard 622 to the distal end of needle 610.

FIG. 149 is a full front view of the needle guard assembly 622 of FIG. 148 comprising at least one protrusion 645, an off set split line 643 creating aperture 647 and a corresponding needle guard section 623.

FIG. 150 is a full front view of the needle guard apparatus of the present invention comprising needle guard assembly 622 being releasably retained within deformable member or housing 615, said housing having a cavity or chamber 617 for accepting a member or guard, said needle guard assembly 622 comprising a passageway for needle 610, at least one protrusion 645, an off set split line 643 creating aperture 647 and a corresponding needle guard section 623, said deformable housing 615 having at least one aperture 644 located at the distal end for receiving and releasably retaining protrusion 645 of needle guard assembly 623 within cavity 617 of housing 615.

FIG. 151 is a full front view of the needle apparatus of FIG. 150 showing the needle guard assembly 622 being selectively released when a compressive force "F" is exerted on deformable housing 615, said needle guard assembly 622 comprising a passageway for needle 610, at least one protrusion 645 that is released from aperture 644 (not shown in this view) when deformable housing 615 is squeezed. Said needle guard assembly having an off set split line 643 creating aperture 647 creating a passageway for needle 610, and a corresponding needle guard section 623, said deformable housing 615 having at least one aperture 644 located at the distal end for releasably retaining protrusion 645 of needle guard assembly 623 within cavity 617 of housing 615.

FIG. 152 is an isometric view of the needle guard assembly 622 ready to use releasably being retained within deformable housing 615 having a deformable wall section 650, said housing 615 being selectively attachable to hub 602 having a luer end 601, said needle guard assembly 622 comprising a movable trap 641, a passageway for needle 610 with a sharpened tip 611 and a change in profile 603, at least one protrusion 645 (shown retained within aperture 644 of housing) on section 623, an off set split line 643 creating aperture 647 and corresponding needle guard section 623, said deformable housing 615 having at least one aperture 644 located at the distal end for receiving said protrusion 645 of corresponding needle guard assembly 623. Said housing 615 having an inner guide or rib 651 to properly position needle guard 622 within hub 615, said housing 615 being selectively attached to hub 602 by a retaining means or hook 613 and may include at least one rib 625 for gripping said housing 615. Needle guard 622 is released from a retained position by squeezing deformable housing 615 and guard 622 is propelled along the needle 610 by resilient member 619.

FIG. 153 is an isometric view of the needle guard assembly of FIG. 152 showing containment of the sharpened needle tip 611 within the needle guard assembly 622, said needle guard assembly 622 comprising a movable trap 641 that is locked in a protective position on needle tip 611, needle guard is limited in axial movement by engagement of needle guard 622 with change in profile 603 of needle 610. Additionally, when the needle guard assembly 622 is disposed within the housing 615, the movable trap 641 is interposed between two posts 642a and 642b. The interposition of the moveable trap between the two posts 642a and 642b limits the rotational movement of the needle guard assembly 622 when the needle guard assembly 622 is disposed within the housing 615.

A number of embodiments have been disclosed herein as they relate to the needle protective device of the present invention. It is important to understand that many of the elements described herein may be interchangeable. It is also important to note that the invention can comprise a variety of embodiments, ranging from a single piece, injection molded part, where the components are manufactured unitarily, to a plurality of components, all which achieve the desired result of safely capturing the sharpened needle tip.

What is claimed is:

1. A needle protective device comprising:
   a) a needle defining proximal and distal ends;
   b) a needle guard mounted about the needle and traversable between the proximal and distal ends of the needle, the needle guard being biased to the distal end of the needle, the needle guard having at least one protrusion; and
   c) a housing fixed to a proximal end of the needle and sized and configured to receive the needle guard, the housing having at least one aperture sized and configured to receive the needle guard protrusion when the needle guard is at the proximal end of the needle.

2. The device of claim 1 wherein the needle guard defines a circular outer diameter, and the housing has an inner elliptical configuration defining a minor axis equal to the outer diameter and a major axis, the aperture of the housing being aligned with the minor axis of the housing such that application of a compressive force on the major axis expands the minor axis to disengage the protrusion from the aperture.

3. The device of claim 2 wherein the housing is deformable.

4. The device of claim 3 wherein the housing is manufactured from material selected from the group consisting of plastic, rubber and combinations thereof.

5. The device of claim 1 further comprising a guide attached to the housing to stabilize lateral movement of the needle guard within the housing.

6. The device of claim 1 further comprising a movable trap attached to the needle guard to stabilize rotational movement of the needle guard when the needle guard is at the proximal end of the needle.

7. The device of claim 1 further comprising a resilient member mounted about the needle and disposed between the housing and the needle guard to bias the needle guard to the distal end of the needle.

8. The device of claim 7 wherein the needle guard defines a flange and a base, and the resilient member exerts a force on the base to propel the needle guard to the distal end of the needle then on the flange to maintain a moveable trap within the needle guard.

9. The device of claim 8 wherein the resilient member is a compression spring.

10. The device of claim 9 wherein the base has a conical configuration for guiding the spring about the base as the spring is being compressed.

* * * * *

UNITED STATES PATENT AND TRADEMARK OFFICE
CERTIFICATE OF CORRECTION

| | | |
|---|---|---|
| PATENT NO. | : 6,860,871 B2 | Page 1 of 2 |
| APPLICATION NO. | : 10/442376 | |
| DATED | : March 1, 2005 | |
| INVENTOR(S) | : Kuracina et al. | |

It is certified that error appears in the above-identified patent and that said Letters Patent is hereby corrected as shown below:

On the Title Page

Item (63), column 1, line 2, after "6,629,959" insert -- , which is a continuation-in-part of application No. 09/144,398, filed on Aug. 31, 1998, now Pat. No. 6,443,929, which is a continuation of application No. 08/807,328, filed on Feb. 27 1997, now Pat. No. 5,879,337 --, and insert item -- (60) Provisional application No. 60/012,343, filed on Feb. 27, 1996, provisional application No. 60/025,273, filed on Sep. 12, 1996, and provisional application No. 60/031,399, filed on Nov. 19, 1996. --, therefor.

In the Specification

Column 1, line 6, after "959" insert -- , which is a continuation-in-part of U.S. Patent No. 6,443,929 --, therefor.

Column 1, line 11, delete "Non-Provisional", therefor.

Column 1, line 12, after "(1)" insert -- provisional application --, therefor.

Column 1, line 15, after "(2)" insert -- provisional application --, therefor.

Column 1, line 16, after "(3)" insert -- provisional application --, therefor.

Column 1, line 19, after "(4)" insert -- a continuation of --, therefor.

Column 1, line 21, after "5,879,337" insert -- , which is a regular application of provisional application No. 60/012,343, filed on Feb. 27, 1996, provisional application No. 60/025,273, filed on Sep. 12, 1996, and provisional application No. 60/031,399, filed on Nov. 19, 1996 --, therefor.

Column 1, line 21, after ";" insert -- and --, therefor.

Signed and Sealed this
Seventeenth Day of May, 2016

Michelle K. Lee
*Director of the United States Patent and Trademark Office*

CERTIFICATE OF CORRECTION (continued)
U.S. Pat. No. 6,860,871 B2

In the Specification

Column 1, lines 21-24, delete "U.S. patent application Ser. No. 09/172,185 entitled INTRAVENOUS CATHETER ASSEMBLY, now issued as U.S. Pat. No. 6,001,080, filed on Oct. 13, 1998; and" and insert -- a continuation of --, therefor.

Column 1, line 26, after "NEEDLES" insert -- , now issued as a U.S. Patent No. 6,443,929 --, therefor.

Column 1, line 27, after "1998" insert -- , which is a continuation of U.S. Pat. No. 5,879,337 --, therefor.